US010488403B2

(12) United States Patent
Ghosh

(10) Patent No.: US 10,488,403 B2
(45) Date of Patent: Nov. 26, 2019

(54) METHOD FOR THE ISOLATION OF MICROVESICLES

(71) Applicant: Atlantic Cancer Research Institute, Moncton (CA)

(72) Inventor: Anirban Ghosh, Dieppe (CA)

(73) Assignee: Atlantic Cancer Research Institute, Moncton, New Brunswick (CA)

( * ) Notice: Subject to any disclaimer, the term of this patent is extended or adjusted under 35 U.S.C. 154(b) by 0 days.

(21) Appl. No.: 14/415,349

(22) PCT Filed: Jul. 19, 2013

(86) PCT No.: PCT/CA2013/000650
§ 371 (c)(1),
(2) Date: Jan. 16, 2015

(87) PCT Pub. No.: WO2014/012168
PCT Pub. Date: Jan. 23, 2014

(65) Prior Publication Data
US 2015/0192571 A1   Jul. 9, 2015

Related U.S. Application Data

(60) Provisional application No. 61/673,353, filed on Jul. 19, 2012.

(51) Int. Cl.
*G01N 33/50* (2006.01)
*G01N 33/574* (2006.01)
(Continued)

(52) U.S. Cl.
CPC ....... *G01N 33/5091* (2013.01); *A61K 31/728* (2013.01); *B01D 15/265* (2013.01); *B01D 15/3823* (2013.01); *B01J 20/24* (2013.01); *B01J 20/265* (2013.01); *B01J 20/28009* (2013.01); *B01J 20/328* (2013.01); *B01J 20/3274* (2013.01); *C12Q 1/6886* (2013.01); *G01N 33/57415* (2013.01); *G01N 33/57496* (2013.01);
(Continued)

(58) Field of Classification Search
None
See application file for complete search history.

(56) References Cited

U.S. PATENT DOCUMENTS 6,899,863 B1 * 5/2005 Dhellin .............. A61K 39/0011
424/1.21
2003/0187027 A1   10/2003 Schreiber et al.
(Continued)

FOREIGN PATENT DOCUMENTS

WO   WO2001/36601   5/2001
WO   WO2008/028917   3/2008
(Continued)

OTHER PUBLICATIONS

Misra et al., FEBS Journal 278: 1429-1443 (2011).*
(Continued)

*Primary Examiner* — Erin M. Bowers
(74) *Attorney, Agent, or Firm* — Bereskin & Parr LLP/S.E.N.C.R.L.; Michael Fenwick

(57) ABSTRACT

The present disclosure relates to a method for the isolation of microvesicles comprising contacting the sample with at least one polysaccharide to isolate the microvesicles.

24 Claims, 13 Drawing Sheets

(51) Int. Cl.
    B01D 15/26 (2006.01)
    B01D 15/38 (2006.01)
    B01J 20/24 (2006.01)
    B01J 20/26 (2006.01)
    B01J 20/32 (2006.01)
    B01J 20/28 (2006.01)
    A61K 31/728 (2006.01)
    C12Q 1/6886 (2018.01)

(52) U.S. Cl.
    CPC .... *B01D 15/3885* (2013.01); *C12Q 2600/118* (2013.01); *C12Q 2600/178* (2013.01); *G01N 2570/00* (2013.01); *Y10T 436/255* (2015.01); *Y10T 436/25375* (2015.01)

(56) References Cited

U.S. PATENT DOCUMENTS

| 2004/0072849 | A1  | 4/2004 | Schreiber et al. | |
| 2010/0184046 | A1* | 7/2010 | Klass | C12Q 1/6886 435/7.1 |

FOREIGN PATENT DOCUMENTS

| WO | WO2009/100029 | 8/2009 |
| WO | WO2012/020307 | 8/2009 |

OTHER PUBLICATIONS

Pouyani et al., Bioconjugate Chem. 5(4): 370-372 (1994).*
Wolny et al., J. Biol. Chem. 285: 30170-30180 (2010).*
Peach et al., J. Cell Biol. 122: 257-264 (1993).*
Shin et al., Methods Enzymol. 404: 206-215 (2005).*
Jayachandran et al. Methodology for Isolation, Identification and Characterization of Microvesicles in Peripheral Blood. 37 (1-2):207-214. 2012.
Momen-Heravi et al. Impact of Biofluid Viscosity on Size and Sedimenation Efficiency of the Isolated Microvesicles. Frontiers in Physiology, 3(162):1-6, 2012.
György B, Szabó TG, Pásztói M, Pál Z, Misják P, Aradi B, László V, Pállinger E, Pap E, Kittel A, Nagy G, Falus A, Buzás EI. Membrane vesicles, current state-of-the-art: emerging role of extracellular vesicles. Cell Mol Life Sci. Aug. 2011;68(16):2667-88.
Chen et al. Microfluidic Isolation and Transcriptome Analysis of Serum Microvesicles. Lab. Chip. 10(4):505-511, 2010.
Sternson, SM et al. Synthesis of 7200 Small Molecules Based on a Substructural Analysis of the Histone Deacetylase Inhibitors Trichostatin and Trapoxin. Org. Lett., vol. 3(26):4239-4242, 2001.
Soo CY, Song Y, Zheng Y, Campbell EC, Riches AC, Gunn-Moore F, Powis SJ. Nanoparticle tracking analysis monitors microvesicle and exosome secretion from immune cells. Immunology. Jun. 2012;136(2):192-7.
Meckes DG Jr, Raab-Traub N. Microvesicles and viral infection.J Virol. Dec. 2011;85(24):12844-54.
Camussi G, Deregibus MC, Bruno S, Grange C, Fonsato V, Tetta C. Exosome/microvesicle-mediated epigenetic of reprogramming cells. Am J Cancer Res. 2011;1(1):98-110.
Liu ML, Williams KJ. Microvesicles: potential markers and mediators of endothelial dysfunction. Curr Opin Endocrinol Diabetes Obes. Apr. 2012;19(2):121-7.
Taylor DD, Gercel-Taylor C. Exosomes/microvesicles: mediators of cancer-associated immunosuppressive microenvironments. Semin Immunopathol. Sep. 2011;33(5):441-54.
Tetta C, Bruno S, Fonsato V, Deregibus MC, Camussi G. The role of microvesicles in tissue repair. Organogenesis. Apr.-Jun. 2011;7(2):105-15.
Pap E. The role of microvesicles in malignancies. Adv Exp Med Biol. 2011;714:183-99.
Xiong J, Miller VM, Li Y, Jayachandran M. Microvesicles at the crossroads between infection and cardiovascular diseases. J Cardiovasc Pharmacol. Feb. 2012;59(2):124-33.
Rautou PE, Mackman N., Del-etion of microvesicles from the circulation. Circulation. 2012; 125: 1601-1604.
Sadallah S, Eken C, Schifferli JA. Ectosomes as modulators of inflammation and immunity. Sadallah S, Eken C, Schifferli JA. Clin Exp Immunol. Jan. 2011;163(1):26-32.
Camussi G, Deregibus MC, Bruno S, Cantaluppi V, Biancone L. Exosomes/microvesicles as a mechanism of cell-to-cell communication. Kidney Int. Nov. 2010;78(9):838-48.
D'Souza-Schorey C, Clancy JW. Tumor-derived microvesicles: shedding light on novel microenvironment modulators and prospective cancer biomarkers. Genes Dev. Jun. 15, 2012;26(12):1287-99.
Biomarkers Definitions Working Group. Biomarkers and surrogate endpoints: preferred definitions and conceptual framework. Clin Pharmacol Ther. 2001; 69: 89-95.
Pouyani T, Prestwich GD, Biotinylated hyaluronic acid: a new tool for probing hyaluronate-receptor interactions. Bioconjug Chem. Jul.-Aug. 1994;5(4):370-2.
Wagner, G.M.; Chiu, D T-Y; Yee, M.C.; Lubin, B.H.; Red Cell Vesiculation a Common Membrane Physiologic Event. Database Biosis [Online]. Biosciences Information Service, 1986.
Rood, I.M.; Deegens, J K.J.; Merchant, M.L.; Tamboer, W P.M.; Wilkey, D.W.; Wetzels, J.F.M. and Klein, J.B. Comparison of Three Methods for Isolation of Urinary Microvesicles to Identify Biomarks of Nephrotic Syndrome. Kidney International 78:810-816, 2010.
van der Pol, E.; Boing, A.N.; Harrison, P.; Sturk, A. and Nieuwland, R. Classification, Functions, and Clinical Relevance of Extraceullular Vesicles. Pharmacol Rev. 64:676-705, 2012.
Supplementary Partial European Search Report for EP 13820217.1.
Dong-Sic-Choi et al., Proteomic Analysis of Microvesicles Derived from Human Colorectal Cancer Ascites. Proteomics, 11(13):2745-2751, 2011.

* cited by examiner

Healthy Female plasma | Breast cancer Stage-IV plasma

MCF-10A | MDA-MB-231

METHOD FOR THE ISOLATION OF MICROVESICLES

CROSS REFERENCE TO RELATED APPLICATIONS

This is a national stage application of PCT/CA2013/000650, filed Jul. 19, 2013, which claims priority from U.S. Provisional patent application Ser. No. 61/673,353 filed Jul. 19, 2012, all of which are incorporated herein by reference in their entirety.

FIELD

This disclosure relates to a method for the isolation of microvesicles using polysaccharides.

BACKGROUND

Microvesicles (MVs) are a spectrum of membrane-bound bodies having a size of about 10 nm to about 5000 nm, more typically between 30 nm and 1000 nm containing cytoplasmic material shed by cells during various physiological conditions. Microvesicles have long been regarded as cellular debris. Microvesicles contain and transport proteins and nucleic acids. However, it has recently been demonstrated that microvesicles are distinguished from mere debris and it has been established that microvesicles have normal, as well as pathological, inter-cellular signalling functions. Increased levels of microvesicles are detected in blood and other body fluids in cancers and various pathological conditions[1-11]. Thus the significance of microvesicles as diagnostic tool is well established yet technologies for routine clinical diagnostic and prognostic application of microvesicles are not well developed[12-13].

SUMMARY

This disclosure relates to methods for the isolation of microvesicles from a sample containing microvesicles comprising contacting the sample with at least one polysaccharide under conditions for the isolation of the microvesicles.

The disclosure also includes a method for the diagnosis of a pathological condition, such as cancer, comprising
  (i) obtaining a biological sample from a subject;
  (ii) isolating microvesicles from the sample using a method of the present disclosure;
  (iii) detecting one or more pathological markers, such as a cancer biomarker, and/or markers for a particular tissue or cell-type, wherein the presence or absence of the pathological marker in the sample indicates the presence of the condition in the subject.

In addition, the present disclosure also includes a method for monitoring the progression of a pathological condition, such as cancer, the method comprising isolating microvesicles from the sample obtained from a subject using a method of the present disclosure to obtain a reference value comprising one or more markers, such as markers for a particular tissue or cell-type and/or one or more cancer biomarkers and comparing them with the values of microvesicles in samples taken from the subject at a plurality of time points, wherein any difference in the level of marker(s) in those microvesicles relative to the reference value over time indicates progression of the pathological condition, such as cancer, and an opposite reading of the marker(s) in those microvesicles relative to the reference value over time indicates amelioration of the cancer and/or other pathological conditions.

The present disclosure also includes methods of determining the effectiveness of therapy in the treatment of a pathological condition, such as cancer. Accordingly, there is included a method for determining if a subject, suffering from a pathological condition, is responsive to a therapy for treatment of the condition, comprising,
  (i) isolating a first amount of microvesicles in a first biological sample obtained from a subject using a method of the present disclosure;
  (ii) measuring for one or more markers, such as a cancer biomarker, in the microvesicles from the first biological sample;
  (iii) subsequently administering the therapy to the subject;
  (iv) isolating a second amount of microvesicles in a second biological sample from the subject using a method of the present disclosure;
  (v) measuring for the one or more markers, such as a cancer biomarker, in the microvesicles from the second biological sample,
wherein a difference in the one or more markers, such as a cancer biomarker, in the second amount of microvesicles compared to the values of the first amount of microvesicles in the first biological sample indicates the degree of responsiveness to the therapy in the subject.

The present disclosure also includes an assay for detecting a pathological condition in an animal, such as farmed animals, birds or fish, comprising:
  (i) isolating an amount of microvesicles in a control sample from a healthy animal (an animal without the pathological condition) using a method of the present disclosure;
  (ii) measuring for one or more markers in the microvesicles from the control sample;
  (iii) isolating an amount of microvesicles in a test sample from the animal using a method of the present disclosure;
  (iv) measuring for the one or more markers in the microvesicles from the test sample,
wherein a change (increase or decrease) in the one or more markers in the microvesicles from the test sample compared to the control-sample indicates the presence of a pathological conditions in the animal. Depending on the pathological condition, the presence of one or more of the markers will increase or decrease. For example, an infection will result in the pathological marker being higher in the test samples than the control, while a metabolic disease will result in the marker being lower in test samples than the control. Examples of biomarkers include, but are not limited to, metabolites, proteins, peptides, DNA, RNA, mRNA, miRNA, LincRNA, misc-RNA, circular-RNA, etc.

The present disclosure also includes an assay for analyzing food quality, such as dairy and meat products. Accordingly, there is included a method for determining the quality of a food sample, for example, a meat or dairy food sample, comprising,
  (i) isolating an amount of microvesicles from a safe control sample or a standard using a method of the present disclosure;
  (ii) measuring for one or more markers in the microvesicles from the safe control sample;
  (iii) isolating an amount of microvesicles in a test sample using a method of the present disclosure;
  (iv) measuring for the one or more markers in the microvesicles from the test sample,
wherein an increase in the one or more markers in the microvesicles isolated from the test sample compared to the values of the control-sample indicates the food sample has been contaminated with a pathogen. Examples of biomarkers include, but are not limited to, metabolites, proteins, peptides, DNA, RNA, mRNA, miRNA, LincRNA, misc-RNA, circular-RNA, etc.

The present disclosure also includes a method of isolation and subsequent testing of microvesicles from the fluid, media or discharges from any organism (unicellular to multicellular, wild or farmed).

Further aspects and advantages of the embodiments described herein will appear from the following description taken together with the accompanying drawings.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

DETAILED DESCRIPTION (I) Definitions

Figure 1A:
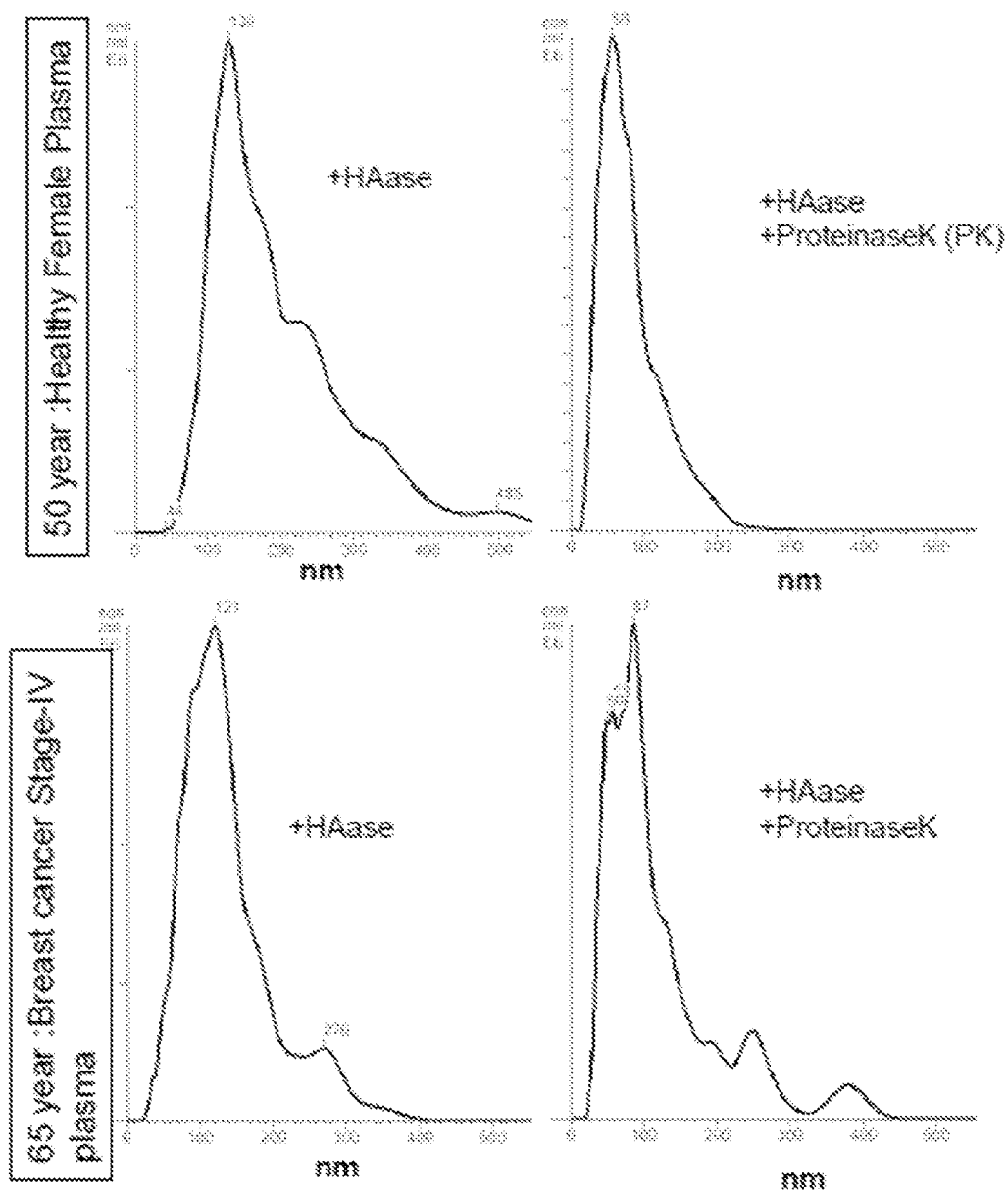
FIG. 1A are graphs showing the particle size of isolated microvesicles from a healthy subject and a breast cancer patient's plasma using a method of the disclosure from different cell lines

The term "microvesicles" as used herein refers to a membrane-bound particle having a diameter (or largest dimension where the particle is not spheroid) of between about 10 nm to about 5000 nm, more typically between 30 nm and 1000 nm, wherein at least part of the membrane of the microvesicle is directly obtained from a cell of single or multicellular organism. Therefore, microvesicles include those that are shed from a donor cell, and will typically also include exosomes[1-12]. Therefore, and depending on the manner of generation (e.g., membrane inversion, exocytosis, shedding, or budding), the microvesicles contemplated herein may exhibit different surface/lipid characteristics. Microvesicles are also referred to as "exosomes", "microsomes", "secretory exosomes", "argosomes" and "microparticles", which are included within the definition.

The term "isolation" or "isolating" as used herein refers to a method of the present disclosure to separate, enrich and/or purify microvesicles from a particular sample.

The term "sample" as used herein refers to a material or mixture of materials containing microvesicles and includes biological samples and clinical samples that contain microvesicles for isolation. Samples may be obtained from human subjects or an organism, such as an animal, and may include a bodily fluid (such as blood, blood serum, plasma, urine, milk and saliva) or tissue biopsy or the fluid, media or discharges form any organism (unicellular to multicellular, wild or farmed).

The term "contacting" as used herein refers to the manner in which a sample and at least one polysaccharide are mixed, or blended, such that the polysaccharides and microvesicles in the sample are able to form a polysaccharide-microvesicle complex.

The term "polysaccharide" as used herein in its ordinary sense refers to polymeric carbohydrate structures, formed of repeating units of monosaccharides, such as six-carbon-monosaccharides, joined by glycosidic bonds. Polysaccharides may be a homopolysaccharide or a heteropolysaccharide depending on the monosaccharide components: a homopolysaccharide consists of same types of monosaccharides whereas a heteropolysaccharide is composed of different types of monosaccharides. The polysaccharides may be linear, but may also include various degrees of branching. The term polysaccharide includes those having typically 10 or more repeat units. The polysaccharides can be from any source, for example, they can be derived from plant material, animal material, bacteria (naturally-occurring or genetically engineered), cultured mammalian cell-lines (naturally-occurring or genetically engineered), cultured protozoa (naturally-occurring or genetically engineered), yeast (naturally-occurring or genetically engineered), insect-cells (naturally-occurring or genetically engineered) or can be produced synthetically. The polysaccharides can be subjected to one or more processing steps, for example, purification, chemical-fuctionalization, attachment to solid supports, and the like methods described in arts. Any suitable method known in the art for synthesizing, preparing, and/or purifying suitable polysaccharides can be employed.

The term "conditions for the isolation of the microvesicles" as used herein refers to the conditions in which the isolation of the microvesicles from the sample is attained, for example, suitable temperatures, duration, dilution of biological sample with physiological saline, pre-clearing, centrifugation force, solid matrix assisted isolation, etc.

The term "suitable" as used herein means that the selection of the particular conditions would depend on the specific manipulation to be performed, and the identity of the molecule(s) involved, but the selection would be well within the skill of a person trained in the art. Unless otherwise indicated, all methods and assays described herein are to be conducted under conditions sufficient to achieve the desired result. A person skilled in the art would understand that all such conditions, including, for example, solvent, time, temperature, pressure, and/or molar, volume or weight ratios, can be varied to optimize the desired result and it is within their skill to do so.

The term "method of the disclosure" as used herein refers to a method of isolating microvesicles using one or more polysaccharides, including all of the various embodiments thereof, described herein.

The term "microfluidics" refers to an apparatus for precise manipulation of liquids in minute volume, typically 200 nano-liters to 100 micro-liters.

The term "subject" as used herein refers to the source organism from where a sample is obtained and includes but is not limited to human, animal, fish, bird and other unicellular and multicellular organisms.

The term "marker" when used in the context of a "marker", "biomarker" or "pathological marker" as used herein refers to biological molecules or cellular events that link to a specific health outcome and help in understanding degree of risk for disease or pathological condition. A person skilled in the art would understand that a marker is a characteristic that is objectively measured and evaluated as an indicator of normal biological processes, pathogenic processes, or pharmacologic responses to a therapeutic intervention[14]. Examples of biomarkers include, but are not limited to, metabolites, proteins, peptides, DNA, RNA, mRNA, miRNA, LincRNA, misc-RNA, circular-RNA, etc. The markers are found within the microvescicles.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Method for the Isolation of Microvesicles

Increased levels and/or different populations of microvesicles are detected in bodily fluids, such as blood, when pathological conditions, such as cancer, are present in the body. Thus, methods for isolating microvesicles are beneficial for the early diagnosis of pathological conditions, such as cancer.

The present disclosure relates to a method of isolating microvesicles from a sample. Accordingly, in one embodiment there is provided a method for the isolation of microvesicles from a sample containing microvesicles, comprising:

(i) contacting the sample with at least one polysaccharide under conditions for the isolation of the microvesicles.

Without being bound by theory, it is believed that the polysaccharides used in the method of the present disclosure bind to one or more proteins, glycoproteins, lipid and/or nucleic acid of the microvesicles allowing for the isolation of the microvesicles.

In some embodiments, the polysaccharide is a natural or synthetic polysaccharide. The polysaccharide for isolating the microvesicles may be a linear or a branched polysaccharide. The polysaccharide may be of any molecular weight, but in some embodiments, the polysaccharide has a molecular weight of at least 2 Kilodalton (KDa) to 10 Megadalton (MDa), optionally between 3 KDa and 7 MDa. In certain embodiment, the polysaccharide has a molecular weight of at least 2 KDa, optionally 3 KDa, optionally 15 KDa, optionally 100 KDa, optionally 150 Kda, optionally 500 KDa, optionally 1 MDa, optionally 5 MDa, optionally 7 MDa or above.

Examples of the at least one polysaccharide encompassed by the present disclosure, include, but are not limited to, amylose, cellulose, chitin, agarose, dextran, dextran sulfate, callose, laminarin, chrysolaminarin, mannan, fucoidan, glycogen, amylopectin, cellulose, chitin, a glycosaminoglycan, and derivatives of any of the above, or mixtures thereof. Examples of glycosaminoglycan include, but are not limited to, chondroitin sulfate, dermatan sulfate, keratan sulfate, heparin, heparan sulfate or hyaluronan. In one embodiment, the at least one polysaccharide is hyaluronan.

In other embodiments, the polysaccharide is bonded to solid supports which aid in the separation of the microvesicles from the sample. For example, the polysaccharide may be bonded to a solid-matrix such as polystyrene or glass, which helps in the isolation of the microvesicles from the sample. In other embodiments, the solid matrix comprises polystyrene coated paramagnetic particles which is then easily isolated using a magnetic field.

In some embodiments, the polysaccharide is bonded to a ligand to help in the purification of the microvesicles from the sample. For example, the polysaccharide is bound to a component of the biotin-avidin system. For example, the polysaccharide may be bound to biotin, and the microvesicles are isolated from the sample by exposing the biotin-bound polysaccharide to avidin or a solid matrix containing avidin. It is understood that the biotin label is stable and small; it rarely interferes with the function of labeled molecules to be used for the development of robust and highly sensitive assays. Avidin and other biotin-binding proteins, including streptavidin and NeutrAvidin Protein. These biotin binding proteins can be coated onto polystyrene, glass and paramagnetic particles or matrix as described in arts.

In some embodiments, the one or more polysaccharide is bonded or printed to a matrix comprising silicons [for example Polydimethylsiloxane (PDMS)] or other surface of microfluidic apparatus to help in the purification of the microvesicles from the sample. In other embodiments, the micro-fluidic apparatus includes downstream molecular analysis such as PCR, identification of protein and/or nucleic acids, etc.

The samples from which microvesicles are isolated may be any sample which contains microvesicles, for example a biological sample. Biological samples include, but are not limited to, whole blood, sputum, seminal fluid, blood serum, plasma, urine, saliva, milk or any other bodily fluid containing microvesicles. Other samples include biopsy from different organs, lymphs, bone marrow and stool samples of subjects and fluid, media or discharges from any organism (unicellular to multicellular, wild or farmed animals or fish) which are pre-cleared before microvesicles isolation.

When the method of isolating microvesicles is used for the diagnosis of a pathological condition, the biological sample is obtained from a subject suffering from the pathological condition. Examples of pathological conditions include, but are not limited to, cancer; infections caused by viruses, bacteria, fungi, protozoa, multicellular organisms, and aberrant proteins such as prions; non-infectious diseases such as autoimmune diseases, heart disease, stroke, asthma, diabetes, chronic kidney disease, osteoporosis, Alzheimer's disease, etc. In one embodiment, the pathological condition is cancer. For example, bodily fluid such as blood is taken from a subject suspected of having cancer and the microvesicles are isolated using method of disclosure and used for early diagnosis. In one embodiment, microvesicles isolated from blood contain biomarkers of vascular disorders, such as heart disease, and therefore, blood is taken from a subject suspected of having a vascular disorder and the microvesicles are isolated using method of disclosure and use for early diagnosis (see Rautou, P., et al., *Circulation*. 2012; 125: 1601-1604; Xiong, J., et al., J Cardiovasc. Pharmacol., 2012 February; 59(2):124-32). In another embodiment, increased levels of microvesicles are observed in certain pathological conditions such as unstable angina, atherosclerosis and inflammatory vascular diseases, and the increase in a sample is detected using a method of the disclosure.

In one embodiment, the methods of the disclosure are used to isolate microvesicles from small sample sizes. In one embodiment, the sample size is from 100 micro-liters to 10 milliliters. In another embodiment, the methods of the disclosure are used for samples using a micro-fluidic apparatus wherein the sample size is between 2 micro-liters to 100 micro-liters.

The isolation of the microvesicles from a sample is performed under conditions for the isolation of the microvesicles. In some embodiments, the conditions include:

(a) contacting the sample with a solution comprising the at least one polysaccharide to form a polysaccharide-microvesicle complex; and (b) separating the polysaccharide-microvesicle complex from the solution.

In some embodiments, the sample is contacted with the polysaccharide(s) for a period of 10 minutes to 20 hours, optimally 10 to 30 minutes or 8 to 12 hours.

In some embodiments, the sample is contacted with the solution at a temperature of 2° C. to 37° C., optionally 2° C. to 10° C. or 20° C. to 25° C.

In other embodiments, the polysaccharide-microvesicle complex is separated by subjecting the solution to centrifugal force or by filtering the solution, or a combination thereof. In some embodiments, the centrifugal force is 3,000 g to 20,000 g, optionally about 17,000 g.

In other embodiments, the polysaccharide-microvesicle complex is washed with saline by subjecting the solution to centrifugal force for 5 minutes to 30 minutes, or optionally about 15 minutes.

In other embodiments, the solution is filtered using a filter with a pore size of 0.45 μm to 2.0 μm to isolate the polysaccharide-microvesicle complex.

In other embodiments of the disclosure, one or more polysaccharide bonded or printed to silicons [for example Polydimethylsiloxane (PDMS)] or other surface of microfluidic apparatus to help in the purification of the microvesicles from the sample.

In other embodiments of the disclosure, the body-fluid-type sample is first treated to prepare the sample for the isolation of the microvesicles. To prepare a cleared sample, for example, after a sample is obtained from a subject, the sample is diluted to 2 to 100 times with physiological saline and subjected to centrifugation at about 17,000 g, or filtered with 0.45 μm to 2.0 μm filter paper, to remove unwanted material from the sample. The cleared sample is then subjected to a method of the disclosure for the isolation of the microvesicles.

(III) Methods of Medical Treatment and Diagnosis

The present disclosure also includes methods of treating and/or diagnosing a pathological condition by administering a polysaccharide described in the disclosure to a subject suffering from the condition. The disclosure also includes methods of diagnosing a pathological condition by the isolation of microvesicles from a biological sample.

Accordingly, in one embodiment, there is included a method for the diagnosis of a pathological condition comprising:

(i) obtaining a biological sample from a subject;
(ii) isolating microvesicles from the sample using a method of the present disclosure;
(iii) measuring an amount of microvesicles in the sample;
(iv) comparing the measured amount of microvesicles with a reference value, and if the amount of microvesicles is increased relative to the reference value, identifying the subject as having an increased probability of having the pathological condition.

The reference value used in the diagnosis can be a standard value known to those skilled in the art, or a value measured from a healthy subject or to monitor the progression or regression of the pathological condition relative to the reference value. For example, the reference value can be calculated from a different subject who does not have the pathological condition, and a comparison of the two reference values provides an indication whether the subject has the pathological condition. Alternatively, the reference value can be calculated from the same patient to monitor the progression or regression of the pathological condition relative to the reference value.

In some embodiments, the pathological condition is cancer. If the amount of microvesicles is increased in the sample relative to the reference value, the subject can subsequently be treated with therapies to treat the condition, or prevent the condition. Alternatively, if the amount of biomarkers in the sample is changed (increased or decreased) relative to the reference value, the subject can subsequently be treated with therapies to treat the condition, or prevent the condition. For example, when the pathological condition is cancer and the diagnosis indicates that the subject suffers from cancer, the subject is treated with chemotherapy, radiological therapy, or any other cancer treatment. Examples of biomarkers include, but are not limited to, metabolites, proteins, peptides, DNA, RNA, mRNA, miRNA, LincRNA, misc-RNA, circular-RNA, etc.

In another embodiment, the disclosure also includes a method for the diagnosis of a pathological condition comprising:
(i) obtaining a biological sample from a subject;
(ii) isolating microvesicles from the sample using a method of the present disclosure; and
(iii) detecting and/or measuring:
(a) one or more pathological markers, and/or markers for a particular tissue or cell-type, wherein the presence of the pathological marker in the sample indicates the presence of the condition in the subject; and/or
(b) one or more healthy normal markers for a particular tissue or cell-type, wherein the absence, or decrease compared to a reference value, of the healthy normal marker in the sample indicates the presence of the pathological condition in the subject. Examples of biomarkers include, but are not limited to, metabolites, proteins, peptides, DNA, RNA, mRNA, miRNA, LincRNA, misc-RNA, circular-RNA, etc.

In one embodiment, there is included a method for the diagnosis of a pathological condition comprising:
(i) obtaining a biological sample from a subject;
(ii) isolating microvesicles from the sample using a method of the present disclosure;
(iii) detecting one or more pathological markers, such as a cancer biomarker, and/or markers for a particular tissue or cell-type, wherein the presence of the pathological marker in the sample indicates the presence of the condition in the subject.

The present disclosure also includes a method of identifying a biomarker associated with a pathological condition, as a result of the biomarker being present in the microvesicle. Accordingly, in one embodiment, the method includes
(i) isolating microvesicles in a biological sample obtained from a subject by using a method of the present disclosure;
(ii) screening the contents of the isolated microvesicles for biomarkers. It will be understood that a biomarker is a molecule that allows for the differential detection of healthy subjects and pathological conditions. For example, in one embodiment, a cancer, or infection specific, mRNA, miRNA, LincRNA, mis-RNA or circular-RNA, protein, peptide, DNA or any other component is detected in isolated microvesicles from subjects having the pathological condition but is not present in the microvesicles of a healthy subject.

In some embodiments, the pathological condition is cancer. Comparing the molecular difference between the samples of a healthy subject and the subject suspected of having for example cancer, for example by the detection of one or more biomarkers for cancer, relative to the reference value, indicates the presence of cancer in the subject, and therefore can subsequently be treated with therapies to treat the condition, or prevent the condition. For example, when the pathological condition is cancer and the diagnosis indicates that the subject suffers from cancer, the subject is treated with chemotherapy, radiological therapy, or any other cancer treatment.

In some embodiments, the pathological condition is an infection (for example infections caused by viruses, bacteria, fungi, protozoa, multicellular organisms, and aberrant proteins known as prions). Comparing the molecular difference between the samples of a healthy subject and the subject suspected of having for example an infection, for example by the detection of one or more biomarkers for the infection, relative to the reference value, indicates the presence of the infection in the subject, and therefore can subsequently be treated with therapies to treat the infection, or prevent an infection. For example, when the pathological condition is bacterial or viral infection and the diagnosis indicates that the subject suffers from infection, the subject is treated with conventional treatment.

In other embodiments of the disclosure, there is also included development of an assay for detecting a pathological condition in a subject, comprising,
(i) obtaining a biological sample from the subject;
(ii) isolating microvesicles from the sample using a method of the present disclosure;
(iii) measuring one or more: (a) biomarkers for the pathological condition, (b) other pathological markers; and/or (c) markers for a particular tissue or cell-type,
(iv) comparing the level of markers defined in step (iii) to a reference value, wherein if the level of markers is increased or decreased relative to the reference value, identifying the subject as having an increased probability of having the pathological condition.

The present disclosure also includes a method for determining if a subject, suffering from a pathological condition, is responsive to a therapy for treatment of the condition, comprising
(i) performing an assay for detecting a pathological condition in a subject as defined above;
(ii) subsequently administering the therapy to the subject;
(iii) performing a second assay as described above in a second biological sample obtained from the subject, wherein a decrease in the level of markers in the second biological sample indicates the subject is responsive to the therapy.

In other embodiments, the pathological condition is cancer.

The present disclosure also includes a method for determining if a subject, suffering from a cancer, is responsive to chemotherapy, radiological therapy, or any other cancer treatment, comprising,
(i) performing an assay for detecting a pathological condition in a subject as defined above, wherein the pathological condition is cancer;
(ii) subsequently administering the chemotherapy, radiological therapy, or any other cancer treatment to the subject;
(iii) performing a second assay as described above in a second biological sample obtained from the subject, wherein a decrease in the level of cancer markers and/or increase in normal healthy biomarkers in the second biological sample indicates the subject is responsive to the therapy.

In other embodiments there is included a method for determining if a subject, suffering from a pathological condition, is responsive to a therapy for treatment of the condition, comprising,
(i) isolating a first amount of microvesicles in a first biological sample obtained from a subject using a method of the present disclosure;
(ii) measuring for one or more markers, such as a cancer biomarker, in the microvesicles from the first biological sample;
(iii) subsequently administering the therapy to the subject;
(iv) isolating a second amount of microvesicles in a second biological sample from the subject using a method of the present disclosure;
(v) measuring for the one or more markers, such as a cancer biomarker, in the microvesicles from the second biological sample,
wherein a difference in the one or more markers, such as a cancer biomarker, in the second amount of microvesicles compared to the values of the first amount of microvesicles in the first biological sample indicates the degree of responsiveness to the therapy in the subject.

In other embodiments, there is also included a method for the treatment of a pathological condition comprising administering to a subject in need thereof a therapeutically effective amount of a polysaccharide to sequester or remove the level of microvesicles associated with the condition in the subject. For example, when the pathological condition is cancer, and subjects suffering from cancer have an increased level of pathological microvesicles or cancer specific microvesicles. Administering one or more polysaccharides or applied as external skin patch in accordance with the present disclosure results in the neutralization of such microvesicles in vivo thereby causing a reduction in the levels of the pathological microvesicles in the subject.

In other embodiments of the disclosure, there is also included an assay for food safety tastings, such as dairy and meat products. Pathogenic, infectious and other disease conditions produce differing profiles of microvesicles. Accordingly, by isolating the microvesicles from the dairy and meat samples using a method of the present disclosure, wherein a differing molecular or physical difference in the dairy and meat sample compared to the control (safe) sample indicates whether the sample meets safety standards for further processing and consumption.

In one embodiment, there is included an assay for detecting a pathological condition in, or contamination of, a food product, comprising:
(i) obtaining a sample from the food product and/or source animal (for example cattle, poultry and pigs);
(ii) isolating microvesicles from the sample using a method of the present disclosure;
(iii) detecting one or more pathological markers, such as a pathogenic, infectious or other disease condition, wherein the presence of the pathological marker in the sample indicates the presence of the condition in the sample.

In one embodiment, there is included an assay for detecting a pathological condition in framed animals, birds and fish, comprising:
(i) obtaining a sample from the source animal (for example cattle, poultry, pigs, fish);
(ii) obtaining a standard non-pathogenic sample from a healthy animal;
(ii) isolating microvesicles from the sample using a method of the present disclosure;
(iii) detecting one or more pathological markers, such as a pathogenic, infectious or other disease condition, wherein the presence of the pathological marker in the sample indicates the presence of the condition in the sample.

For example, in one embodiment, a pathological marker, such as mRNA, miRNA, LincRNA, mis-RNA or circular-RNA, proteins, glycoproteins or other component is detected in isolated microvesicles from samples having the pathological condition but is not present in the microvesicles of a healthy samples.

Although the disclosure has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this disclosure shall not be construed as an admission that such reference is available as prior art to the present disclosure.

EXAMPLES

The operation of the disclosure is illustrated by the following representative examples. As is apparent to those skilled in the art, many of the details of the examples may be changed while still practicing the disclosure described herein.

Materials and Methods

Samples from Cell Lines:

Immortalized normal mammary epithelial cells (MCF-10A), non-aggressive breast cancer cell line (MCF7 and SKBR3) and aggressive breast cancer cell line (MDA-MB-231) were grown in bioreactor (from CELLine, used CEL-Line 1000) in 37° C. with 5% $CO_2$. Thirty million cells were resuspended in 15 ml of microvesicle free FBS (Fetal bovine serum) media. Microvesicle free FBS was prepared by ultra centrifuging FBS at 100,000 to 120,000 g for 2 hours and collecting the FBS without touching the microvesicles pellet. The above cell suspension was used to seed the lower compartment of the bioreactor and 500 ml of the regular media used in the upper compartment. The two compartments separate the bioreactor into a medium and cell compartment by a 10 kDa semi-permeable membrane which allows a continuous diffusion of nutrients into the cell compartment with a concurrent removal of any inhibitory waste product. The microvesicles cannot pass through this membrane and media enriched in cell and cell derived material were harvested regularly from the lower chamber (called conditioned media) with continuous feeding both the chambers. This method was used for the cell lines described in Tables 1-3 and FIGS. 1B, 1C, 2, 4, 6, 7, 8 and 9.

Plasma Samples from Human Subjects:

The clinical samples from subjects were collected as per clinical and ethical approval of Atlantic Cancer Research Institute. The plasma was diluted 5 or 10 times with saline and used for isolation of microvesicles as described in the method of this disclosure. This method was used for the samples shown in FIGS. 1A, 5 and 10.

Isolation of Microvesicles by Ultracentrifugation:

The conditioned media from tissue culture bioreactor were collected and subjected to 17,000 g centrifugation for 15 minutes at 4° C. The 'cleared' supernatant was used for ultra centrifugation. The cleared liquid was overlaid onto 30% sucrose cushion and centrifuged at 100,000 to 120,000 g for two hours. The bottom ring was aspirated using a Pasteur pipette into a new ultracentrifuge tube and diluted 5 to 10 times with PBS (phosphate buffered saline) and centrifuged again at 100,000 to 120,000 g for two hours. The microvesicles pellet were collected and stored for protein and/or RNA isolation. Examples shown in Tables 1-3 and FIGS. 2 and 4, as comparative conventional method of isolating microvesicles.

Atomic Force Microscopy:

Mechanically cleaved Muscovite Mica was used to produce clean, atomically flat surfaces which have strong electrostatic interactions and model substrate for adsorption of biological materials. Microvesicles isolated by method in this disclosure were diluted and spread on to freshly cleaved mica and dried with gentle blow of nitrogen. The microvesicles absorbed mica slides were immediately analyzed for structural studies with Atomic Force Microscopy. Examples shown in FIG. 1C.

Immunofluorescence Microscopy:

The microvesicles were pre-stained with PKH67 (green) followed by co-incubated with new target cells in microvesicle free media for an indicated period followed by immuno-fluorescence staining procedure. The cells were fixed with 3.7% formalin, block with 1% bovine serum albumin and incubated with antibodies (for example Golgin and LAMP-1). The secondary antibody conjugated with Alexa Fluor fluorescent dyes were subsequently incubated on to the cells and nucleus was stained blue with DAPI. The permanently mounted slides were photomicrographed using a confocal microscope. Examples shown in FIGS. 9 and 10.

Transmission Electron Microscopy:

The dispersed microvesicles were deposited onto formvar/carbon-coated EM grids and fixed with 3.7% formalin followed by two washes with PBS and stained with 2% uranyl acetate. The dried grids were then viewed. Examples shown in FIG. 1B.

Nanoparticle Tracking Analysis:

The dispersed microvesicles were diluted to 100 to 1000 times in PBS for this analysis. Nanoparticle tracking analysis was done using LM10 unit and software v2.3 (Nanosight, Amesbury, UK). Hydration-sphere-equivalent sizes are displayed as particle size distribution with their relative abundance. Examples shown in FIG. 1A.

Example 1

Sample Preparation

Conditioned Media from Bioreactor:

As described in the Materials section, conditioned media were regularly harvested for subsequent isolation of microvesicles. The conditioned media was subjected to centrifugation (800 g for 10 minutes at room temperature or 4° C.) to remove the cells and cellular debris. The samples were stored at 4° C. with 15 µl of protease inhibitor cocktail III (from EMD Millipore) in 1 ml of media. The supernatants were then subjected to another round of centrifugation (17,000 g for 15 minutes at 4° C.) to remove finer cellular partials. Examples shown in Table 1-4 and FIGS. 1B, 1C, 2, 4, 6, 7, 8 and 9.

Conditioned Media from Normal Cell Culture:

Cells were grown to 80 to 90% confluency in their respective media. The cells were then rinsed 3 times with serum-free media and incubated at 37° C. for 4 hours. The conditioned media was subjected to centrifugation (800 g for 10 minutes at room temperature or 4° C.) to remove the cells and cellular debris. The samples were stored at 4° C. with 15 µl of protease inhibitor cocktail III (from EMD Millipore) in 1 ml of media. The supernatants were then subjected to another round of centrifugation (17,000 g for 15 minutes at 4° C.) to remove finer cellular partials. Examples shown in FIG. 3.

Sample from Subjects:

Human plasma samples were collected as per clinical procedures and approvals. The plasma samples were archived at −80° C. in 0.5 or 1.0 ml aliquots. The fresh or thawed archived plasma were diluted to 5-10 times in PBS (phosphate buffered saline). The diluted plasma was subjected to centrifugation (1500 g for 10 minutes at room temperature or 4° C.) to remove the cells and cellular debris. The supernatants were stored at 4° C. with 15 µl of protease inhibitor cocktail III (from EMD Millipore) per 1 ml. The supernatants were then subjected to another round of centrifugation (17,000 g for 15 minutes at 4° C.) to remove finer cellular partials or particles formed by globular proteins. Examples shown in FIGS. 1A, 1B, 1C, 5 and 10.

Example 2

Isolation of Microvesicles with Polysaccharide

The cleared samples from Example 1 were then subjected to a hyaluronic acid dextran, dextran sulfate, chondroitin sulfate A, chondroitin sulfate B heparin sulfate.

(i) Long Period Contacting:

20 µg to 100 µg polysaccharide was added into 1 ml of cleared sample and rotated end-to-end overnight at 4° C. (13 to 20 hours). The mixture was subjected to centrifugation (17,000 g for 15 minutes at 4° C.) to precipitate polysaccharide-microvesicles complexes. The palette were transferred to a fresh tube with 1 ml of PBS and again subjected to centrifugation (17,000 g for 15 minutes at 4° C.) to wash. The palette was washed again with PBS and used for different analysis. This method was used for the results shown in the following tables and figures:

Table 1 shows purification/enrichment of microvesicles from conditioned media of Breast cancer cell line MDA-MB-231. The table shows a comparative total proteomic data analysis of isolated microvesicles using hyaluronan, conventional ultracentrifugation (UCF) and a commercially available kit (Exo) from breast cancer cell-line (MDA-MB-231) in an embodiment of a method of the disclosure. The cleared conditioned media was incubated with polysaccharides and enriched microvesicles were analysed to identify the proteins in those microvesicles my mass-spectrometric analysis;

Table 2 shows p-values of cellular component Ontology analysis using proteomic data analysis from Table-1 of isolated microvesicles using polysaccharides (in an embodiment of a method of the disclosure), conventional ultracentrifugation (UCF) and a commercially available kit (Exo) from breast cancer cell-line (MDA-MB-231) in an embodiment of a method of the disclosure;

Table 3 shows a comparative numbers of miRNAs (using next generation sequencing platform) from isolated microvesicles, conventional ultracentrifugation (UCF) and a commercially available kit (Exo) from breast cancer cell-lines (MCF7 and MDA-MB-231) in an embodiment of a method of the disclosure;

Table 4 shows differential protein content of purified/enriched microvesicles from conditioned media of normal breast cell line MCF10A and Breast cancer cell line MCF7. The table shows a percent of the total protein identified by mass spectrometry analysis of isolated microvesicles using hyaluronan, in an embodiment of a method of the disclosure;

FIG. 1A demonstrates that polysaccharides can enrich or purify microvesicles from diluted (in saline) and cleared patients plasma in an embodiment of a method of the disclosure. The figure shows particle size distribution (using nanoparticle tracking analysis) of the isolation of microvesicles from healthy subject and breast cancer patient's plasma.

Figure 1B:
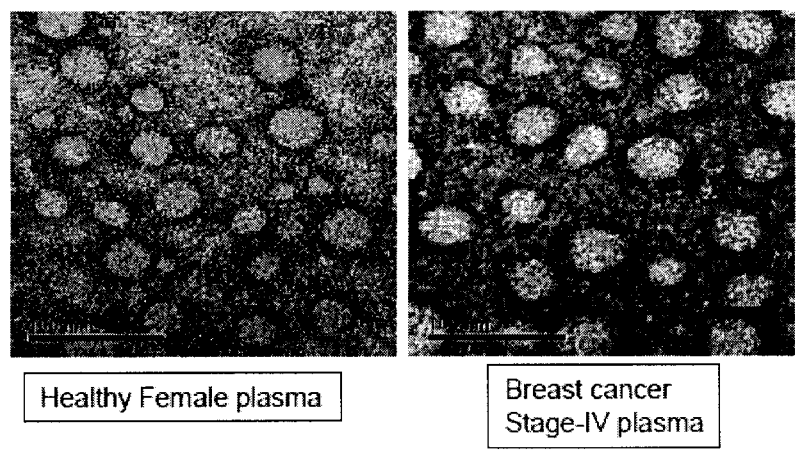
FIG. 1B shows a series of transmission electron micrographs demonstrating the isolation of microvesicles from breast cancer cell-line (MCF10A and MDA-MB-231) conditioned media, plasma of a healthy subject and a breast cancer patient's plasma in an embodiment of a method of the disclosure.
Figure 1B:
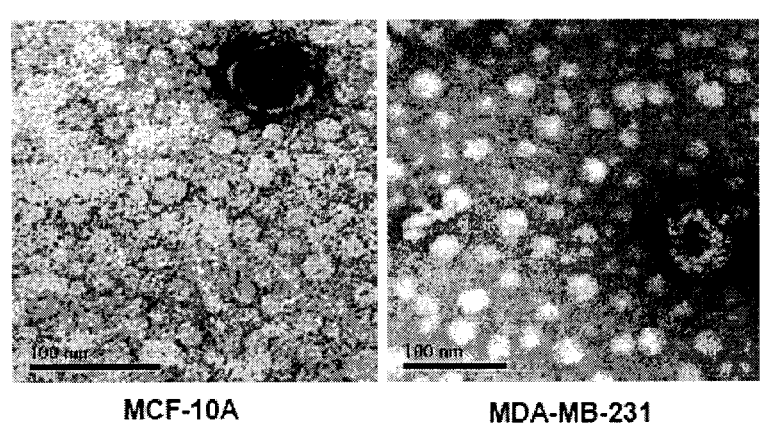

FIG. 1B demonstrates that polysaccharides can enrich or purify microvesicles from diluted (in saline) and cleared patients plasma, in an embodiment of a method of the disclosure. The figure shows transmission electron micrographs demonstrating the isolation of microvesicles from a breast cancer patient's plasma and plasma from healthy.

FIG. 1B also demonstrates enrichment of microvesicles from cell line conditioned media, in an embodiment of a method of the disclosure. The figure shows transmission electron micrographs demonstrating the isolation of microvesicles from a breast cell lines (normal and cancerous).

Figure 1C:
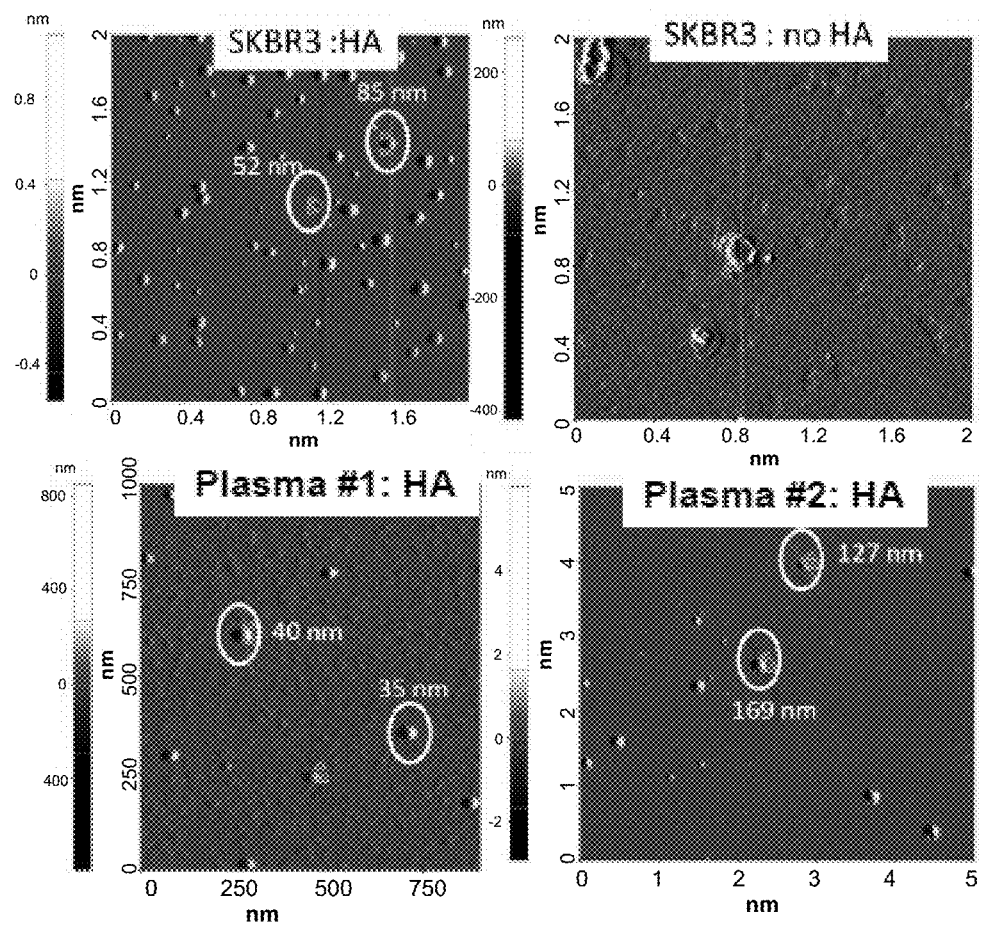
FIG. 1C shows a series of atomic force micrographs demonstrating the isolation of microvesicles from breast cancer cell-line (SKBR3) conditioned media, plasma of a healthy subject and a breast cancer patient's plasma in an embodiment of a method of the disclosure.

FIG. 1C shows the purification/enrichment of microvesicles from conditioned media of Breast cancer cell line SKBR3, in an embodiment of a method of the disclosure. The cleared conditioned media was incubated with polysaccharides and enriched microvesicles were visualized by Atomic Force Microscopy. No microvesicles were enriched where no PS was added. Here the PS used was hyaluronic acid.

FIG. 1C also demonstrates that polysaccharides can enrich or purify microvesicles from diluted (in saline) and cleared patients plasma, in an embodiment of a method of the disclosure. The figure shows atomic force micrographs demonstrating the isolation of microvesicles from a breast cancer patient's plasma and plasma from healthy.

Figure 2:
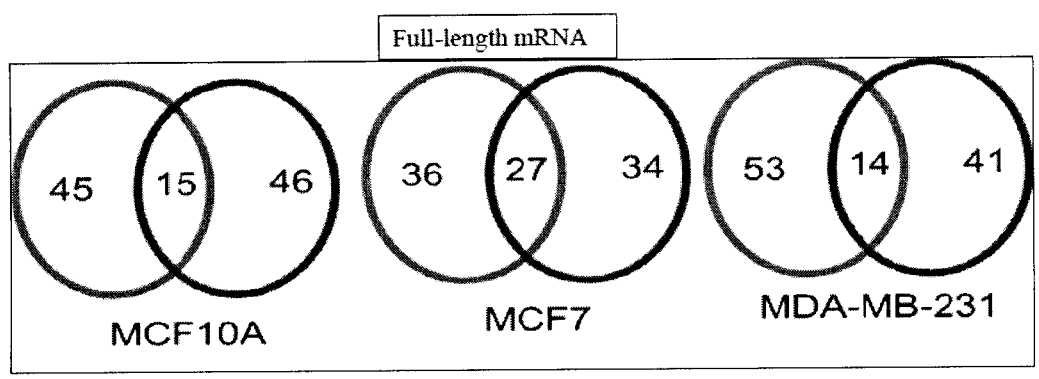
FIG. 2 shows a Venn diagram of numbers of identified intact cellular mRNAs found in microvesicles isolated by both conventional ultracentrifugation and microvesicles isolated using a method of the disclosure.

FIG. 2 shows a Venn diagram with examples of intact cellular mRNAs found in microvesicles isolated by both conventional ultracentrifugation and microvesicles isolated from different breast cancer cell lines (using micro-array analysis), in an embodiment of a method of the disclosure.

Figure 4:
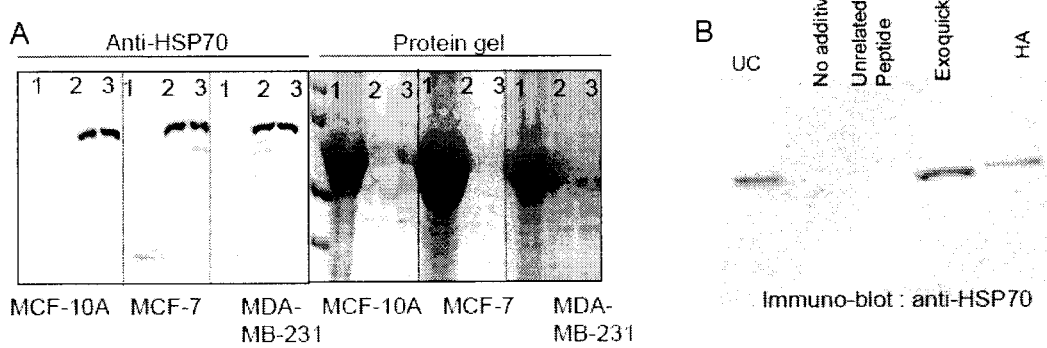
FIG. 4 is an immuno-blot analysis and corresponding Coomassie Blue stained protein polyacrylamide gel electrophoresis photographs demonstrating the detection of heat shock protein-70 in microvesicles isolated using an embodiment of a method of the disclosure.

FIG. 4 shows an immuno-blot analysis of cleared conditioned media from breast cancer cell lines, in an embodiment of a method of the disclosure. Heat shock protein is a marker for microvesicles, which are conserved in enriched microvesicles using the method of the disclosure. Enriched/isolated microvesicles were visualized by Immuno-blotting with Anti-HSP70 antibody (left) and Corresponding protein gel (right). Lane 1 shows 5% of the total conditions media input; lane 2 shows microvesicles enriched by a commercial kit: Exoquick; and lane 3 shows microvesicles isolated by polysaccharides.

Figure 5:
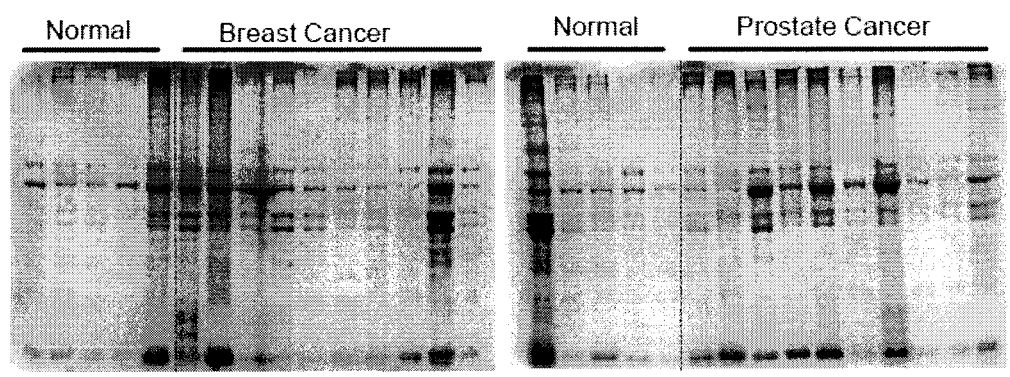
FIG. 5 are a Coomassie Blue stained protein-polyacrylamide gel electrophoresis photographs of total protein content of microvesicles from healthy human plasma, breast cancer and prostate cancer patients' plasma using an embodiment of a method of the disclosure.

FIG. 5 is a Coomassie Blue stained protein-Polyacrylamide gel electrophoresis photographs demonstrating the isolation of microvesicles from breast cancer and prostate cancer patients' plasma, in an embodiment of a method of the disclosure. 50 micro-liter of plasma diluted 10 times with saline was cleared and used to enrich microvesicles. One-third of the total extract was loaded for the protein gel.

Figure 6:
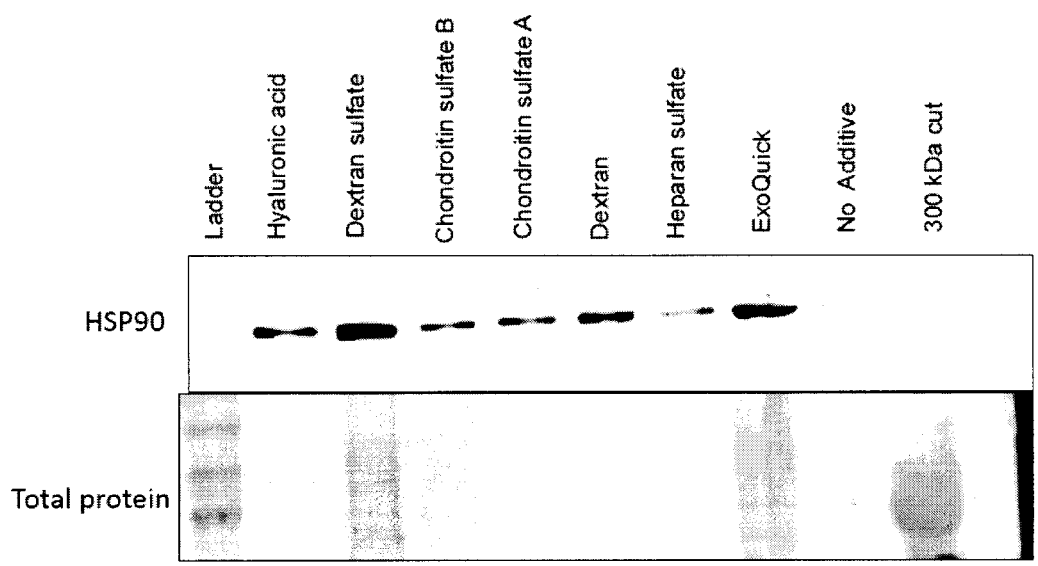
FIG. 6 is an immuno-blot analysis and corresponding stained protein Polyacrylamide gel electrophoresis photographs demonstrating the detection of heat shock protein-90 in microvesicles isolated using an embodiment of a method of the disclosure.

FIG. 6 shows an immuno-blot analysis of cleared conditioned media from breast cancer cell line (MCF7) incubated with different polysaccharides, in an embodiment of a method of the disclosure. Heat shock protein is a marker for microvesicles, which are conserved in enriched microvesicles using the method of the disclosure. Enriched/isolated microvesicles were visualized by Immuno-blotting with Anti-HSP90 antibody (top) and Corresponding total protein gel (bottom).

Figure 7:
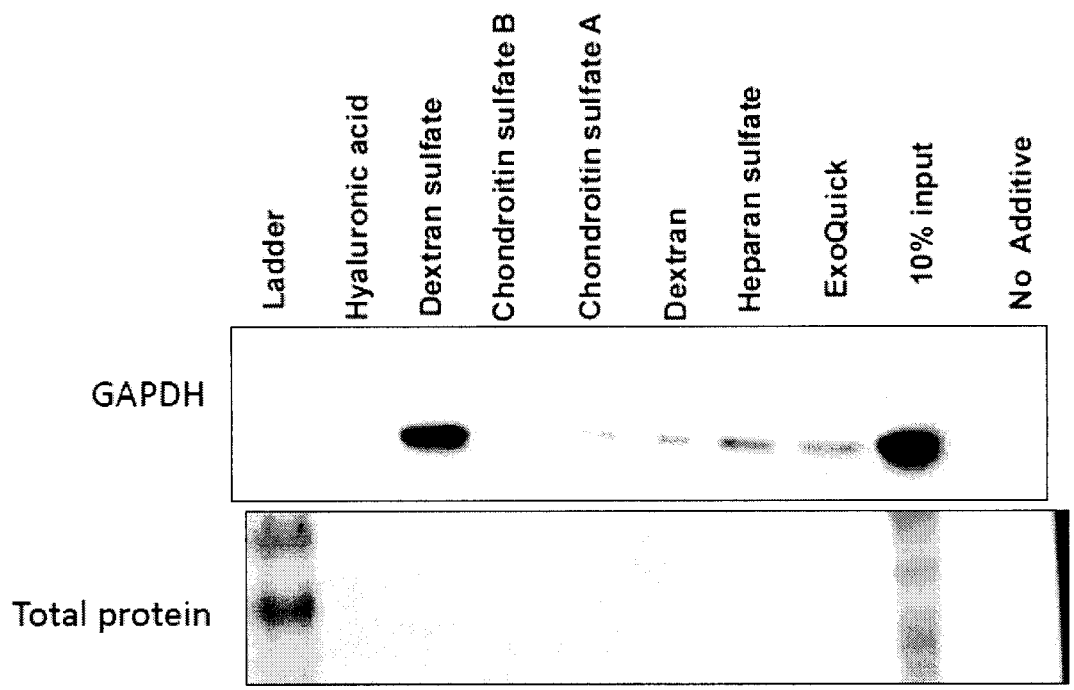
FIG. 7 is an immuno-blot analysis and corresponding stained protein Polyacrylamide gel electrophoresis photographs demonstrating the detection of glyceraldehyde 3-phosphate dehydrogenase (GAPDH) in microvesicles isolated using an embodiment of a method of the disclosure.

(ii) Short Period Contacting:

Twenty to 100 µg/ml of polysaccharides were added into 1 ml of cleared sample and mixed by inverting end-to-end for 20 times and incubated at 37° C. or room temperature for 10 to 30 minutes. The mixture was subjected to centrifugation (17,000 g for 15 minutes at room temperature) to precipitate polysaccharide-microvesicles complexes. The palette were transferred to a fresh tube with 1 ml of PBS and again subjected to centrifugation (17,000 g for 15 minutes at room temperature) to wash. The palette was washed again with PBS and used for analysis. This method was used for the results shown in the following figures:

FIG. 7 shows an immuno-blot analysis of cleared conditioned media from breast cancer cell line (MCF7) and enriched microvesicles in an embodiment of a method of the disclosure. Enriched/isolated microvesicles using different polysaccharides were analysed by Immuno-blotting with Anti-Glyceraldehyde 3-phosphate dehydrogenase antibody (top) and corresponding total protein gel (bottom).

Figure 8:
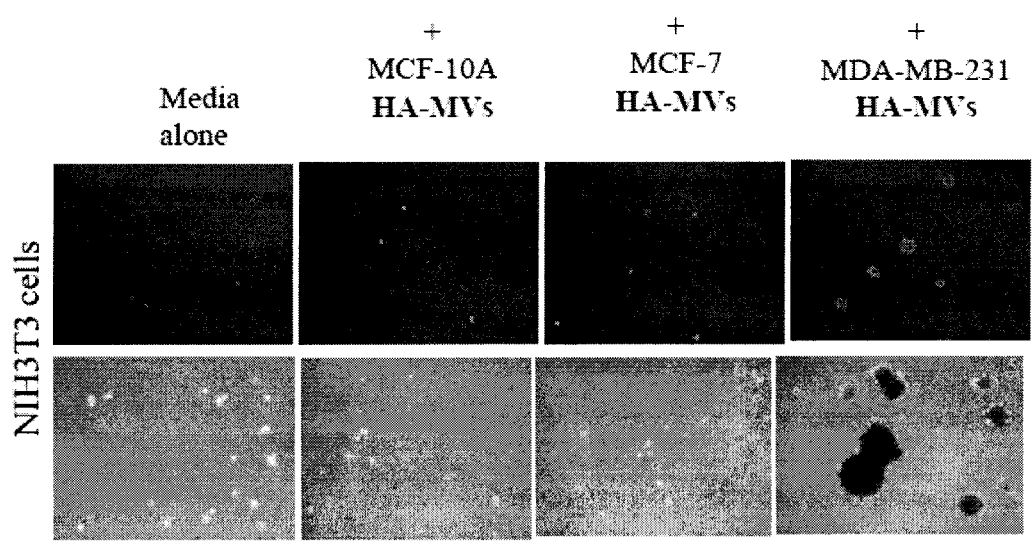
FIG. 8 is a malignant transformation assay using non-transformed mouse fibroblasts in soft agar demonstrating that microvesicles isolated using polysaccharides in an embodiment of a method of the disclosure from normal (MCF10A), less aggressive (MCF7) and more aggressive (MDA-MB-231) have differential capabilities of transforming a normal cell to cancerous cell.
Figure 9:
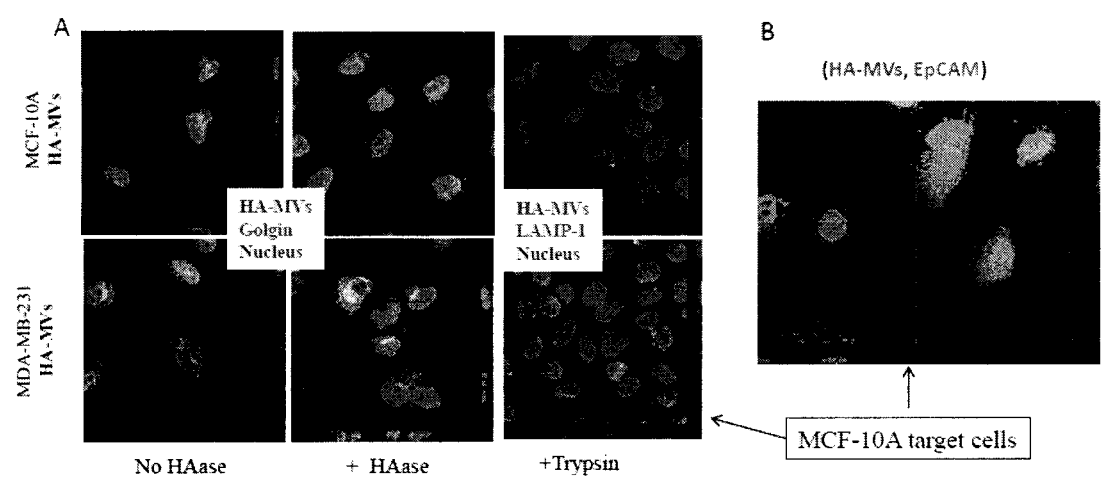
FIG. 9 are immunofluorescence micrographs showing internalization of microvesicles (isolated from conditioned media of breast cell lines MCF10A and MDA-MB-231) using a method of the disclosure into normal breast host cells (MCF-10A)

FIG. 8 is a malignant transformation assay using non-transformed mouse fibroblasts in soft agar demonstrating that isolated microvesicles from normal (MCF10A), less aggressive (MCF7) and more aggressive (MDA-MB-231) cell lines, in an embodiment of a method of the disclosure. The isolated microvesicles have differential capabilities of transforming a normal cell to cancerous cell. NIH3T3 cells are non-transformed fibroblast mice cells and make colonies in soft-agar when they are induced to oncogenic transformation. Microvesicles from conditioned media were for 3 times and let grow for 18 days. Microvesicles free defined stem-cell media was used for all experiments. Out of the three breast cancer cell lines, MDA-MB-231 is the most aggressive and has metastatic potential. Isolated microvesicles conserved their transformation potential, and therefore, the degree of cancer aggressiveness could be measured with the method of the disclosure.

Example 3

Biotin Avidin System

Figure 3A:
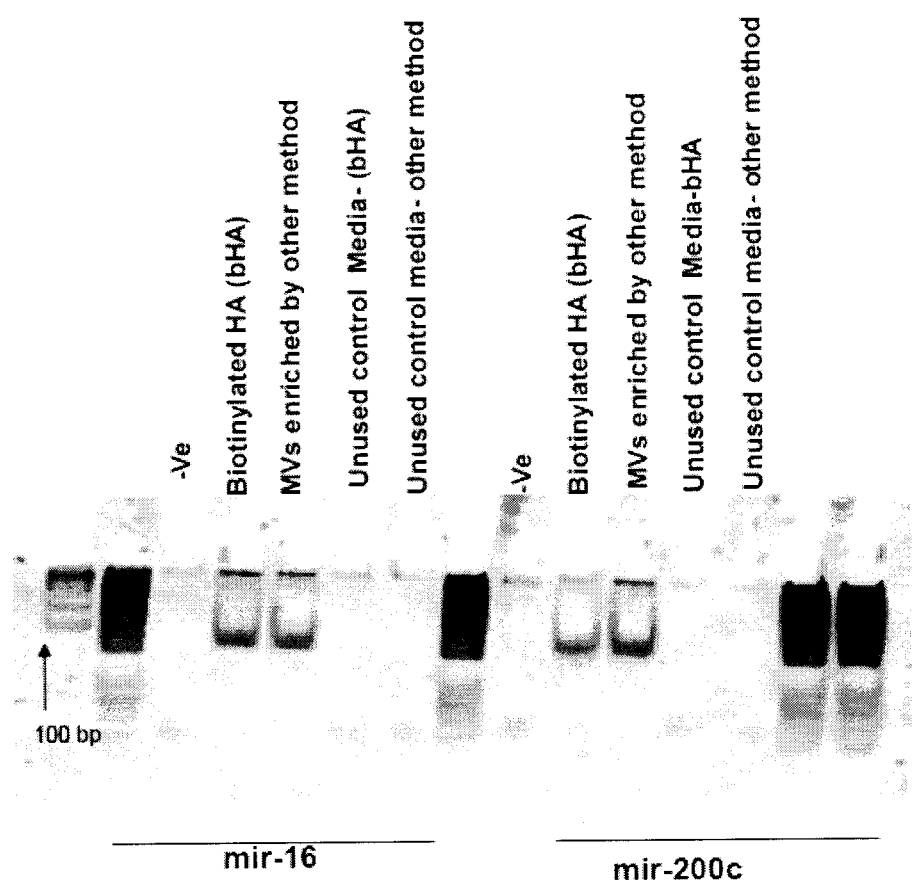
FIG. 3A is a Polyacrylamide gel electrophoresis photograph demonstrating the detection of micro-RNA from microvesicles isolated using an embodiment of a method of the disclosure.
Figure 3B:
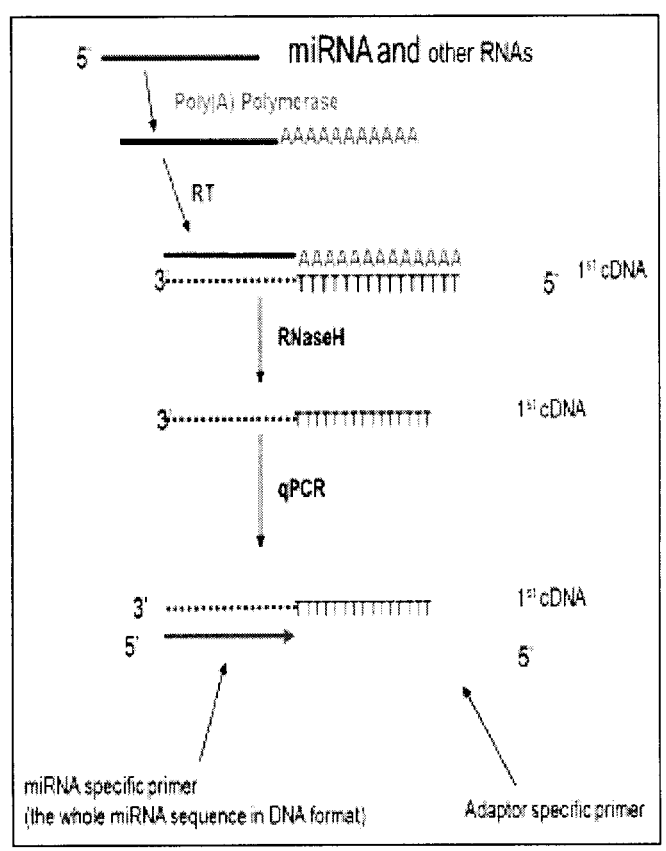
FIG. 3B (insert) is a flow diagram of the molecular biological techniques followed for the detection of miRNAs.

Biotinylated Hyaluronic acid (bHA) was prepared following published protocol[15]. Conditioned media from normal cell culture were used. The cleared media were incubated with bHA (1 µg/ml of media) and rotated end-to-end overnight at 4° C. The mixture was incubated with 20 µl of Dynabeads MyOne Streptavidin C1 (Life Technology) and washed 3 times with PBS in separate tubes on magnetic stand. These beads-bHA-microvesicles complex were used to isolate miRNAs/small RNAs using mirPremier microRNA Isolation Kit (Sigma) and subjected to PCR identification of specific miRNA using protocol described in FIG. 3B. FIG. 3 is an micro-RNA analysis to demonstrate identification of indicated miRNAs were done from biotinylated polysaccharide-microvesicles complexes using the indicated molecular analysis, in an embodiment of a method of the disclosure. In this Figure, the hyaluronic acid was Biotinylated and captured by Avidin-beads.

Example 4

RNA Purification from Isolated Microvesicles and Microarray Analysis

The RNA was prepared combining Trizol (Invitrogen) and Qiagen RNeasy kit according to the manufacturers' protocol. Isolated microvesicles according to this disclosure were suspended in Trizol and stored at −80° C. until RNA was isolated. For RNA isolation the frozen microvesicles+Trizol tubes were thawed and 200 µl chloroform was added per ml Trizol used. The tubes were shaken vigorously for 20 sec, then allowed to sit at room temperature for 2-3 min, span at 12,000×g for 15 min at 4 C and carefully removed aqueous phase (top) and transfer to new sterile RNase-free tube (1.5 ml tube) for Qiagen RNeasy kit. The total RNA isolated from microvesicles were used to amplify mRNAs only and subsequently those cDNAs were labeled with Amino Allyl Message Amp ii aRNA Kit from Ambion with both Alexa Fluor 555 and Alexa Fluor 647 for each samples (from Invitrogen). The microarray used for these experiments were printed by Atlantic Microarray Facility with 38,000 spots per slide representing protein coding sequences of entire human genome. Hybridization was performed using Tecan Hyb station. Scanning and analysis were done with Axon GenePix4000B scanner and Acuity 4.0 software respectively. Examples shown in FIG. 2.

Example 5

Mass Spectrometry (MS) Analysis Isolated Microvesicles by In-Gel Digestion

Microvesicles were isolated from cell culture conditioned media; in an embodiment of a method of the disclosure Total microvesicles were boiled in 4× lamilli buffer and run on SDS-PAGE. The gel was stained with standard Coomassie Brilliant Blue. The destained gel was cut in 12 equal pieces per lane from top to bottom of the gel in clean hood and collected individually. The gel-pieces were dehydrated using 100% acetonitrile, treated with reducing agent (dithiothreitol), followed by treatment with iodoacetic acid and digested with trypsin over-night. The digested peptides were extracted in 50% acetonitrile/50% acetic acid and evaporated in vacuum centrifuge. The evaporated samples were adjusted to 1% acetic acid for loading in MS.

The protein identification platform consists of an Ultimate 3000 nano-liquid chromatograph (Dionex, Sunnyvale, Calif.) coupled to a linear quadrupole ion trap mass spectrometer (Thermo-Fisher, San Jose, Calif.) via a nanoelectrospray emitter. Small chromatography columns (75 µm×10.5 cm) are packed with 5 um particles into a commercial nanospray tip (New Objective, Woburn, Mass.) with a 15 um spray tip. Typically 15 microliters of peptide extracts are loaded onto a short C18 trap column at 20 µL/min and then eluted with a water/acetonitrile solvent gradient through a second (analytical) C18 column at a flow rate of 400 nL/min. During the chromatographic elution, the mass spectrometer is operated in "data-dependent acquisition" (i.e., DDA) mode whereby the mass spectrometer collects a first order mass spectrum and uses software to target the five most abundant ions in the spectrum for sequencing by collision induced dissociation (CID). Once a peptide mass has been selected for fragmentation twice, dynamic exclusion of the intact peptide mass is implemented for a duration of 30 seconds. Following a 70 minute chromatographic run per sample, the data is submitted to Bioworks for peptide matching and ultimately protein identification. Bioworks uses the Sequest algorithm to match the acquired peptide mass and fragmentation spectra to an "in silico" tryptic digest of the public NCBI non-redundant protein database. The results from the Sequest search are further processed using Scaffold for statistical analysis. Example shown in Table 1, 2 and 4.

Example 6

Western Blots

The protein samples isolated from microvesicles and other sources were boiled for 10 minutes and loaded on SDS-PAGE. The gel was transferred onto nitrocellulose membranes and was blocked for 1-2 h in 10% milk in PBS plus 0.1% Tween 20 (PBS-T), treated with primary antibody overnight at 4° C. in the blocking solution, washed three times with PBS-T, and finally incubated with horseradish peroxidase-conjugated secondary antibodies. The image was developed using a luminol-based chemiluminescence reaction and photographed. Example shown in FIGS. 4, 6 and 7.

Example 7

Detection of miRNAs from Purified Microvesicles

Conditioned media from breast cancer cell line MCF-7 was used for purification of microvesicles with Biotinylated polysaccharides with avidin-beads according to an embodiment of a method of the disclosure. Small RNAs from microvesicles was isolated using Sigma miRNA kit and was polyadenylated with Poly(A) Polymerase and Reverse transcribed using poly-T-adapter primers with reverse transcriptase. The resulted cDNAs of miRNA was PCR amplified with one universal primer (specific to the adaptor) and a forward miRNA specific primer and visualized by Polyacrylamide gel electrophoresis. Examples shown in FIG. 3.

Example 8

Anchorage-Independent Transformation by Microvesicles Derived from Different Breast Cancer Cell-Lines mouse non-transformed fibroblast NIH3T3 cells were used to determine transformation induced cellular growth in semisolid medium. This assay indicate whether any stimuli, genetic and/or epigenetic changes applied to these cells transform them to cancerous cells and thus acquire anchorage-independent growth behavior in semisolid medium like agar. Low melting agarose (Invitrogen) was autoclaved in water at 1.2% (WN) and kept at 40° C. in a water bath. Medium of 2× concentration was preheated in the same bath. In a 12-well plate, 0.5 ml/well agarose/medium mixture in 1:1 (0.6% agarose final) was layered and left to solidify at room temperature for 40 min. Microvesicles isolated using method describe in this disclosure from 1 ml of conditioned media from different cell lines were incubated with 0.25 ml of media with $10^4$ NIH3T3 cells for 30 min at 37° C. followed by mixing that with 0.6% agarose media and layered onto solidified 0.6% agarose layer and kept at room temperature for 1 hour. The semisolid medium with cells and microvesicles were overlaid with 1 ml of medium and incubated at 37° C. for 3 weeks, changing overlaying medium with same amount of media with microvesicles isolated from indicated cells at every $3^{rd}$ days for 3 times and photographed them on $18^{th}$ day. Example shown in FIG. 8.

Example 9

Isolation of Microvesicles from Breast Cancer Sample

Microvesicles were isolated according to an embodiment of a method of the disclosure. Patients plasma (25 µl) was diluted 10 times with PBS (or 0.5 ml of conditioned media) and cleared either by spinning at 17,000 g at 4° C. for 15 minutes or by 0.22 µm filters. The cleared plasma samples were incubated with hyaluronan (100 µg per ml of sample) either for 1 hour at room temperate or 4° C. overnight with end-to-end oration. The microvesicles were pelleted spinning at 17,000 g at 4° C. for 15 minutes followed by two washes with PBS. The pellets were digested with 0.1 µg of hyaluronidases (HAase) for overnight followed by proteaseK digestion for 2 hours at 37° C. to disperse to individual microvesicles for nanoparticle tracking analysis (NTA), transmission electron microscopy (TEM) and atomic force microscopy (AFM) as shown in FIGS. 1A, 1B and 1C. NTA profiles of microvesicles shows a major peak representing the mode size and the bar scales of the TEM are 100 nm. The diameter of each MV circled (white) are presented for the AFM. The sizes of the microvesicles are comparable to published data.

Example 10

Comparative Proteomic Analysis of Breast Cancer Microvesicles from MDA-MB-231 Breast Cancer Cell Line Shown in Table 1 is a proteomic analysis of breast cancer microvescles with different isolation methods from indicated breast cancer cell line conditioned media. The isolation methods are as follows: conventional ultracentrifugation method (UCF), with hyaluronan (HA) in accordance with the present disclosure, and commercially available ExoQuick (Exo). Representative proteomic data of microvesicles extracted from MDA-MB-231 with different methods are shown here. The number of unique peptides from a protein are indicated in this table.

Table 2 shows a Gene Ontology analysis of the proteins of Table 1 to associate the cellular components using ToppGene Suite. Table 2 indicatesthe p-value for the specific cellular vesicles. Proteomic data of microvesicles extracted from MDA-MB-231 conditioned media obtained from Table-1 using the indicated methods were used for cellular component Ontology analysis. The proteomic data was extracted for 100% protein identification probability for Ontology analysis. Conventional ultracentrifugation method (UCF), hyaluronan (HA), commercially available ExoQuick (Kit) and Vn96 were compared here. The p-value indicates the statistical significance of the proteome of microvesicles extracted using different methods. The highly significant cellular components indicate the 'proteomes' were originated from extracellular microvesicles or exosomes.

Table 4 shows differential protein content of purified/enriched microvesicles from conditioned media of normal breast cell line MCF10A and Breast cancer cell line MCF7. The table shows a percent of the total protein identified by mass spectrometry analysis of isolated microvesicles using hyaluronan, in an embodiment of a method of the disclosure;

Example 11

Comparative Transcriptomics Analysis of Breast Cancer Hyaluronan-Microvesicles Complexes Comparison of microvesicle isolation methods from indicated breast cancer cell line conditioned media: ultracentrifugation method with hyaluronan (HA), according to an embodiment of a method of the disclosure. Total RNA from indicated microvesicles was isolated and subjected to cDNA microarray analysis (38K Human Oligo microarray, Atlantic Microarray Facility). The numbers of full-length mRNAs are shown in Venn diagram of FIG. 2.

Comparison of microvesicle isolation methods from indicated breast cancer cell lines' conditioned media: ultracentrifugation and hyaluronan (HA) methods: miRNA sequences from microvesicles isolated from 2 different breast cancer cell lines (MCF7 and MDA-MB-231) using ultracentrifugation (UCF), a commercial kit (Exo) and method of the disclosure using Hyaluronan (HA). The sequencing were performed using ion-torrent platform of next-generation sequencing and aligned the reads on human genome Hg19 according to their size and miRNAa were identified using either human precursor miRNA annotation (mirBase V19), or human transcripts Hg19. The numbers shown in Table 3 represent number of 'reads' or match with the particular miRNA sequence in the samples.

Example 12

Enrichment of Microvesicles from Conditioned Media Using Different Polysaccharides 1.5 ml of conditioned media from breast cancer cell line MCF7 was cleared from cellular debris by centrifugation at 5000×g for 10 minutes followed by filtration through 0.2 μm syringe filters. 100 μg/ml of each indicated polysaccharide, according to an embodiment of a method of the disclosure, as shown in FIG. 6 was mixed with the conditioned media and incubated overnight with end-to-end rotation. The mixture was centrifuged at 17,000×g for 15 minutes at 4° C. The precipitates were washed 3 times with PBS. The right most lane: 300 kDa cut demonstrates a spin-filter was used to remove any proteins less than 300 kDa. For all experiments, low protein binding plastic-ware was used. The precipitates were subjected to Western blot analysis for HSP90 as shown in FIG. 6, an abundant marker of extracellular microvescicles or exosomes, clearly demonstrating isolation of the microvesicles.

Example 13

Enrichment of Microvesicles from Conditioned Media Using Different Polysaccharides 1.5 ml of conditioned media from breast cancer cell line MCF7 was cleared from cellular debris by centrifugation at 5000×g for 10 minutes followed by filtration through 0.2 μm syringe filters. 66 μg/ml of each indicated polysaccharide, according to an embodiment of a method of the disclosure, as shown in FIG. 7 was mixed with the conditioned media and incubated 25° C. with end-to-end rotation for 30 minutes. The mixture were centrifuged at 17,000×g for 15 minutes at 25° C. The precipitates were washed 3 times with PBS. For all experiments, low protein binding plastic-ware were used. The Precipitates were subjected to Western blot analysis for glyceraldehyde 3-phosphate dehydrogenase (GAPDH) as shown in FIG. 7, an abundant marker of extracellular microvescicles or exosomes.

Example 14

Biologically Active Microvesicles—Soft-Agar Anchorage-Independent Growth Assay with NIH/3T3 Cells NIH/3T3 cells are murine non-transformed fibroblasts which make colonies in soft-agar only when they are induced to oncogenic transformation. Microvesicles isolated in accordance with the above examples using hyaluronan (HA) from indicated cells (according to an embodiment of a method of the disclosure) were added onto target NIH/3T3 cells in soft-agar every 3rd day for 3 times and grown for 18 days (top panel), as shown in FIG. 8. Defined Stem cell media was used as MV free medium. The cell-embedded soft-agar (top panel) were pulverized with 1 ml pipette-tips and further inoculated in soft-agar, without any newly added microvesicles (in Stem cell medium) for 3 weeks (lower panel of FIG. 8). The results indicated that the more invasive breast cancer line (MDA-MB-231) derived Hyaluronan-Microvesicles transformed NIH/3T3 cells permanently (colonies) and can form colonies on soft-agar even after 40 days.

Example 15

Biologically Active Microvesicles Internalized into Host Cell

Internalization Assay:

(A) Hyaluronan-microvesicles complex (HA-MVs) isolated from indicated breast cancer cell-lines' conditioned media using hyaluronan (HA), according to an embodiment of a method of the disclosure, as shown in FIG. 9A, were treated with or without hyaluronidases (HAase) or trypsin. The pre-stained HA-MVs co-incubated with target MCF-10A cells in MV free media for 48 hours followed by immuno-fluorescence microscopy. HAase treatment did not show any difference in internalization but significantly reduced for trypsinized HA-MVs derived from MCF-10A cells in comparison to the HA-MVs from MDA-MB-231 cells. Golgin is a marker for Golgi body and LAMP-1 is a marker for lysosome and exocytosis pathways. As shown in FIG. 9B, a similar internalization assay was performed as in (A) where HA-MVs were co-incubated with MCF-10A target cells for almost 100 hours. A network of green membrane tubules originating from HA extracted microvesicles' PKH67 (green) stained lipid (resembling endoplasmic reticulum, ER) were observed, which indicates that the microvesicles were internalized and also integrated into components of cytoplasm (EpCAM is cell surface marker).

Example 16

Biologically Active Microvesicles Internalized into Human Host Cell

Figure 10:
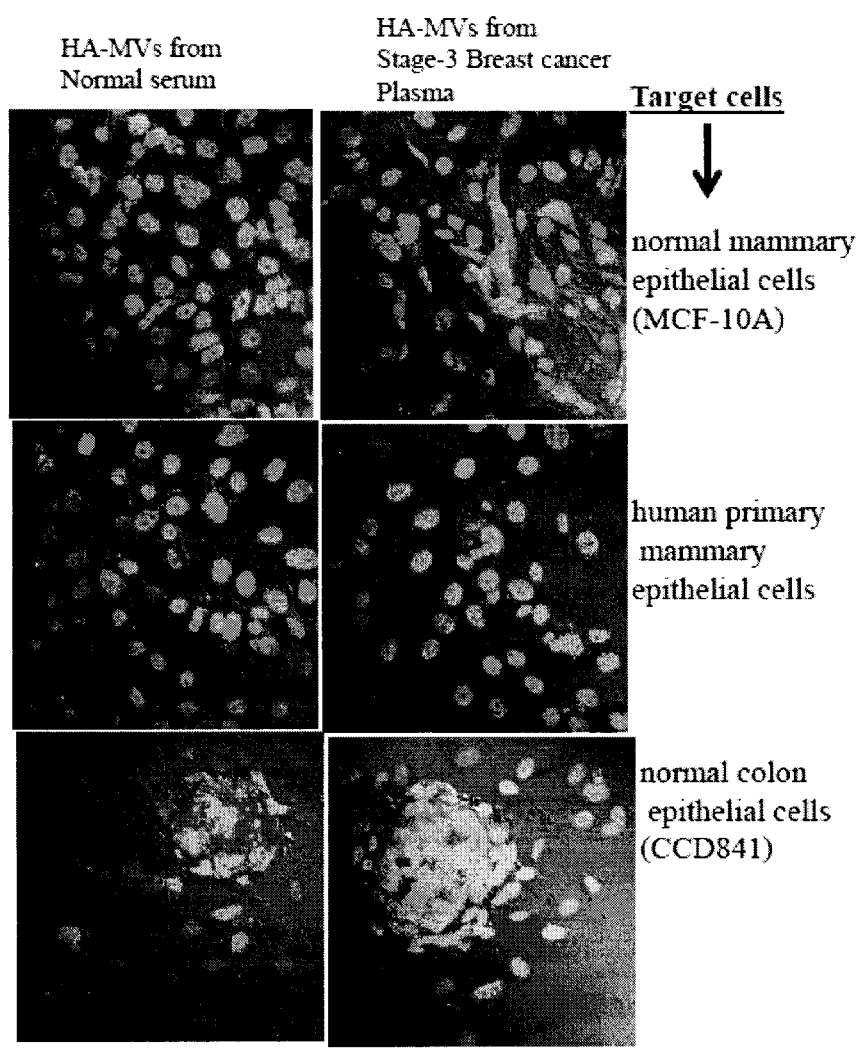
FIG. 10 are immunofluorescence micrographs showing internalization of microvesicles isolated from normal subject's and breast cancer patient's plasma using a method of the disclosure into normal host cells of different tissue of origin.

A similar internalization assay was performed as in Example 15 where HA-MVs from indicated plasma from subjects (as shown in FIG. 10) with or without breast cancer were isolated using hyaluronan (HA), according to an embodiment of a method of the disclosure. The lipids were stained with PKH67 (green) and co-incubated with indicated target cells for 48 hours. We used 25 μl of plasma dilute 10 times with PBS and then subjected to hyaluronan mediated MV precipitation. One tenth of the total extracted HA-MVs were co-incubated with target cells. FIG. 10 shows that the microvesicles were internalized into the cells.

TABLE 1

Comparative Proteomic Analysis of Isolated Breast Cancer Microvesicles

| # | Identified Proteins (530) | Number of unique peptides | | |
|---|---|---|---|---|
| | | UCF | HA | EXO |
| 1 | Serum albumin OS = *Bos taurus* GN = ALB PE = 1 SV = 4 | 32 | 23 | 58 |
| 2 | Trypsin OS = *Sus scrofa* PE = 1 SV = 1 | 10 | 11 | 13 |
| 3 | Fibronectin OS = *Homo sapiens* GN = FN1 PE = 1 SV = 4 | 42 | 57 | 186 |
| 4 | Galectin-3-binding protein OS = *Homo sapiens* GN = LGALS3BP PE = 1 SV = 1 | 35 | 9 | 30 |
| 5 | Actin-5C OS = *Drosophila melanogaster* GN = Act5C PE = 1 SV = 4 | 16 | 13 | 19 |
| 6 | Keratin, type II cytoskeletal 8 OS = *Homo sapiens* GN = KRT8 PE = 1 SV = 7 | 0 | 0 | 0 |
| 7 | Histone H2A type 1-D OS = *Homo sapiens* GN = HIST1H2AD PE = 1 SV = 2 | 3 | 3 | 20 |
| 8 | Alpha-2-macroglobulin OS = *Bos taurus* GN = A2M PE = 1 SV = 2 | 32 | 0 | 0 |
| 9 | Alpha-enolase OS = *Homo sapiens* GN = ENO1 PE = 1 SV = 2 | 10 | 18 | 23 |
| 10 | Vitamin D-binding protein OS = *Bos taurus* GN = GC PE = 2 SV = 1 | 0 | 0 | 0 |
| 11 | Pyruvate kinase isozymes M1/M2 OS = *Homo sapiens* GN = PKM PE = 1 SV = 4 | 5 | 10 | 15 |
| 12 | Heat shock protein HSP 90-alpha OS = *Bos taurus* GN = HSP90AA1 PE = 2 SV = 3 | 0 | 4 | 8 |
| 13 | Glyceraldehyde-3-phosphate dehydrogenase OS = *Homo sapiens* GN = GAPDH PE = 1 SV = 3 | 5 | 4 | 16 |
| 14 | Keratin, type I cytoskeletal 18 OS = *Homo sapiens* GN = KRT18 PE = 1 SV = 2 | 0 | 0 | 0 |
| 15 | Keratin, type II cytoskeletal 1 OS = *Homo sapiens* GN = KRT1 PE = 1 SV = 6 | 5 | 10 | 7 |
| 16 | Keratin, type I cytoskeletal 19 OS = *Homo sapiens* GN = KRT19 PE = 1 SV = 4 | 0 | 0 | 0 |
| 17 | Phosphoglycerate kinase 1 OS = *Homo sapiens* GN = PGK1 PE = 1 SV = 3 | 6 | 15 | 20 |
| 18 | Keratin, type II cytoskeletal 5 OS = *Homo sapiens* GN = KRT5 PE = 1 SV = 3 | 0 | 0 | 0 |
| 19 | L-lactate dehydrogenase A chain OS = *Homo sapiens* GN = LDHA PE = 1 SV = 2 | 5 | 8 | 10 |
| 20 | Alpha-2-HS-glycoprotein OS = *Bos taurus* GN = AHSG PE = 1 SV = 2 | 5 | 4 | 4 |
| 21 | Vimentin OS = *Pan troglodytes* GN = VIM PE = 2 SV = 4 | 0 | 17 | 16 |
| 22 | Filamin-A OS = *Homo sapiens* GN = FLNA PE = 1 SV = 4 | 0 | 0 | 0 |
| 23 | Transforming growth factor-beta-induced protein ig-h3 OS = *Homo sapiens* GN = TGFBI PE = 1 SV = 1 | 0 | 0 | 0 |
| 24 | Filamin-B OS = *Homo sapiens* GN = FLNB PE = 1 SV = 2 | 9 | 2 | 4 |
| 25 | Keratin, type I cytoskeletal 10 OS = *Homo sapiens* GN = KRT10 PE = 1 SV = 6 | 5 | 7 | 4 |
| 26 | Alpha-1-antiproteinase OS = *Bos taurus* GN = SERPINA1 PE = 1 SV = 1 | 4 | 0 | 0 |
| 27 | Annexin A2 OS = *Homo sapiens* GN = ANXA2 PE = 1 SV = 2 | 13 | 19 | 11 |
| 28 | Thrombospondin-1 OS = *Homo sapiens* GN = THBS1 PE = 1 SV = 2 | 0 | 0 | 21 |
| 29 | Histone H2B type 1-C/E/F/G/I OS = *Homo sapiens* GN = HIST1H2BC PE = 1 SV = 4 | 2 | 0 | 13 |
| 30 | Heat shock protein HSP 90-beta OS = *Equus caballus* GN = HSP90AB1 PE = 2 SV = 3 | 0 | 0 | 7 |
| 31 | Tubulin alpha-1A chain OS = *Cricetulus griseus* GN = TUBA1A PE = 2 SV = 1 | 4 | 9 | 7 |
| 32 | Cathepsin D OS = *Homo sapiens* GN = CTSD PE = 1 SV = 1 | 0 | 0 | 8 |
| 33 | Ubiquitin-60S ribosomal protein L40 OS = *Bos taurus* GN = UBA52 PE = 1 SV = 2 | 6 | 3 | 0 |
| 34 | Laminin subunit gamma-2 OS = *Homo sapiens* GN = LAMC2 PE = 1 SV = 2 | 0 | 0 | 0 |
| 35 | Heat shock cognate 71 kDa protein OS = *Bos taurus* GN = HSPA8 PE = 1 SV = 2 | 2 | 0 | 7 |
| 36 | Tubulin beta-1 chain OS = *Gadus morhua* PE = 2 SV = 1 | 0 | 5 | 7 |
| 37 | Fatty acid synthase OS = *Homo sapiens* GN = FASN PE = 1 SV = 3 | 0 | 0 | 0 |

TABLE 1-continued

Comparative Proteomic Analysis of Isolated Breast Cancer Microvesicles

| # | Identified Proteins (530) | UCF | HA | EXO |
|---|---|---|---|---|
| 38 | Actin-18 OS = *Dictyostelium discoideum* GN = act18 PE = 3 SV = 3 | 0 | 0 | 0 |
| 39 | Peptidyl-prolyl cis-trans isomerase A OS = *Chlorocebus aethiops* GN = PPIA PE = 2 SV = 2 | 0 | 8 | 7 |
| 40 | Amyloid beta A4 protein OS = *Homo sapiens* GN = APP PE = 1 SV = 3 | 0 | 0 | 0 |
| 41 | Transitional endoplasmic reticulum ATPase OS = *Homo sapiens* GN = VCP PE = 1 SV = 4 | 0 | 0 | 15 |
| 42 | 14-3-3 protein sigma OS = *Homo sapiens* GN = SFN PE = 1 SV = 1 | 0 | 0 | 0 |
| 43 | Integrin beta-1 OS = *Homo sapiens* GN = ITGB1 PE = 1 SV = 2 | 17 | 7 | 0 |
| 44 | Collagen alpha-1(VI) chain OS = *Homo sapiens* GN = COL6A1 PE = 1 SV = 3 | 0 | 3 | 24 |
| 45 | Heat shock protein beta-1 OS = *Homo sapiens* GN = HSPB1 PE = 1 SV = 2 | 0 | 0 | 0 |
| 46 | Keratin, type I cytoskeletal 9 OS = *Homo sapiens* GN = KRT9 PE = 1 SV = 3 | 0 | 0 | 0 |
| 47 | Elongation factor 2 OS = *Callithrix jacchus* GN = EEF2 PE = 2 SV = 1 | 0 | 0 | 4 |
| 48 | Keratin, type II cytoskeletal 6A OS = *Homo sapiens* GN = KRT6A PE = 1 SV = 3 | 0 | 0 | 0 |
| 49 | Heat shock 70 kDa protein 1A/1B OS = *Homo sapiens* GN = HSPA1A PE = 1 SV = 5 | 0 | 0 | 4 |
| 50 | Nucleobindin-1 OS = *Homo sapiens* GN = NUCB1 PE = 1 SV = 4 | 0 | 0 | 0 |
| 51 | 14-3-3 protein zeta/delta OS = *Bos taurus* GN = YWHAZ PE = 1 SV = 1 | 0 | 4 | 6 |
| 52 | Cystatin-S OS = *Homo sapiens* GN = CST4 PE = 1 SV = 3 | 3 | 9 | 5 |
| 53 | Prelamin-A/C OS = *Homo sapiens* GN = LMNA PE = 1 SV = 1 | 0 | 0 | 23 |
| 54 | Elongation factor 1-alpha 2 OS = *Bos taurus* GN = EEF1A2 PE = 2 SV = 1 | 0 | 4 | 3 |
| 55 | Serotransferrin OS = *Bos taurus* GN = TF PE = 2 SV = 1 | 0 | 0 | 9 |
| 56 | Gelsolin OS = *Homo sapiens* GN = GSN PE = 1 SV = 1 | 0 | 0 | 7 |
| 57 | Mucin-5B OS = *Homo sapiens* GN = MUC5B PE = 1 SV = 3 | 16 | 0 | 0 |
| 58 | Cullin-associated NEDD8-dissociated protein 1 OS = *Bos taurus* GN = CAND1 PE = 2 SV = 1 | 0 | 0 | 0 |
| 59 | Fructose-bisphosphate aldolase A OS = *Homo sapiens* GN = ALDOA PE = 1 SV = 2 | 2 | 0 | 6 |
| 60 | Peroxidasin homolog OS = *Homo sapiens* GN = PXDN PE = 1 SV = 2 | 3 | 0 | 19 |
| 61 | Nucleophosmin OS = *Homo sapiens* GN = NPM1 PE = 1 SV = 2 | 0 | 0 | 0 |
| 62 | Sulfhydryl oxidase 1 OS = *Homo sapiens* GN = QSOX1 PE = 1 SV = 3 | 0 | 3 | 24 |
| 63 | Nucleolin OS = *Homo sapiens* GN = NCL PE = 1 SV = 3 | 0 | 0 | 0 |
| 64 | Retinoic acid receptor responder protein 1 OS = *Homo sapiens* GN = RARRES1 PE = 2 SV = 2 | 0 | 0 | 0 |
| 65 | Alpha-actinin-4 OS = *Homo sapiens* GN = ACTN4 PE = 1 SV = 2 | 0 | 8 | 4 |
| 66 | Keratin, type I cytoskeletal 14 OS = *Homo sapiens* GN = KRT14 PE = 1 SV = 4 | 0 | 0 | 0 |
| 67 | Moesin OS = *Homo sapiens* GN = MSN PE = 1 SV = 3 | 5 | 13 | 4 |
| 68 | Renin receptor OS = *Homo sapiens* GN = ATP6AP2 PE = 1 SV = 2 | 0 | 0 | 3 |
| 69 | Fibronectin (Fragment) OS = *Canis familiaris* GN = FN1 PE = 2 SV = 2 | 0 | 0 | 8 |
| 70 | Clathrin heavy chain 1 OS = *Homo sapiens* GN = CLTC PE = 1 SV = 5 | 0 | 5 | 0 |
| 71 | Chloride intracellular channel protein 1 OS = *Homo sapiens* GN = CLIC1 PE = 1 SV = 4 | 0 | 3 | 11 |
| 72 | Triosephosphate isomerase OS = *Homo sapiens* GN = TPI1 PE = 1 SV = 3 | 0 | 5 | 12 |
| 73 | Apolipoprotein D OS = *Homo sapiens* GN = APOD PE = 1 SV = 1 | 0 | 0 | 0 |
| 74 | 60 kDa heat shock protein, mitochondrial OS = *Homo sapiens* GN = HSPD1 PE = 1 SV = 2 | 0 | 0 | 0 |
| 75 | Clusterin OS = *Homo sapiens* GN = CLU PE = 1 SV = 1 | 0 | 0 | 0 |
| 76 | Tenascin OS = *Homo sapiens* GN = TNC PE = 1 SV = 3 | 0 | 9 | 18 |
| 77 | Syndecan-4 OS = *Homo sapiens* GN = SDC4 PE = 1 SV = 2 | 0 | 0 | 0 |
| 78 | 14-3-3 protein epsilon OS = *Bos taurus* GN = YWHAE PE = 2 SV = 1 | 0 | 0 | 3 |
| 79 | Ras GTPase-activating-like protein IQGAP1 OS = *Homo sapiens* GN = IQGAP1 PE = 1 SV = 1 | 0 | 9 | 0 |
| 80 | L-lactate dehydrogenase B chain OS = *Homo sapiens* GN = LDHB PE = 1 SV = 2 | 0 | 4 | 8 |
| 81 | Cofilin-1 OS = *Homo sapiens* GN = CFL1 PE = 1 SV = 3 | 0 | 2 | 2 |
| 82 | Histone H4 type VIII OS = *Gallus gallus* GN = H4-VIII PE = 3 SV = 3 | 6 | 2 | 4 |
| 83 | Agrin OS = *Homo sapiens* GN = AGRN PE = 1 SV = 4 | 0 | 0 | 3 |
| 84 | Histone H1.2 (Fragment) OS = *Bos taurus* GN = HIST1H1C PE = 1 SV = 1 | 0 | 0 | 12 |
| 85 | Phosphoglycerate mutase 1 OS = *Homo sapiens* GN = PGAM1 PE = 1 SV = 2 | 0 | 0 | 8 |
| 86 | Procollagen-lysine, 2-oxoglutarate 5-dioxygenase 1 OS = *Homo sapiens* GN = PLOD1 PE = 1 SV = 2 | 0 | 0 | 15 |
| 87 | Ubiquitin-like modifier-activating enzyme 1 OS = *Homo sapiens* GN = UBA1 PE = 1 SV = 3 | 0 | 0 | 0 |
| 88 | Alpha-1-macroglobulin OS = *Rattus norvegicus* GN = A1m PE = 1 SV = 1 | 0 | 0 | 0 |
| 89 | Complement C3 OS = *Homo sapiens* GN = C3 PE = 1 SV = 2 | 0 | 0 | 5 |
| 90 | Peroxiredoxin-1 OS = *Homo sapiens* GN = PRDX1 PE = 1 SV = 1 | 2 | 2 | 0 |
| 91 | Ferritin heavy chain OS = *Homo sapiens* GN = FTH1 PE = 1 SV = 2 | 12 | 0 | 0 |
| 92 | Profilin-1 OS = *Homo sapiens* GN = PFN1 PE = 1 SV = 2 | 0 | 7 | 0 |
| 93 | Thioredoxin-1 OS = *Escherichia coli* O157:H7 GN = trxA PE = 1 SV = 2 | 0 | 0 | 0 |
| 94 | 5'-nucleotidase OS = *Homo sapiens* GN = NT5E PE = 1 SV = 1 | 10 | 6 | 0 |
| 95 | Ferritin light chain OS = *Homo sapiens* GN = FTL PE = 1 SV = 2 | 10 | 0 | 0 |
| 96 | Major vault protein OS = *Homo sapiens* GN = MVP PE = 1 SV = 4 | 11 | 4 | 0 |
| 97 | Keratin, type II cytoskeletal 2 epidermal OS = *Homo sapiens* GN = KRT2 PE = 1 SV = 2 | 0 | 3 | 0 |
| 98 | Integrin alpha-2 OS = *Homo sapiens* GN = ITGA2 PE = 1 SV = 1 | 4 | 6 | 0 |
| 99 | Keratin, type II cytoskeletal 7 OS = *Homo sapiens* GN = KRT7 PE = 1 SV = 5 | 0 | 0 | 0 |
| 100 | HLA class I histocompatibility antigen, A-2 alpha chain OS = *Homo sapiens* GN = HLA-A PE = 1 SV = 1 | 7 | 3 | 0 |

TABLE 1-continued

Comparative Proteomic Analysis of Isolated Breast Cancer Microvesicles

| # | Identified Proteins (530) | UCF | HA | EXO |
|---|---|---|---|---|
| 101 | Sodium/potassium-transporting ATPase subunit alpha-1 OS = Bos taurus GN = ATP1A1 PE = 2 SV = 1 | 6 | 7 | 0 |
| 102 | Complement C1r subcomponent OS = Pan troglodytes GN = C1R PE = 2 SV = 1 | 0 | 0 | 3 |
| 103 | Serpin B5 OS = Homo sapiens GN = SERPINB5 PE = 1 SV = 2 | 0 | 0 | 0 |
| 104 | Lactadherin OS = Homo sapiens GN = MFGE8 PE = 1 SV = 2 | 5 | 3 | 0 |
| 105 | UDP-glucose 6-dehydrogenase OS = Homo sapiens GN = UGDH PE = 1 SV = 1 | 0 | 0 | 0 |
| 106 | Laminin subunit beta-3 OS = Homo sapiens GN = LAMB3 PE = 1 SV = 1 | 0 | 0 | 0 |
| 107 | Basement membrane-specific heparan sulfate proteoglycan core protein OS = Homo sapiens GN = HSPG2 PE = 1 SV = 4 | 0 | 0 | 0 |
| 108 | Keratin, type I cytoskeletal 17 OS = Homo sapiens GN = KRT17 PE = 1 SV = 2 | 0 | 0 | 0 |
| 109 | Cadherin EGF LAG seven-pass G-type receptor 2 OS = Homo sapiens GN = CELSR2 PE = 2 SV = 1 | 0 | 0 | 0 |
| 110 | GTP-binding nuclear protein Ran OS = Bos taurus GN = RAN PE = 2 SV = 3 | 0 | 0 | 4 |
| 111 | Glucose-6-phosphate 1-dehydrogenase OS = Homo sapiens GN = G6PD PE = 1 SV = 4 | 0 | 0 | 0 |
| 112 | Annexin A1 OS = Homo sapiens GN = ANXA1 PE = 1 SV = 2 | 4 | 5 | 5 |
| 113 | Interstitial collagenase OS = Homo sapiens GN = MMP1 PE = 1 SV = 3 | 3 | 4 | 7 |
| 114 | 14-3-3 protein theta OS = Bos taurus GN = YWHAQ PE = 2 SV = 1 | 0 | 0 | 0 |
| 115 | 14-3-3 protein beta/alpha OS = Bos taurus GN = YWHAB PE = 1 SV = 2 | 0 | 0 | 2 |
| 116 | Importin subunit beta-1 OS = Homo sapiens GN = KPNB1 PE = 1 SV = 2 | 0 | 0 | 0 |
| 117 | Protein SET OS = Homo sapiens GN = SET PE = 1 SV = 3 | 0 | 0 | 0 |
| 118 | 14-3-3-like protein 1 OS = Caenorhabditis elegans GN = par-5 PE = 1 SV = 2 | 0 | 0 | 0 |
| 119 | Lysosomal alpha-glucosidase OS = Homo sapiens GN = GAA PE = 1 SV = 4 | 0 | 0 | 0 |
| 120 | Laminin subunit alpha-3 OS = Homo sapiens GN = LAMA3 PE = 1 SV = 2 | 0 | 0 | 0 |
| 121 | Integrin alpha-3 OS = Homo sapiens GN = ITGA3 PE = 1 SV = 5 | 3 | 4 | 0 |
| 122 | Extracellular sulfatase Sulf-2 OS = Homo sapiens GN = SULF2 PE = 1 SV = 1 | 0 | 0 | 0 |
| 123 | Apolipoprotein A-I OS = Bos taurus GN = APOA1 PE = 1 SV = 3 | 0 | 0 | 0 |
| 124 | 60S acidic ribosomal protein P0 OS = Homo sapiens GN = RPLP0 PE = 1 SV = 1 | 0 | 0 | 0 |
| 125 | Guanine nucleotide-binding protein subunit beta-2-like 1 OS = Bos taurus GN = GNB2L1 PE = 2 SV = 3 | 0 | 0 | 0 |
| 126 | 78 kDa glucose-regulated protein OS = Homo sapiens GN = HSPA5 PE = 1 SV = 2 | 0 | 0 | 5 |
| 127 | Glutathione S-transferase P OS = Homo sapiens GN = GSTP1 PE = 1 SV = 2 | 0 | 0 | 0 |
| 128 | Myosin-9 OS = Homo sapiens GN = MYH9 PE = 1 SV = 4 | 0 | 0 | 2 |
| 129 | Malate dehydrogenase, mitochondrial OS = Homo sapiens GN = MDH2 PE = 1 SV = 3 | 0 | 0 | 3 |
| 130 | ATP synthase subunit beta, mitochondrial OS = Homo sapiens GN = ATP5B PE = 1 SV = 3 | 0 | 0 | 0 |
| 131 | Ras-related protein Rap-1b OS = Bos taurus GN = RAP1B PE = 2 SV = 1 | 0 | 0 | 0 |
| 132 | Glycogen phosphorylase, brain form OS = Homo sapiens GN = PYGB PE = 1 SV = 5 | 0 | 0 | 6 |
| 133 | Myosin light polypeptide 6 OS = Bos taurus GN = MYL6 PE = 2 SV = 2 | 0 | 4 | 0 |
| 134 | Peroxiredoxin-5, mitochondrial OS = Homo sapiens GN = PRDX5 PE = 1 SV = 4 | 0 | 0 | 0 |
| 135 | Carbonyl reductase [NADPH] 1 OS = Homo sapiens GN = CBR1 PE = 1 SV = 3 | 0 | 0 | 4 |
| 136 | Fibronectin OS = Xenopus laevis GN = fn1 PE = 2 SV = 1 | 3 | 3 | 4 |
| 137 | Latent-transforming growth factor beta-binding protein 1 OS = Homo sapiens GN = LTBP1 PE = 1 SV = 4 | 0 | 0 | 4 |
| 138 | Core histone macro-H2A.1 OS = Homo sapiens GN = H2AFY PE = 1 SV = 4 | 0 | 0 | 6 |
| 139 | Histone H3.1t OS = Homo sapiens GN = HIST3H3 PE = 1 SV = 3 | 0 | 0 | 2 |
| 140 | Collagen alpha-1(XVIII) chain OS = Homo sapiens GN = COL18A1 PE = 1 SV = 5 | 0 | 0 | 0 |
| 141 | Laminin subunit gamma-1 OS = Homo sapiens GN = LAMC1 PE = 1 SV = 3 | 0 | 0 | 0 |
| 142 | Histone H2A.V OS = Bos taurus GN = H2AFV PE = 2 SV = 3 | 0 | 0 | 3 |
| 143 | Fructose-1,6-bisphosphatase 1 OS = Homo sapiens GN = FBP1 PE = 1 SV = 5 | 0 | 0 | 0 |
| 144 | High mobility group protein HMG-I/HMG-Y OS = Canis familiaris GN = HMGA1 PE = 3 SV = 3 | 0 | 0 | 6 |
| 145 | Extracellular matrix protein 1 OS = Homo sapiens GN = ECM1 PE = 1 SV = 2 | 0 | 0 | 10 |
| 146 | Alpha-1-acid glycoprotein OS = Bos taurus GN = ORM1 PE = 2 SV = 1 | 0 | 0 | 2 |
| 147 | Elongation factor 1-alpha 1 OS = Bos taurus GN = EEF1A1 PE = 2 SV = 1 | 0 | 0 | 0 |
| 148 | Olfactomedin-4 OS = Homo sapiens GN = OLFM4 PE = 1 SV = 1 | 0 | 0 | 0 |
| 149 | Nucleobindin-2 OS = Homo sapiens GN = NUCB2 PE = 1 SV = 2 | 0 | 0 | 0 |
| 150 | Tropomyosin alpha-3 chain OS = Rattus norvegicus GN = Tpm3 PE = 1 SV = 2 | 0 | 0 | 0 |
| 151 | 6-phosphogluconate dehydrogenase, decarboxylating OS = Homo sapiens GN = PGD PE = 1 SV = 3 | 0 | 0 | 0 |
| 152 | Heat shock protein HSP 90-alpha OS = Gallus gallus GN = HSP90AA1 PE = 3 SV = 3 | 0 | 0 | 0 |
| 153 | Tubulin beta-5 chain OS = Bos taurus GN = TUBB5 PE = 2 SV = 1 | 2 | 4 | 4 |
| 154 | Bifunctional purine biosynthesis protein PURH OS = Homo sapiens GN = ATIC PE = 1 SV = 3 | 0 | 0 | 0 |
| 155 | Eukaryotic translation initiation factor 5A-1 OS = Bos taurus GN = EIF5A PE = 2 SV = 3 | 0 | 0 | 0 |
| 156 | Factor XIIa inhibitor OS = Bos taurus PE = 1 SV = 1 | 0 | 0 | 0 |
| 157 | Fibrinogen alpha chain OS = Bos taurus GN = FGA PE = 1 SV = 5 | 0 | 0 | 0 |
| 158 | Plectin OS = Homo sapiens GN = PLEC PE = 1 SV = 3 | 0 | 0 | 0 |
| 159 | Alpha-S1-casein OS = Bos taurus GN = CSN1S1 PE = 1 SV = 2 | 0 | 0 | 0 |
| 160 | Histone H2A type 1-B/E OS = Homo sapiens GN = HIST1H2AB PE = 1 SV = 2 | 0 | 0 | 3 |
| 161 | Apolipoprotein A-I OS = Gorilla gorilla gorilla GN = APOA1 PE = 1 SV = 1 | 4 | 7 | 0 |
| 162 | Intercellular adhesion molecule 1 OS = Homo sapiens GN = ICAM1 PE = 1 SV = 2 | 2 | 4 | 0 |
| 163 | Programmed cell death 6-interacting protein OS = Homo sapiens GN = PDCD6IP PE = 1 SV = 1 | 0 | 0 | 0 |

TABLE 1-continued

Comparative Proteomic Analysis of Isolated Breast Cancer Microvesicles

| # | Identified Proteins (530) | UCF | HA | EXO |
|---|---|---|---|---|
| 164 | Eukaryotic initiation factor 4A-I OS = Bos taurus GN = EIF4A1 PE = 2 SV = 1 | 0 | 0 | 0 |
| 165 | ADP-ribosylation factor 1 OS = Bos taurus GN = ARF1 PE = 1 SV = 2 | 0 | 0 | 0 |
| 166 | Histone H2A type 1-A OS = Homo sapiens GN = HIST1H2AA PE = 1 SV = 3 | 0 | 0 | 5 |
| 167 | Protein DJ-1 OS = Homo sapiens GN = PARK7 PE = 1 SV = 2 | 0 | 0 | 0 |
| 168 | Amyloid-like protein 2 OS = Homo sapiens GN = APLP2 PE = 1 SV = 2 | 0 | 0 | 0 |
| 169 | Pancreatic trypsin inhibitor OS = Bos taurus PE = 1 SV = 2 | 2 | 0 | 0 |
| 170 | Glypican-1 OS = Homo sapiens GN = GPC1 PE = 1 SV = 2 | 0 | 0 | 0 |
| 171 | Annexin A5 OS = Homo sapiens GN = ANXA5 PE = 1 SV = 2 | 0 | 2 | 2 |
| 172 | F-actin-capping protein subunit beta OS = Bos taurus GN = CAPZB PE = 1 SV = 1 | 0 | 0 | 0 |
| 173 | ProSAAS OS = Homo sapiens GN = PCSK1N PE = 1 SV = 1 | 0 | 0 | 0 |
| 174 | Latent-transforming growth factor beta-binding protein 4 OS = Homo sapiens GN = LTBP4 PE = 1 SV = 2 | 0 | 0 | 0 |
| 175 | Glutaredoxin-1 OS = Escherichia coli (strain K12) GN = grxA PE = 1 SV = 1 | 0 | 0 | 0 |
| 176 | Stress-induced-phosphoprotein 1 OS = Homo sapiens GN = STIP1 PE = 1 SV = 1 | 0 | 0 | 0 |
| 177 | Laminin subunit beta-1 OS = Homo sapiens GN = LAMB1 PE = 1 SV = 2 | 0 | 0 | 0 |
| 178 | Protein NDRG1 OS = Homo sapiens GN = NDRG1 PE = 1 SV = 1 | 0 | 0 | 4 |
| 179 | Pentraxin-related protein PTX3 OS = Homo sapiens GN = PTX3 PE = 1 SV = 3 | 3 | 4 | 0 |
| 180 | Cystatin-C OS = Homo sapiens GN = CST3 PE = 1 SV = 1 | 0 | 2 | 0 |
| 181 | Endoplasmin OS = Homo sapiens GN = HSP90B1 PE = 1 SV = 1 | 0 | 0 | 4 |
| 182 | Cystatin-SN OS = Homo sapiens GN = CST1 PE = 1 SV = 3 | 0 | 0 | 6 |
| 183 | Complement component 1 Q subcomponent-binding protein, mitochondrial OS = Homo Sapien GN = C1QBP PE = 1 SV = 1 | 0 | 0 | 0 |
| 184 | 40S ribosomal protein SA OS = Bos taurus GN = RPSA PE = 2 SV = 4 | 0 | 0 | 3 |
| 185 | Proactivator polypeptide OS = Homo sapiens GN = PSAP PE = 1 SV = 2 | 0 | 0 | 0 |
| 186 | Elongation factor 1-delta OS = Homo sapiens GN = EEF1D PE = 1 SV = 5 | 0 | 0 | 0 |
| 187 | Hemoglobin fetal subunit beta OS = Bos taurus PE = 1 SV = 1 | 0 | 0 | 0 |
| 188 | Proteasome subunit alpha type-2 OS = Bos taurus GN = PSMA2 PE = 1 SV = 3 | 0 | 0 | 0 |
| 189 | Cell division control protein 42 homolog OS = Bos taurus GN = CDC42 PE = 1 SV= 1 | 0 | 0 | 0 |
| 190 | Erythrocyte band 7 integral membrane protein OS = Homo sapiens GN = STOM PE = 1 SV = 3 | 0 | 0 | 0 |
| 191 | Ras-related protein Rab-1B OS = Bos taurus GN = RAB1B PE = 2 SV = 1 | 0 | 0 | 0 |
| 192 | Periostin OS = Homo sapiens GN = POSTN PE = 1 SV = 2 | 0 | 0 | 0 |
| 193 | Phosphoglycerate kinase 1 OS = Bos taurus GN = PGK1 PE = 2 SV = 3 | 0 | 0 | 4 |
| 194 | Apolipoprotein E OS = Homo sapiens GN = APOE PE = 1 SV = 1 | 3 | 0 | 0 |
| 195 | Synaptic vesicle membrane protein VAT-1 homolog OS = Homo sapiens GN = VAT1 PE = 1 SV = 2 | 2 | 0 | 2 |
| 196 | Talin-1 OS = Homo sapiens GN = TLN1 PE = 1 SV = 3 | 0 | 0 | 0 |
| 197 | Heterogeneous nuclear ribonucleoprotein K OS = Bos taurus GN = HNRNPK PE = 2 SV = 1 | 0 | 0 | 0 |
| 198 | Galectin-3 OS = Homo sapiens GN = LGALS3 PE = 1 SV = 5 | 0 | 0 | 2 |
| 199 | Transketolase OS = Homo sapiens GN = TKT PE = 1 SV = 3 | 0 | 0 | 0 |
| 200 | Actin-related protein 3 OS = Bos taurus GN = ACTR3 PE = 1 SV = 3 | 0 | 0 | 0 |
| 201 | 60S ribosomal protein L12 OS = Bos taurus GN = RPL12 PE = 1 SV = 1 | 0 | 0 | 0 |
| 202 | Puromycin-sensitive aminopeptidase OS = Homo sapiens GN = NPEPPS PE = 1 SV = 2 | 0 | 0 | 0 |
| 203 | Actin-2 OS = Suillus bovinus GN = ACT2 PE = 2 SV = 1 | 0 | 0 | 0 |
| 204 | Serine protease HTRA1 OS = Homo sapiens GN = HTRA1 PE = 1 SV = 1 | 0 | 0 | 0 |
| 205 | Acidic leucine-rich nuclear phosphoprotein 32 family member A OS = Homo sapiens GN = ANP32A PE = 1 SV = 1 | 0 | 0 | 0 |
| 206 | Galectin-1 OS = Homo sapiens GN = LGALS1 PE = 1 SV = 2 | 0 | 3 | 0 |
| 207 | Beta-hexosaminidase subunit alpha OS = Homo sapiens GN = HEXA PE = 1 SV = 2 | 0 | 0 | 0 |
| 208 | Peroxiredoxin-2 OS = Homo sapiens GN = PRDX2 PE = 1 SV = 5 | 0 | 0 | 0 |
| 209 | Poly(rC)-binding protein 1 OS = Bos taurus GN = PCBP1 PE = 2 SV = 1 | 0 | 0 | 0 |
| 210 | 14-3-3 protein gamma OS = Bos taurus GN = YWHAG PE = 1 SV = 2 | 0 | 0 | 3 |
| 211 | Beta-2-microglobulin OS = Gorilla gorilla gorilla GN = B2M PE = 3 SV = 1 | 2 | 2 | 0 |
| 212 | Peptidyl-prolyl cis-trans isomerase FKBP4 OS = Homo sapiens GN = FKBP4 PE = 1 SV = 3 | 0 | 0 | 0 |
| 213 | Spectrin alpha chain, non-erythrocytic 1 OS = Homo sapiens GN = SPTAN1 PE = 1 SV = 3 | 0 | 0 | 0 |
| 214 | Lactotransferrin OS = Homo sapiens GN = LTF PE = 1 SV = 6 | 0 | 0 | 0 |
| 215 | Gamma-enolase OS = Homo sapiens GN = ENO2 PE = 1 SV = 3 | 0 | 3 | 0 |
| 216 | Keratin, type I cytoskeletal 18 OS = Mus musculus GN = Krt18 PE = 1 SV = 5 | 0 | 0 | 0 |
| 217 | Histone H2B type 1-B OS = Homo sapiens GN = HIST1H2BB PE = 1 SV = 2 | 0 | 0 | 4 |
| 218 | Extracellular superoxide dismutase [Cu—Zn] OS = Homo sapiens GN = SOD3 PE = 1 SV = 2 | 0 | 0 | 4 |
| 219 | Elongation factor 1-beta OS = Bos taurus GN = EEF1B PE = 2 SV = 3 | 0 | 0 | 0 |
| 220 | Integrin alpha-6 OS = Homo sapiens GN = ITGA6 PE = 1 SV = 4 | 8 | 3 | 0 |
| 221 | Gelsolin OS = Bos taurus GN = GSN PE = 2 SV = 1 | 0 | 0 | 0 |
| 222 | Basigin (Fragment) OS = Bos taurus GN = BSG PE = 2 SV = 1 | 2 | 2 | 0 |
| 223 | Cathepsin B OS = Homo sapiens GN = CTSB PE = 1 SV = 3 | 0 | 0 | 0 |
| 224 | Elongation factor 1-gamma OS = Homo sapiens GN = EEF1G PE = 1 SV = 3 | 0 | 0 | 2 |
| 225 | Tubulin beta-3 chain OS = Gallus gallus PE = 2 SV = 1 | 0 | 0 | 0 |
| 226 | Adenine phosphoribosyltransferase OS = Homo sapiens GN = APRT PE = 1 SV = 2 | 0 | 0 | 0 |
| 227 | Eukaryotic translation initiation factor 6 OS = Homo sapiens GN = EIF6 PE = 1 SV = 1 | 0 | 0 | 0 |

TABLE 1-continued

Comparative Proteomic Analysis of Isolated Breast Cancer Microvesicles

| # | Identified Proteins (530) | UCF | HA | EXO |
|---|---|---|---|---|
| 228 | Glypican-4 OS = *Homo sapiens* GN = GPC4 PE = 1 SV = 4 | 0 | 0 | 0 |
| 229 | Protein disulfide-isomerase OS = *Homo sapiens* GN = P4HB PE = 1 SV = 3 | 0 | 0 | 0 |
| 230 | Actin-related protein 2/3 complex subunit 4 OS = *Bos taurus* GN = ARPC4 PE = 1 SV = 3 | 0 | 0 | 0 |
| 231 | Transaldolase OS = *Homo sapiens* GN = TALDO1 PE = 1 SV = 2 | 0 | 0 | 2 |
| 232 | Metalloproteinase inhibitor 1 OS = *Homo sapiens* GN = TIMP1 PE = 1 SV = 1 | 0 | 0 | 3 |
| 233 | Proteasome subunit beta type-1 OS = *Homo sapiens* GN = PSMB1 PE = 1 SV = 2 | 2 | 0 | 0 |
| 234 | Single-stranded DNA-binding protein, mitochondrial OS = *Homo sapiens* GN = SSBP1 PE = 1 SV = 1 | 0 | 0 | 0 |
| 235 | Proliferating cell nuclear antigen OS = *Cricetulus griseus* GN = PCNA PE = 1 SV = 1 | 0 | 0 | 0 |
| 236 | Aminopeptidase B OS = *Homo sapiens* GN = RNPEP PE = 1 SV = 2 | 0 | 0 | 0 |
| 237 | Tubulin alpha-1B chain OS = *Bos taurus* PE = 1 SV = 2 | 0 | 0 | 0 |
| 238 | Complement C1s subcomponent OS = *Homo sapiens* GN = C1S PE = 1 SV = 1 | 0 | 0 | 0 |
| 239 | Proteasome subunit beta type-6 OS = *Homo sapiens* GN = PSMB6 PE = 1 SV = 4 | 2 | 0 | 0 |
| 240 | 4F2 cell-surface antigen heavy chain OS = *Homo sapiens* GN = SLC3A2 PE = 1 SV = 3 | 0 | 0 | 0 |
| 241 | 60S ribosomal protein L10a OS = *Bos taurus* GN = RPL10A PE = 2 SV = 3 | 0 | 0 | 0 |
| 242 | ADP-sugar pyrophosphatase OS = *Homo sapiens* GN = NUDT5 PE = 1 SV = 1 | 0 | 0 | 0 |
| 243 | Mucin-1 OS = *Homo sapiens* GN = MUC1 PE = 1 SV = 3 | 0 | 0 | 0 |
| 244 | Syndecan-4 OS = *Mus musculus* GN = Sdc4 PE = 1 SV = 1 | 0 | 0 | 0 |
| 245 | Glutathione S-transferase omega-1 OS = *Homo sapiens* GN = GSTO1 PE = 1 SV = 2 | 0 | 0 | 2 |
| 246 | Stanniocalcin-1 OS = *Homo sapiens* GN = STC1 PE = 1 SV = 1 | 0 | 0 | 0 |
| 247 | Collagen alpha-1(V) chain OS = *Homo sapiens* GN = COL5A1 PE = 1 SV = 3 | 0 | 0 | 8 |
| 248 | Ezrin OS = *Homo sapiens* GN = EZR PE = 1 SV = 4 | 0 | 0 | 0 |
| 249 | Proteasome subunit beta type-2 OS = *Homo sapiens* GN = PSMB2 PE = 1 SV = 1 | 0 | 0 | 0 |
| 250 | Ribonuclease inhibitor OS = *Homo sapiens* GN = RNH1 PE = 1 SV = 2 | 0 | 0 | 0 |
| 251 | Peroxiredoxin-6 OS = *Homo sapiens* GN = PRDX6 PE = 1 SV = 3 | 0 | 0 | 0 |
| 252 | Antithrombin-III OS = *Bos taurus* GN = SERPINC1 PE = 1 SV = 2 | 0 | 0 | 0 |
| 253 | Cadherin-1 OS = *Homo sapiens* GN = CDH1 PE = 1 SV = 3 | 0 | 0 | 0 |
| 254 | Mucin-5AC (Fragments) OS = *Homo sapiens* GN = MUC5AC PE = 1 SV = 3 | 2 | 0 | 0 |
| 255 | WD repeat-containing protein 1 OS = *Bos taurus* GN = WDR1 PE = 2 SV = 3 | 0 | 0 | 0 |
| 256 | Proteasome subunit beta type-5 OS = *Bos taurus* GN = PSMB5 PE = 1 SV = 1 | 0 | 0 | 0 |
| 257 | Fascin OS = *Homo sapiens* GN = FSCN1 PE = 1 SV = 3 | 0 | 0 | 0 |
| 258 | Fibronectin OS = *Rattus norvegicus* GN = Fn1 PE = 1 SV = 2 | 0 | 0 | 2 |
| 259 | Transcription intermediary factor 1-beta OS = *Homo sapiens* GN = TRIM28 PE =1 SV = 5 | 0 | 0 | 0 |
| 260 | Beta-galactosidase OS = *Homo sapiens* GN = GLB1 PE = 1 SV = 2 | 0 | 0 | 0 |
| 261 | Calmodulin-alpha (Fragment) OS = *Arbacia punctulata* PE = 2 SV = 2 | 0 | 4 | 0 |
| 262 | Aminopeptidase N OS = *Homo sapiens* GN = ANPEP PE = 1 SV = 4 | 0 | 0 | 0 |
| 263 | Fibroblast growth factor-binding protein 1 OS = *Homo sapiens* GN = FGFBP1 PE = 1 SV = 1 | 0 | 0 | 0 |
| 264 | Serine/threonine-protein phosphatase 2A 65 kDa regulatory subunit A alpha isoform OS = *Homo sapiens* GN = PPP2R1A PE = 1 SV = 4 | 0 | 0 | 0 |
| 265 | Beta-lactoglobulin OS = *Bos taurus* GN = LGB PE = 1 SV = 3 | 0 | 0 | 0 |
| 266 | Proteolipid protein 2 OS-*Homo sapiens* GN = PLP2 PE = 1 SV = 1 | 0 | 2 | 0 |
| 267 | Transgelin-2 OS = *Homo sapiens* GN = TAGLN2 PE = 1 SV = 3 | 2 | 0 | 0 |
| 268 | Complement C4-A OS = *Homo sapiens* GN = C4A PE = 1 SV = 1 | 0 | 0 | 8 |
| 269 | Fructose-bisphosphate aldolase C OS = *Homo sapiens* GN = ALDOC PE = 1 SV = 2 | 0 | 0 | 0 |
| 270 | Integrin beta-4 OS = *Homo sapiens* GN = ITGB4 PE = 1 SV = 5 | 4 | 2 | 0 |
| 271 | Prostaglandin F2 receptor negative regulator OS = *Homo sapiens* GN = PTGFRN PE = 1 SV = 2 | 0 | 0 | 0 |
| 272 | Inter-alpha-trypsin inhibitor heavy chain H2 OS = *Mus musculus* GN = Itih2 PE = 1 SV = 1 | 0 | 0 | 0 |
| 273 | Chloride intracellular channel protein 4 OS = *Homo sapiens* GN = CLIC4 PE = 1 SV = 4 | 0 | 0 | 0 |
| 274 | Omega-amidase NIT2 OS = *Homo sapiens* GN = NIT2 PE = 1 SV = 1 | 0 | 0 | 0 |
| 275 | Alpha-fetoprotein OS = *Bos taurus* GN = AFP PE = 2 SV = 1 | 0 | 0 | 0 |
| 276 | Ectonucleotide pyrophosphatase/phosphodiesterase family member 1 OS = *Homo Sapiens* GN = ENPP1 PE = 1 SV = 2 | 6 | 0 | 0 |
| 277 | Acidic leucine-rich nuclear phosphoprotein 32 family member B OS = *Homo sapiens* GN = ANP32B PE = 1 SV = 1 | 0 | 0 | 0 |
| 278 | Pyridoxal kinase OS = *Homo sapiens* GN = PDXK PE = 1 SV = 1 | 0 | 0 | 0 |
| 279 | Tumor-associated calcium signal transducer 2 OS = *Homo sapiens* GN = TACSTD2 PE =1 SV = 3 | 0 | 0 | 0 |
| 280 | Secernin-1 OS = *Homo sapiens* GN = SCRN1 PE = 1 SV = 2 | 0 | 0 | 0 |
| 281 | Nicotinamide N-methyltransferase OS = *Homo sapiens* GN = NNMT PE = 1 SV = 1 | 0 | 0 | 0 |
| 282 | T-complex protein 1 subunit beta OS = *Homo sapiens* GN = CCT2 PE = 1 SV = 4 | 0 | 0 | 0 |
| 283 | Inter-alpha-trypsin inhibitor heavy chain H4 OS = *Bos taurus* GN = ITIH4 PE = 2 SV = 1 | 0 | 0 | 0 |
| 284 | Ras-related protein Rab-7a OS = *Canis familiaris* GN = RAB7A PE = 2 SV = 1 | 0 | 0 | 0 |
| 285 | Neutral amino acid transporter B(0) OS = *Homo sapiens* GN = SLC1A5 PE = 1 SV = 2 | 0 | 0 | 0 |
| 286 | Calsyntenin-1 OS = *Homo sapiens* GN = CLSTN1 PE = 1 SV = 1 | 0 | 0 | 4 |
| 287 | Spliceosome RNA helicase DDX398 OS = *Bos taurus* GN = DDX398 PE = 2 SV = 1 | 0 | 0 | 0 |
| 288 | Ras-related C3 botulinum toxin substrate 1 OS = *Bos taurus* GN = RAC1 PE = 1 SV = 1 | 0 | 0 | 0 |
| 289 | Tripeptidyl-peptidase 1 OS = *Homo sapiens* GN = TPP1 PE = 1 SV = 2 | 0 | 0 | 0 |
| 290 | Catenin alpha-1 OS = *Bos taurus* GN = CTNNA1 PE = 2 SV = 1 | 0 | 0 | 0 |
| 291 | Actin-related protein 2-A OS = *Danio rerio* GN = actr2a PE = 2 SV = 1 | 0 | 0 | 0 |
| 292 | CD109 antigen OS = *Homo sapiens* GN = CD109 PE = 1 SV = 2 | 0 | 0 | 0 |

TABLE 1-continued

Comparative Proteomic Analysis of Isolated Breast Cancer Microvesicles

| # | Identified Proteins (530) | UCF | HA | EXO |
|---|---|---|---|---|
| 293 | 6-phosphogluconolactonase OS = *Homo sapiens* GN = PGLS PE = 1 SV = 2 | 0 | 0 | 4 |
| 294 | Carboxypeptidase E OS = *Homo sapiens* GN = CPE PE = 1 SV = 1 | 0 | 0 | 0 |
| 295 | Far upstream element-binding protein 1 OS = *Homo sapiens* GN = FUBP1 PE = 1 SV = 3 | 0 | 0 | 0 |
| 296 | Adenosylhomocysteinase OS = *Homo sapiens* GN = AHCY PE = 1 SV = 4 | 0 | 0 | 0 |
| 297 | Cytosol aminopeptidase OS = *Homo sapiens* GN = LAP3 PE = 1 SV = 3 | 0 | 0 | 0 |
| 298 | 40S ribosomal protein S3 OS = *Bos taurus* GN = RPS3 PE = 2 SV = 1 | 0 | 0 | 0 |
| 299 | Proteasome subunit alpha type-1 OS = *Homo sapiens* GN = PSMA1 PE = 1 SV = 1 | 0 | 0 | 0 |
| 300 | Macrophage-capping protein OS = *Homo sapiens* GN = CAPG PE = 1 SV = 2 | 2 | 0 | 0 |
| 301 | Keratin, type II cytoskeletal 8 OS = *Mus musculus* GN = Krt8 PE = 1 SV = 4 | 0 | 0 | 0 |
| 302 | Keratin, type II cytoskeletal 1 OS = *Rattus norvegicus* GN = Krt1 PE = 2 SV = 1 | 0 | 0 | 0 |
| 303 | Hexokinase-1 OS = *Homo sapiens* GN = HK1 PE = 1 SV = 3 | 0 | 0 | 0 |
| 304 | Semaphorin-3C OS = *Homo sapiens* GN = SEMA3C PE = 1 SV = 2 | 0 | 0 | 0 |
| 305 | Clusterin OS = *Bos taurus* GN = CLU PE = 1 SV = 1 | 0 | 0 | 0 |
| 306 | Integrin beta-1 OS = *Bos taurus* GN = ITGB1 PE = 1 SV = 3 | 3 | 0 | 0 |
| 307 | Keratin, type I cytoskeletal 16 OS = *Homo sapiens* GN = KRT16 PE = 1 SV = 4 | 0 | 0 | 0 |
| 308 | Fetuin-B OS = *Bos taurus* GN = FETUB PE = 2 SV = 1 | 0 | 0 | 0 |
| 309 | Alanine--tRNA ligase, cytoplasmic OS = *Homo sapiens* GN = AARS PE = 1 SV = 2 | 0 | 0 | 0 |
| 310 | Ras-related protein Rab-11A OS = *Bos taurus* GN = RAB11A PE = 2 SV = 3 | 0 | 0 | 0 |
| 311 | Rab GDP dissociation inhibitor alpha OS = *Homo sapiens* GN = GDI1 PE = 1 SV = 2 | 0 | 0 | 0 |
| 312 | T-complex protein 1 subunit gamma OS = *Bos taurus* GN = CCT3 PE = 1 SV = 1 | 0 | 0 | 0 |
| 313 | Lysosomal protective protein OS = *Homo sapiens* GN = CTSA PE = 1 SV = 2 | 0 | 0 | 0 |
| 314 | Ubiquitin carboxyl-terminal hydrolase 5 OS = *Homo sapiens* GN = USP5 PE = 1 SV = 2 | 0 | 0 | 0 |
| 315 | Alpha-actinin-1 OS = *Bos taurus* GN = ACTN1 PE = 2 SV = 1 | 0 | 0 | 0 |
| 316 | Trypsin-2 OS = *Homo sapiens* GN = PRSS2 PE = 1 SV = 1 | 0 | 0 | 3 |
| 317 | Ubiquitin thioesterase OTUB1 OS = *Homo sapiens* GN = OTUB1 PE = 1 SV = 2 | 0 | 0 | 0 |
| 318 | Nucleoside diphosphate kinase A 1 OS = *Bos taurus* GN = NME1-1 PE = 1 SV = 3 | 0 | 0 | 0 |
| 319 | F-actin-capping protein subunit alpha-2 OS = *Loxodonta africana* GN = CAPZA2 PE = 3 SV = 3 | 0 | 0 | 0 |
| 320 | Laminin subunit alpha-5 OS = *Homo sapiens* GN = LAMA5 PE = 1 SV = 8 | 0 | 0 | 0 |
| 321 | Platelet-activating factor acetylhydrolase IB subunit beta OS = *Bos taurus* GN = PAFAH1B2 PE = 1 SV = 1 | 0 | 0 | 0 |
| 322 | Secreted frizzled-related protein 1 OS = *Bos taurus* GN = SFRP1 PE = 2 SV = 1 | 0 | 0 | 0 |
| 323 | Vacuolar protein sorting-associated protein 35 OS = *Bos taurus* GN = VPS35 PE = 2 SV = 1 | 0 | 0 | 0 |
| 324 | Proteasome subunit beta type-3 OS = *Bos taurus* GN = PSMB3 PE = 1 SV = 3 | 0 | 0 | 0 |
| 325 | Keratin, type I cytoskeletal 15 OS = *Homo sapiens* GN = KRT15 PE = 1 SV = 3 | 0 | 0 | 0 |
| 326 | Fatty acid-binding protein, epidermal OS = *Homo sapiens* GN = FABP5 PE = 1 SV = 3 | 0 | 0 | 0 |
| 327 | Importin-7 OS = *Homo sapiens* GN = IPO7 PE = 1 SV = 1 | 0 | 0 | 0 |
| 328 | Neutrophil gelatinase-associated lipocalin OS = *Homo sapiens* GN = LCN2 PE = 1 SV = 2 | 0 | 0 | 0 |
| 329 | 40S ribosomal protein S4, X isoform OS = *Chlorocebus aethiops* GN = RPS4X PE =2 SV = 3 | 0 | 0 | 0 |
| 330 | Signal transducer and activator of transcription 1-alpha/beta OS = *Homo sapiens* GN = STAT1 PE =1 SV = 2 | 0 | 0 | 0 |
| 331 | Glycine--tRNA ligase OS = *Homo sapiens* GN = GARS PE = 1 SV = 3 | 0 | 0 | 0 |
| 332 | Heterogeneous nuclear ribonucleoprotein Q OS = *Homo sapiens* GN = SYNCRIP PE = 1 SV = 2 | 0 | 0 | 0 |
| 333 | Rho GDP-dissociation inhibitor 1 OS = *Homo sapiens* GN = ARHGDIA PE = 1 SV = 3 | 0 | 0 | 2 |
| 334 | Serum albumin OS = *Ovis aries* GN = ALB PE = 2 SV = 1 | 0 | 0 | 0 |
| 335 | Serum albumin OS = *Oryctolagus cuniculus* GN = ALB PE = 1 SV = 2 | 0 | 0 | 0 |
| 336 | Chloride intracellular channel protein 6 OS = *Rattus norvegicus* GN = Clic6 PE = 1 SV = 1 | 0 | 0 | 2 |
| 337 | F-actin-capping protein subunit alpha-1 OS = *Bos taurus* GN = CAPZA1 PE = 2 SV = 1 | 0 | 0 | 0 |
| 338 | Lysosomal acid lipase/cholesteryl ester hydrolase OS = *Homo sapiens* GN = LIPA PE = 1 SV = 2 | 0 | 0 | 0 |
| 339 | Heat shock 70 kDa protein 4 OS = *Canis familiaris* GN = HSPA4 PE = 1 SV = 1 | 0 | 0 | 0 |
| 340 | Importin-5 OS = *Homo sapiens* GN = IPO5 PE = 1 SV = 4 | 0 | 0 | 0 |
| 341 | 14-3-3 protein eta OS = *Homo sapiens* GN = YWHAH PE = 1 SV = 4 | 0 | 0 | 0 |
| 342 | Cellular retinoic acid-binding protein 2 OS = *Homo sapiens* GN = CRABP2 PE = 1 SV = 2 | 0 | 0 | 0 |
| 343 | V-type proton ATPase subunit S1 OS = *Homo sapiens* GN = ATP6AP1 PE = 1 SV = 2 | 0 | 0 | 0 |
| 344 | Protein S100-A10 OS = *Bos taurus* GN = S100A10 PE = 1 SV = 2 | 0 | 2 | 0 |
| 345 | Triptophan--tRNA ligase, cytoplasmic OS = *Homo sapiens* GN = WARS PE = 1 SV = 2 | 0 | 0 | 0 |
| 346 | Prominin-2 OS = *Homo sapiens* GN = PROM2 PE = 1 SV = 1 | 0 | 0 | 0 |
| 347 | Deoxyribonucleoside 5'-monophosphate N-glycosidase OS = *Homo sapiens* GN = RCL PE = 1 SV = 1 | 0 | 0 | 0 |
| 348 | T-complex protein 1 subunit epsilon OS = *Homo sapiens* GN = CCT5 PE = 1 SV = 1 | 0 | 0 | 0 |
| 349 | HLA class I histocompatibility antigen, B-35 alpha chain OS = *Homo sapiens* GN = HLA-B PE = 1 SV = 1 | 2 | 0 | 0 |
| 350 | C-1-tetrahydrofolate synthase, cytoplasmic OS = *Homo sapiens* GN = MTHFD1 PE = 1 SV = 3 | 0 | 0 | 0 |
| 351 | Beta-hexosaminidase subunit beta OS = *Homo sapiens* GN = HEXB PE = 1 SV = 3 | 0 | 0 | 0 |
| 352 | Keratin, type I cuticular Ha1 OS = *Homo sapiens* GN = KRT31 PE = 2 SV = 3 | 0 | 0 | 3 |

TABLE 1-continued

Comparative Proteomic Analysis of Isolated Breast Cancer Microvesicles

| # | Identified Proteins (530) | UCF | HA | EXO |
|---|---|---|---|---|
| 353 | Prominin-1 OS = *Homo sapiens* GN = PROM1 PE = 1 SV = 1 | 0 | 0 | 0 |
| 354 | Carcinoembryonic antigen-related cell adhesion molecule 1 OS = *Homo sapiens* GN = CEACAM1 PE = 1 SV = 2 | 0 | 0 | 0 |
| 355 | Heterogeneous nuclear ribonucleoprotein A1 OS = *Bos taurus* GN = HNRNPA1 PE = 1 SV = 2 | 0 | 0 | 0 |
| 356 | Nicotinamide phosphoribosyltransferase OS = *Homo sapiens* GN = NAMPT PE = 1 SV = 1 | 0 | 0 | 0 |
| 357 | Guanine nucleotide-binding protein G(i) subunit alpha-2 OS = *Canis familiaris* GN = GNAI2 PE = 2 SV = 2 | 0 | 0 | 0 |
| 358 | Glia maturation factor beta OS = *Bos taurus* GN = GMFB PE = 1 SV = 2 | 0 | 0 | 0 |
| 359 | 26S proteasome non-ATPase regulatory subunit 2 OS = *Bos taurus* GN = PSMD2 PE = 1 SV = 2 | 0 | 0 | 0 |
| 360 | Isochorismatase domain-containing protein 1 OS = *Bos taurus* GN = ISOC1 PE = 2 SV = 1 | 0 | 0 | 0 |
| 361 | Exportin-2 OS = *Bos taurus* GN = CSE1L PE = 2 SV = 1 | 0 | 0 | 0 |
| 362 | Creatine kinase U-type, mitochondrial OS = *Homo sapiens* GN = CKMT1A PE = 1 SV = 1 | 0 | 0 | 0 |
| 363 | Farnesyl pyrophosphate synthase OS = *Homo sapiens* GN = FDPS PE = 1 SV = 4 | 0 | 0 | 0 |
| 364 | Proteasome activator complex subunit 1 OS = *Homo sapiens* GN = PSME1 PE = 1 SV = 1 | 0 | 0 | 0 |
| 365 | Phosphatidylethanolamine-binding protein 1 OS = *Homo sapiens* GN = PEBP1 PE = 1 SV = 3 | 0 | 0 | 0 |
| 366 | Adenylyl cyclase-associated protein 1 OS = *Macaca fascicularis* GN = CAP1 PE = 2 SV = 3 | 0 | 0 | 0 |
| 367 | Syntenin-1 OS = *Homo sapiens* GN = SDCBP PE = 1 SV = 1 | 0 | 0 | 0 |
| 368 | Aldo-keto reductase family 1 member C1 OS = *Homo sapiens* GN = AKR1C1 PE = 1 SV = 1 | 0 | 0 | 0 |
| 369 | Biliverdin reductase A OS = *Homo sapiens* GN = BLVRA PE = 1 SV = 2 | 0 | 0 | 0 |
| 370 | PCTP-like protein OS = *Homo sapiens* GN = STARD10 PE = 2 SV = 2 | 0 | 0 | 0 |
| 371 | Kinesin-1 heavy chain OS = *Homo sapiens* GN = KIF5B PE = 1 SV = 1 | 0 | 0 | 0 |
| 372 | Selenium-binding protein 1 OS = *Homo sapiens* GN = SELENBP1 PE = 1 SV = 2 | 0 | 0 | 0 |
| 373 | T-complex protein 1 subunit eta OS = *Bos taurus* GN = CCT7 PE = 1 SV = 1 | 0 | 0 | 0 |
| 374 | Disintegrin and metalloproteinase domain-containing protein 15 OS = *Homo sapiens* GN = ADAM15 PE = 1 SV = 4 | 0 | 0 | 0 |
| 375 | Plasma alpha-L-fucosidase OS = *Homo sapiens* GN = FUCA2 PE = 1 SV = 2 | 0 | 0 | 0 |
| 376 | Superoxide dismutase [Mn], mitochondrial OS = *Homo sapiens* GN = SOD2 PE = 1 SV = 2 | 0 | 0 | 0 |
| 377 | Nicotinate-nucleotide pyrophosphorylase [carboxylating] OS = *Homo sapiens* GN = QPRT PE = 1 SV = 3 | 0 | 0 | 0 |
| 378 | T-complex protein 1 subunit zeta OS = *Homo sapiens* GN = CCT6A PE = 1 SV = 3 | 0 | 0 | 0 |
| 379 | 40S ribosomal protein S18 OS = *Bos taurus* GN = RPS18 PE = 2 SV = 3 | 0 | 0 | 0 |
| 380 | Carcinoembryonic antigen-related cell adhesion molecule 6 OS = *Homo sapiens* GN = CEACAM6 PE = 1 SV = 3 | 0 | 0 | 0 |
| 381 | Proteasome subunit beta type-4 OS = *Homo sapiens* GN = PSMB4 PE = 1 SV = 4 | 0 | 0 | 0 |
| 382 | Splicing factor, proline- and glutamine-rich OS = *Homo sapiens* GN = SFPQ PE = 2 | 0 | 0 | 0 |
| 383 | Acyl-coenzyme A thioesterase 13 OS = *Homo sapiens* GN = ACOT13 PE = 1 SV = 1 | 0 | 0 | 3 |
| 384 | Heat shock 70 kDa protein cognate 2 OS = *Drosophila melanogaster* GN = Hsc70-2 PE = 1 SV = 2 | 0 | 0 | 0 |
| 385 | Transthyretin OS = *Bos taurus* GN = TTR PE = 1 SV = 1 | 0 | 0 | 0 |
| 386 | Sepiapterin reductase OS = *Homo sapiens* GN = SPR PE = 1 SV = 1 | 0 | 0 | 0 |
| 387 | Nascent polypeptide-associated complex subunit alpha, muscle-specific form OS = *Mus musculus* GN = Naca PE = 1 SV = 2 | 0 | 0 | 0 |
| 388 | Charged multivesicular body protein 4b OS = *Homo sapiens* GN = CHMP4B PE = 1 SV = 1 | 0 | 0 | 0 |
| 389 | Heat shock cognate 70 kDa protein OS = *Oncorhynchus mykiss* GN = hsc71 PE = 2 SV = 2 | 0 | 0 | 0 |
| 390 | T-complex protein 1 subunit delta OS = *Bos taurus* GN = CCT4 PE = 1 SV = 3 | 0 | 0 | 0 |
| 391 | 45 kDa calcium-binding protein OS = *Homo sapiens* GN = SDF4 PE = 1 SV = 1 | 0 | 0 | 0 |
| 392 | Integrin alpha-V OS = *Homo sapiens* GN = ITGAV PE = 1 SV = 2 | 3 | 0 | 0 |
| 393 | Protein disulfide-isomerase A4 OS = *Homo sapiens* GN = PDIA4 PE = 1 SV = 2 | 0 | 0 | 2 |
| 394 | Thymidine phosphorylase OS = *Homo sapiens* GN = TYMP PE = 1 SV = 2 | 0 | 0 | 0 |
| 395 | Lactoylglutathione lyase OS = *Homo sapiens* GN = GLO1 PE = 1 SV = 4 | 0 | 0 | 0 |
| 396 | Glutathione S-transferase Mu 3 OS = *Homo sapiens* GN = GSTM3 PE = 1 SV = 3 | 0 | 0 | 0 |
| 397 | 40S ribosomal protein S20 OS = *Bos taurus* GN = RPS20 PE = 3 SV = 1 | 0 | 0 | 0 |
| 398 | Heterogeneous nuclear ribonucleoproteins C1/C2 OS = *Homo sapiens* GN = HNRNPC PE = 1 SV = 4 | 0 | 0 | 0 |
| 399 | Dynactin subunit 2 OS = *Homo sapiens* GN = DCTN2 PE = 1 SV = 4 | 0 | 0 | 0 |
| 400 | Sialidase-1 OS = *Homo sapiens* GN = NEU1 PE = 1 SV = 1 | 0 | 0 | 0 |
| 401 | Serine/threonine-protein phosphatase PP1-alpha catalytic subunit OS = *Bos taurus* GN = PPP1CA PE = 2 SV = 1 | 0 | 0 | 0 |
| 402 | T-complex protein 1 subunit theta OS = *Gallus gallus* GN = CCT8 PE = 1 SV = 3 | 0 | 0 | 0 |
| 403 | Procollagen-lysine,2-oxoglutarate 5-dioxygenase 2 OS = *Homo sapiens* GN = PLOD2 PE = 1 SV = 2 | 0 | 0 | 0 |

TABLE 1-continued

Comparative Proteomic Analysis of Isolated Breast Cancer Microvesicles

| # | Identified Proteins (530) | Number of unique peptides | | |
|---|---|---|---|---|
| | | UCF | HA | EXO |
| 404 | Keratin, type II cuticular Hb6 OS = Homo sapiens GN = KRT86 PE = 1 SV = 1 | 0 | 0 | 4 |
| 405 | NAD(P)H dehydrogenase [quinone] 1 OS = Homo sapiens GN = NQO1 PE = 1 SV = 1 | 0 | 0 | 0 |
| 406 | Chromobox protein homolog 3 OS = Homo sapiens GN = CBX3 PE = 1 SV = 4 | 0 | 0 | 0 |
| 407 | Macrophage colony-stimulating factor 1 OS = Homo sapiens GN = CSF1 PE = 1 SV = 2 | 0 | 0 | 0 |
| 408 | High mobility group protein B1 OS = Bos taurus GN = HMGB1 PE = 1 SV = 3 | 0 | 0 | 0 |
| 409 | DNA-(apurinic or apyrimidinic site) lyase OS = Gorilla gorilla gorilla GN = APEX1 PE = 3 SV = 1 | 0 | 0 | 0 |
| 410 | Stress-70 protein, mitochondrial OS = Bos taurus GN = HSPA9 PE = 2 SV = 1 | 0 | 0 | 0 |
| 411 | Protein disulfide-isomerase A6 OS = Homo sapiens GN = PDIA6 PE = 1 SV = 1 | 0 | 0 | 0 |
| 412 | Destrin OS = Bos taurus GN = DSTN PE = 2 SV = 3 | 0 | 0 | 0 |
| 413 | Guanine nucleotide-binding protein G(I)/G(S)/G(T) subunit beta-1 OS = Bos taurus GN = GNB1 PE = 1 SV = 3 | 0 | 0 | 0 |
| 414 | Alkaline phosphatase, placental type OS = Homo sapiens GN = ALPP PE = 1 SV = 2 | 0 | 0 | 0 |
| 415 | Tubulointerstitial nephritis antigen-like OS = Homo sapiens GN = TINAGL1 PE = 1 SV = 1 | 0 | 0 | 0 |
| 416 | T-complex protein 1 subunit alpha OS = Cricetulus griseus GN = TCP1 PE = 2 SV = 1 | 0 | 0 | 0 |
| 417 | DNA damage-binding protein 1 OS = Bos taurus GN = DDB1 PE = 2 SV = 1 | 0 | 0 | 0 |
| 418 | Decorin OS = Homo sapiens GN = DCN PE = 1 SV = 1 | 0 | 0 | 0 |
| 419 | Heat shock protein 105 kDa OS = Homo sapiens GN = HSPH1 PE = 1 SV = 1 | 0 | 0 | 0 |
| 420 | Flavin reductase (NADPH) OS = Homo sapiens GN = BLVRB PE = 1 SV = 3 | 0 | 0 | 0 |
| 421 | Ubiquitin carboxyl-terminal hydrolase isozyme L3 OS = Homo sapiens GN = UCHL3 PE = 1 SV = 1 | 0 | 0 | 0 |
| 422 | 40S ribosomal protein S3a OS = Bos taurus GN = RPS3A PE = 2 SV = 3 | 0 | 0 | 0 |
| 423 | Specifically androgen-regulated gene protein OS = Homo sapiens GN = SARG PE = 1 SV = 2 | 0 | 0 | 0 |
| 424 | Transforming protein RhoA OS = Bos taurus GN = RHOA PE = 1 SV = 1 | 0 | 0 | 0 |
| 425 | Neutral alpha-glucosidase AB OS = Homo sapiens GN = GANAB PE = 1 SV = 3 | 0 | 0 | 0 |
| 426 | Coatomer subunit gamma-1 OS = Bos taurus GN = COPG1 PE = 1 SV = 1 | 0 | 0 | 0 |
| 427 | 60S acidic ribosomal protein P1 OS = Bos taurus GN = RPLP1 PE = 3 SV = 1 | 0 | 0 | 0 |
| 428 | Midkine OS = Homo sapiens GN = MDK PE = 1 SV = 1 | 0 | 0 | 0 |
| 429 | Eukaryotic translation initiation factor 2 subunit 1 OS = Homo sapiens GN = EIF2S1 PE = 1 SV = 3 | 0 | 0 | 0 |
| 430 | Tropomyosin alpha-4 chain OS = Equus caballus GN = TPM4 PE = 1 SV = 2 | 0 | 0 | 0 |
| 431 | Proteasome activator complex subunit 3 OS = Gallus gallus GN = PSME3 PE = 1 SV = 1 | 0 | 0 | 0 |
| 432 | Hypoxanthine-guanine phosphoribosyltransferase OS = Homo sapiens GN = HPRT1 PE = 1 SV = 2 | 0 | 0 | 0 |
| 433 | Procollagen-lysine,2-oxoglutarate 5-dioxygenase 3 OS = Homo sapiens GN = PLCD3 PE = 1 SV = 2 | 0 | 0 | 0 |
| 434 | Hsp90 co-chaperone Cdc37 OS = Homo sapiens GN = CDC37 PE = 1 SV = 1 | 0 | 0 | 0 |
| 435 | Calcyclin-binding protein OS = Homo sapiens GN = CACYBP PE = 1 SV = 2 | 0 | 0 | 0 |
| 436 | Abhydrolase domain-containing protein 14B OS = Homo sapiens GN = ABHD14B PE = 1 SV = 1 | 0 | 0 | 0 |
| 437 | Bifunctional ATP-dependent dihydroxyacetone kinase/FAD-AMP lyase (cyclizing) OS = Homo Sapiens GN = DAK PE = 1 SV = 2 | 0 | 0 | 0 |
| 438 | Fumarate hydratase, mitochondrial OS = Homo sapiens GN = FH PE = 1 SV = 3 | 0 | 0 | 0 |
| 439 | Protein SEC13 homolog OS = Homo sapiens GN = SEC13 PE = 1 SV = 3 | 0 | 0 | 0 |
| 440 | Enoyl-CoA hydratase, mitochondrial OS = Pongo abelii GN = ECHS1 PE = 2 SV = 1 | 0 | 0 | 0 |
| 441 | Electron transfer flavoprotein subunit alpha, mitochondrial OS = Homo sapiens GN = ETFA PE = 1 SV = 1 | 0 | 0 | 0 |
| 442 | Poly(rC)-binding protein 2 OS = Homo sapiens GN = PCBP2 PE = 1 SV = 1 | 0 | 0 | 0 |
| 443 | Translationally-controlled tumor protein OS = Homo sapiens GN = TPT1 PE = 1 SV = 1 | 0 | 0 | 0 |
| 444 | Ras-related protein Rap-2a OS = Sus scrofa GN = RAP2A PE = 2 SV = 1 | 0 | 0 | 0 |
| 445 | Brain acid soluble protein 1 OS = Homo sapiens GN = BASP1 PE = 1 SV = 2 | 0 | 0 | 0 |
| 446 | Complement C3 OS = Bos taurus GN = C3 PE = 1 SV = 2 | 0 | 0 | 0 |
| 447 | Glucosylceramidase OS = Homo sapiens GN = GBA PE = 1 SV = 3 | 0 | 0 | 0 |
| 448 | Inorganic pyrophosphatase OS = Homo sapiens GN = PPA1 PE = 1 SV = 2 | 0 | 0 | 0 |
| 449 | Regucalcin OS = Bos taurus GN = RGN PE = 2 SV = 1 | 0 | 0 | 0 |
| 450 | S-formylglutathione hydrolase OS = Homo sapiens GN = ESD PE = 1 SV = 2 | 0 | 0 | 0 |
| 451 | Hsc70-interacting protein OS = Homo sapiens GN = ST13 PE = 1 SV = 2 | 0 | 0 | 0 |
| 452 | X-ray repair cross-complementing protein 5 OS = Homo sapiens GN = XRCC5 PE = 1 SV = 3 | 0 | 0 | 0 |
| 453 | Importin-4 OS = Homo sapiens GN = IPO4 PE = 1 SV = 2 | 0 | 0 | 0 |
| 454 | Alpha-1-antichymotrypsin OS = Homo sapiens GN = SERPINA3 PE = 1 SV = 2 | 0 | 0 | 0 |
| 455 | Glucosamine--fructose-6-phosphate aminotransferase [isomerizing] 1 OS = Homo sapiens GN = GFPT1 PE = 1 SV = 3 | 0 | 0 | 0 |
| 456 | Microtubule-associated protein RP/EB family member 1 OS = Homo sapiens GN = MAPRE1 PE = 1 SV = 3 | 0 | 0 | 0 |
| 457 | V-type proton ATPase catalytic subunit A OS = Homo sapiens GN = ATP6V1A PE = 1 SV = 2 | 0 | 0 | 0 |
| 458 | Palmitoyl-protein thioesterase 1 OS = Mus musculus GN = Ppt1 PE = 2 SV = 2 | 0 | 0 | 0 |
| 459 | UPF0364 protein C6orf211 OS = Homo sapiens GN = C6orf211 PE = 1 SV = 1 | 0 | 0 | 0 |
| 460 | Fibulin-1 (Fragment) OS = Chlorocebus aethiops GN = FBLN1 PE = 1 SV = 1 | 0 | 0 | 0 |
| 461 | Nucleosome assembly protein 1-like 1 OS = Bos taurus GN = NAP1L1 PE = 2 SV = 1 | 0 | 0 | 0 |

TABLE 1-continued

Comparative Proteomic Analysis of Isolated Breast Cancer Microvesicles

| # | Identified Proteins (530) | Number of unique peptides | | |
|---|---|---|---|---|
| | | UCF | HA | EXO |
| 462 | Receptor-type tyrosine-protein phosphatase F OS = Homo sapiens GN = PTPRF PE = 1 SV = 2 | 0 | 0 | 0 |
| 463 | Isoleucine--tRNA ligase, mitochondrial OS = Homo sapiens GN = IARS2 PE = 1 SV = 2 | 0 | 0 | 0 |
| 464 | Arginine--tRNA ligase, cytoplasmic OS = Homo sapiens GN = RARS PE = 1 SV = 2 | 0 | 0 | 0 |
| 465 | Serine--tRNA ligase, cytoplasmic OS = Homo sapiens GN = SARS PE = 1 SV = 3 | 0 | 0 | 0 |
| 466 | Alpha-galactosidase A OS = Homo sapiens GN = GLA PE = 1 SV = 1 | 0 | 0 | 0 |
| 467 | Methionine--tRNA ligase, cytoplasmic OS = Homo sapiens GN = MARS PE = 1 SV = 2 | 0 | 0 | 0 |
| 468 | 26S proteasome non-ATPase regulatory subunit 8 OS = Homo sapiens GN = PSMD8 PE = 1 SV = 2 | 0 | 0 | 0 |
| 469 | Aflatoxin B1 aldehyde reductase member 2 OS = Homo sapiens GN = AKR7A2 PE = 1 SV = 3 | 0 | 0 | 0 |
| 470 | Cytoplasmic dynein 1 intermediate chain 2 OS = Bos taurus GN = DYNC1I2 PE = 1 SV = 1 | 0 | 0 | 0 |
| 471 | Epidermal growth factor receptor kinase substrate 8-like protein 1 OS = Homo sapiens GN = EPS8L1 PE = 1 SV = 3 | 0 | 0 | 0 |
| 472 | Growth/differentiation factor 15 OS = Homo sapiens GN = GDF15 PE = 1 SV = 3 | 0 | 0 | 0 |
| 473 | Hydroxyacylglutathione hydrolase, mitochondrial OS = Homo sapiens GN = HAGH PE = 1 SV = 2 | 0 | 0 | 0 |
| 474 | Glycerol-3-phosphate dehydrogenase 1-like protein OS = Homo sapiens GN = GPD1L PE = 1 SV = 1 | 0 | 0 | 0 |
| 475 | Beta-hexosaminidase subunit alpha OS = Pongo abelii GN = HEXA PE = 3 SV = 1 | 0 | 0 | 0 |
| 476 | Insulin-like growth factor-binding protein 1 OS = Homo sapiens GN = IGFBP1 PE = 1 SV = 1 | 0 | 0 | 0 |
| 477 | Inositol monophosphatase 1 OS = Homo sapiens GN = IMPA1 PE = 1 SV = 1 | 0 | 0 | 0 |
| 478 | Pyruvate kinase isozymes M1/M2 OS = Mus musculus GN = Pkm PE = 1 SV = 4 | 0 | 0 | 0 |
| 479 | Programmed cell death protein 6 OS = Homo sapiens GN = PDCD6 PE = 1 SV = 1 | 0 | 0 | 0 |
| 480 | Alpha-soluble NSF attachment protein OS = Homo sapiens GN = NAPA PE = 1 SV = 3 | 0 | 0 | 0 |
| 481 | Serpin A3-1 OS = Bos taurus GN = SERPINA3-1 PE = 1 SV = 3 | 0 | 0 | 0 |
| 482 | Eukaryotic translation initiation factor 3 subunit C OS = Bos taurus GN = EIF3C PE = 2 SV = 1 | 0 | 0 | 0 |
| 483 | Vesicle-associated membrane protein-associated protein A OS = Bos taurus GN = VAPA PE = 2 SV = 1 | 0 | 0 | 0 |
| 484 | Calpain-1 catalytic subunit OS = Homo sapiens GN = CAPN1 PE = 1 SV = 1 | 0 | 0 | 0 |
| 485 | Histone H1.5 OS = Homo sapiens GN = HIST1H1B PE = 1 SV = 3 | 0 | 0 | 0 |
| 486 | Dihydropyrimidinase-related protein 2 OS = Homo sapiens GN = DPYSL2 PE = 1 SV = 1 | 0 | 0 | 0 |
| 487 | Coronin-1B OS = Homo sapiens GN = CORO1B PE = 1 SV = 1 | 0 | 0 | 0 |
| 488 | X-ray repair cross-complementing protein 6 OS = Homo sapiens GN = XRCC6 PE = 1 SV = 2 | 0 | 0 | 0 |
| 489 | 6-phosphofructokinase, liver type OS = Homo sapiens GN = PFKL PE = 1 SV = 6 | 0 | 0 | 0 |
| 490 | Tubulin beta-3 chain OS = Bos taurus GN = TUBB3 PE = 2 SV = 1 | 0 | 0 | 0 |
| 491 | Anterior gradient protein 2 homolog OS = Homo sapiens GN = AGR2 PE = 1 SV = 1 | 0 | 0 | 0 |
| 492 | Antithrombin-III OS = Mus musculus GN = Serpinc1 PE = 1 SV = 1 | 0 | 0 | 0 |
| 493 | Apoptosis inhibitor 5 OS = Homo sapiens GN = API5 PE = 1 SV = 3 | 0 | 0 | 0 |
| 494 | ATP synthase subunit delta, mitochondrial OS = Homo sapiens GN = ATP5D PE = 1 SV = 2 | 0 | 0 | 0 |
| 495 | Brain-specific angiogenesis inhibitor 1-associated protein 2 OS = Homo sapiens GN = BAIAP2 PE = 1 SV = 1 | 0 | 0 | 0 |
| 496 | Basal cell adhesion molecule OS = Homo sapiens GN = BCAM PE = 1 SV = 2 | 0 | 0 | 0 |
| 497 | Alpha-S2-casein OS = Bos taurus GN = CSN1S2 PE = 1 SV = 2 | 0 | 0 | 0 |
| 498 | Chromobox protein homolog 1 OS = Homo sapiens GN = CBX1 PE = 1 SV = 1 | 0 | 0 | 0 |
| 499 | Protocadherin Fat 2 OS = Homo sapiens GN = FAT2 PE = 1 SV = 2 | 0 | 0 | 0 |
| 500 | Flotillin-1 OS = Homo sapiens GN = FLOT1 PE = 1 SV = 3 | 2 | 0 | 0 |
| 501 | Guanine nucleotide-binding protein G(I)/G(S)/G(T) subunit beta-2 OS = Bos taurus GN = GNB2 PE = 2 SV = 3 | 0 | 0 | 0 |
| 502 | Heat shock 70 kDa protein 1A OS = Bos taurus GN = HSPA1A PE = 2 SV = 2 | 0 | 0 | 0 |
| 503 | Keratin, type II cytoskeletal 4 OS = Homo sapiens GN = KRT4 PE = 1 SV = 4 | 0 | 0 | 0 |
| 504 | Large neutral amino acids transporter small subunit 1 OS = Homo sapiens GN = SLC7A5 PE = 1 SV = 2 | 0 | 0 | 0 |
| 505 | Latexin OS = Homo sapiens GN = LXN PE = 1 SV = 2 | 0 | 0 | 0 |
| 506 | Nucleosome assembly protein 1-like 4 OS = Homo sapiens GN = NAP1L4 PE = 1 SV = 1 | 0 | 0 | 0 |
| 507 | Protocadherin beta-14 OS = Homo sapiens GN = PCDHB14 PE = 2 SV = 1 | 0 | 0 | 0 |
| 508 | Serine/threonine-protein phosphatase 2A catalytic subunit alpha isoform OS = Bos taurus GN = PPP2CA PE = 1 SV = 1 | 0 | 0 | 0 |
| 509 | Ran-specific GTPase-activating protein OS = Homo sapiens GN = RANBP1 PE = 1 SV =1 | 0 | 0 | 0 |
| 510 | Histone-binding protein RBBP7 OS = Bos taurus GN = RBBP7 PE = 2 SV = 1 | 0 | 0 | 0 |
| 511 | 40S ribosomal protein S16 OS = Bos taurus GN = RPS16 PE = 2 SV = 3 | 0 | 0 | 0 |
| 512 | Antileukoproteinase OS = Homo sapiens GN = SLPI PE = 1 SV = 1 | 0 | 0 | 0 |
| 513 | 3-ketoacyl-CoA thiolase, mitochondrial OS = Homo sapiens GN = ACAA2 PE = 1 SV = 2 | 0 | 0 | 0 |
| 514 | 3-mercaptopyruvate sulfurtransferase OS = Homo sapiens GN = MPST PE = 1 SV = 3 | 0 | 0 | 0 |
| 515 | Glucose-6-phosphate isomerase OS = Homo sapiens GN = GPI PE = 1 SV = 4 | 0 | 0 | 0 |
| 516 | Ovalbumin OS = Gallus gallus GN = SERPINB14 PE = 1 SV = 2 | 0 | 0 | 0 |

TABLE 1-continued

Comparative Proteomic Analysis of Isolated Breast Cancer Microvesicles

| # | Identified Proteins (530) | Number of unique peptides | | |
|---|---|---|---|---|
| | | UCF | HA | EXO |
| 517 | 26S proteasome non-ATPase regulatory subunit 5 OS = Homo sapiens GN = PSMD5 PE = 1 SV = 3 | 0 | 0 | 0 |
| 518 | Ras-related protein Rab-22A OS = Homo sapiens GN = RAB22A PE = 1 SV = 2 | 0 | 0 | 0 |
| 519 | 40S ribosomal protein S15a OS = Bos taurus GN = RPS15A PE = 2 SV = 1 | 0 | 0 | 0 |
| 520 | 40S ribosomal protein S17-like OS = Homo sapiens GN = RPS17L PE = 3 SV = 1 | 0 | 0 | 0 |
| 521 | 40S ribosomal protein S25 OS = Homo sapiens GN = RPS25 PE = 2 SV = 1 | 0 | 0 | 0 |
| 522 | 40S ribosomal protein S7 OS = Bos taurus GN = RPS7 PE = 2 SV = 1 | 0 | 0 | 0 |
| 523 | SUMO-activating enzyme subunit 1 OS = Homo sapiens GN = SAE1 PE = 1 SV = 1 | 0 | 0 | 0 |
| 524 | Septin-2 OS = Homo sapiens GN = SEPT2 PE = 1 SV = 1 | 0 | 0 | 0 |
| 525 | Stanniocalcin-2 OS = Homo sapiens GN = STC2 PE = 1 SV = 1 | 0 | 0 | 0 |
| 526 | Isoleucine--tRNA ligase, cytoplasmic OS = Homo sapiens GN = IARS PE = 1 SV = 2 | 0 | 0 | 0 |
| 527 | Tubulin beta-4 chain OS = Caenorhabditis elegans GN = tbb-4 PE = 2 SV = 1 | 0 | 0 | 0 |
| 528 | Tumor necrosis factor receptor superfamily member 11B OS = Homo sapiens GN = TNFRSF11B PE = 1 SV = 3 | 0 | 0 | 0 |
| 529 | Melanotransferrin OS = Homo sapiens GN = MFI2 PE = 1 SV = 2 | 0 | 0 | 0 |
| 530 | NEDD8-conjugating enzyme Ubc12 OS = Bos taurus GN = UBE2M PE = 2 SV = 1 | 0 | 0 | 0 |

TABLE 2

Comparative Gene Ontology for the Proteomic Data

| Cellular component GO | Gene Ontology ID | p-values | | |
|---|---|---|---|---|
| | | HA | UCF | Exo |
| extracellular vesicular exosome | GO: 0070062 | 8.17E−21 | 2.20E−03 | 1.73E−03 |
| extracellular membrane-bounded organelle | GO: 0065010 | 3.26E−20 | 1.87E−03 | 1.18E−03 |
| extracellular organelle | GO: 0043230 | 3.26E−20 | 7.36E−04 | 1.96E−05 |
| membrane-bounded vesicle | GO: 0031988 | 2.90E−15 | 1.62E−04 | 1.75E−08 |
| vesicle | GO: 0031982 | 2.74E−15 | 9.26E−05 | 4.24E−10 |
| cytoplasmic membrane-bounded vesicle | GO: 0016023 | 1.38E−05 | 4.09E−08 | 1.30E−12 |
| cytoplasmic vesicle | GO: 0031410 | 4.32E−05 | 1.29E−05 | 1.20E−11 |

TABLE 3

Comparative microRNA Sequences from Isolated Microvesicles

| | MCF7: Exo | MCF7: HA | MCF7: UCF | MDA-MB-231: Exo | MDA-MB-231: HA | MDA-MB-231: UCF |
|---|---|---|---|---|---|---|
| hsa-let-7a-1 | 3 | 12 | 28 | 28 | 39 | 26 |
| hsa-let-7a-2 | 434 | 419 | 632 | 1965 | 1904 | 1500 |
| hsa-let-7a-3 | 753 | 743 | 616 | 1794 | 1512 | 924 |
| hsa-let-7b | 275 | 328 | 652 | 532 | 396 | 1334 |
| hsa-tet-7c | 8 | 17 | 13 | 6 | 9 | 13 |
| hsa-let-7d | 258 | 257 | 495 | 312 | 239 | 408 |
| hsa-let-7e | 414 | 433 | 691 | 417 | 328 | 632 |
| hsa-let-7f-1 | 501 | 338 | 553 | 404 | 205 | 414 |
| hsa-let-7f-2 | 760 | 792 | 588 | 987 | 972 | 150 |
| hsa-let-7g | 383 | 311 | 6 | 577 | 542 | 4 |
| hsa-let-7i | 343 | 295 | 1215 | 276 | 381 | 420 |
| hsa-mir-100 | 1 | 2 | 0 | 11593 | 8912 | 189 |
| hsa-mir-101-1 | 189 | 143 | 293 | 127 | 234 | 118 |
| hsa-mir-101-2 | 110 | 13 | 131 | 3 | 34 | 43 |
| hsa-mir-103a-1 | 552 | 471 | 522 | 856 | 382 | 590 |
| hsa-mir-103a-2 | 625 | 471 | 654 | 905 | 415 | 714 |
| hsa-mir-103b-2 | 0 | 0 | 1049 | 0 | 0 | 830 |
| hsa-mir-106b | 432 | 421 | 6 | 115 | 206 | 3 |
| hsa-mir-107 | 17 | 18 | 0 | 22 | 20 | 0 |
| hsa-mir-10a | 2 | 0 | 0 | 48 | 181 | 1 |
| hsa-mir-1180 | 17 | 16 | 0 | 5 | 14 | 0 |
| hsa-mir-1246 | 9 | 12 | 13 | 3 | 0 | 0 |
| hsa-mir-1247 | 2 | 4 | 0 | 0 | 0 | 0 |
| hsa-mir-1248 | 3 | 1 | 1 | 8 | 12 | 3 |
| hsa-mir-125a | 553 | 600 | 842 | 719 | 824 | 1642 |
| hsa-mir-125b-1 | 0 | 12 | 0 | 4691 | 4603 | 3456 |
| hsa-mir-125b-2 | 23 | 7 | 12 | 1055 | 681 | 2717 |
| hsa-mir-126 | 41 | 46 | 129 | 125 | 73 | 189 |
| hsa-mir-128-1 | 83 | 67 | 72 | 11 | 17 | 28 |
| hsa-mir-128-2 | 1 | 5 | 21 | 3 | 0 | 1 |
| hsa-mir-1301 | 5 | 8 | 1 | 0 | 1 | 1 |
| hsa-mir-1306 | 6 | 6 | 14 | 1 | 4 | 21 |
| hsa-mir-1307 | 247 | 113 | 9 | 76 | 114 | 2 |
| hsa-mir-130a | 1 | 0 | 1 | 301 | 457 | 254 |
| hsa-mir-130b | 30 | 28 | 54 | 88 | 22 | 43 |
| hsa-mir-132 | 2 | 5 | 1 | 11 | 8 | 0 |
| hsa-mir-135a-1 | 51 | 36 | 91 | 0 | 0 | 0 |
| hsa-mir-135a-2 | 15 | 7 | 8 | 0 | 0 | 0 |
| hsa-mir-135b | 47 | 21 | 0 | 9 | 7 | 0 |
| hsa-mir-138-1 | 0 | 2 | 0 | 196 | 214 | 304 |
| hsa-mir-138-2 | 0 | 0 | 0 | 32 | 28 | 33 |
| hsa-mir-139 | 5 | 2 | 0 | 74 | 68 | 2 |
| hsa-mir-140 | 49 | 39 | 74 | 170 | 140 | 255 |
| hsa-mir-141 | 242 | 225 | 1147 | 2 | 2 | 2 |
| hsa-mir-145 | 4 | 4 | 10 | 12 | 4 | 12 |
| hsa-mir-146a | 0 | 0 | 0 | 207 | 452 | 381 |
| hsa-mir-146b | 13 | 17 | 46 | 17 | 20 | 37 |
| hsa-mir-148a | 121 | 126 | 1 | 154 | 107 | 3 |
| hsa-mir-148b | 51 | 37 | 80 | 29 | 25 | 17 |
| hsa-mir-149 | 22 | 21 | 66 | 16 | 10 | 32 |
| hsa-mir-151a | 449 | 365 | 254 | 814 | 401 | 305 |
| hsa-mir-152 | 16 | 9 | 0 | 24 | 15 | 0 |
| hsa-mir-15a | 319 | 287 | 3 | 53 | 230 | 2 |
| hsa-mir-15b | 224 | 249 | 283 | 68 | 139 | 242 |
| hsa-mir-16-1 | 42 | 67 | 0 | 218 | 320 | 2 |
| hsa-mir-16-2 | 646 | 675 | 825 | 523 | 695 | 857 |
| hsa-mir-17 | 88 | 84 | 155 | 110 | 225 | 189 |
| hsa-mir-181a-1 | 82 | 132 | 50 | 654 | 730 | 322 |
| hsa-mir-181a-2 | 15 | 6 | 22 | 175 | 310 | 528 |
| hsa-mir-181b-2 | 45 | 49 | 30 | 70 | 104 | 102 |
| hsa-mir-181c | 10 | 13 | 17 | 5 | 13 | 5 |
| hsa-mir-182 | 80 | 66 | 9 | 80 | 48 | 7 |
| hsa-mir-183 | 81 | 68 | 1 | 37 | 30 | 0 |

TABLE 3-continued

Comparative microRNA Sequences from Isolated Microvesicles

| | MCF7: Exo | MCF7: HA | MCF7: UCF | MDA-MB-231: Exo | MDA-MB-231: HA | MDA-MB-231: UCF |
|---|---|---|---|---|---|---|
| hsa-mir-185 | 83 | 81 | 154 | 44 | 31 | 65 |
| hsa-mir-186 | 15 | 15 | 0 | 5 | 18 | 0 |
| hsa-mir-188 | 4 | 2 | 16 | 1 | 2 | 1 |
| hsa-mir-18a | 28 | 31 | 71 | 19 | 58 | 25 |
| hsa-mir-191 | 1157 | 1032 | 65 | 1323 | 730 | 59 |
| hsa-mir-192 | 17 | 11 | 0 | 40 | 21 | 0 |
| hsa-mir-193a | 48 | 42 | 70 | 39 | 39 | 42 |
| hsa-mir-193b | 240 | 166 | 324 | 35 | 21 | 51 |
| hsa-mir-195 | 74 | 59 | 0 | 25 | 29 | 0 |
| hsa-mir-197 | 32 | 27 | 27 | 101 | 52 | 235 |
| hsa-mir-19a | 99 | 89 | 319 | 77 | 173 | 162 |
| hsa-mir-19b-1 | 370 | 307 | 547 | 656 | 728 | 345 |
| hsa-mir-19b-2 | 25 | 2 | 4 | 34 | 80 | 3 |
| hsa-mir-200a | 755 | 332 | 1974 | 17 | 33 | 24 |
| hsa-mir-200b | 137 | 124 | 232 | 13 | 22 | 49 |
| hsa-mir-200c | 735 | 563 | 1234 | 5 | 3 | 11 |
| hsa-mir-203a | 232 | 221 | 560 | 0 | 1 | 4 |
| hsa-mir-205 | 33 | 29 | 40 | 2 | 7 | 10 |
| hsa-mir-20a | 36 | 42 | 68 | 25 | 144 | 77 |
| hsa-mir-21 | 22802 | 18466 | 75371 | 11350 | 14198 | 53384 |
| hsa-mir-210 | 53 | 48 | 2 | 111 | 159 | 3 |
| hsa-mir-2110 | 6 | 9 | 0 | 2 | 1 | 0 |
| hsa-mir-218-1 | 0 | 0 | 1 | 67 | 49 | 10 |
| hsa-mir-218-2 | 0 | 0 | 1 | 2 | 9 | 10 |
| hsa-mir-22 | 77 | 84 | 0 | 229 | 102 | 2 |
| hsa-mir-221 | 19 | 24 | 0 | 2327 | 1787 | 7 |
| hsa-mir-222 | 16 | 13 | 2 | 1854 | 1083 | 27 |
| hsa-mir-224 | 0 | 0 | 0 | 11 | 8 | 1 |
| hsa-mir-23a | 1960 | 1813 | 0 | 2702 | 2746 | 0 |
| hsa-mir-23b | 229 | 236 | 617 | 1499 | 1168 | 4578 |
| hsa-mir-24-1 | 587 | 538 | 559 | 4852 | 2679 | 2260 |
| hsa-mir-24-2 | 146 | 80 | 12 | 479 | 229 | 58 |
| hsa-mir-25 | 101 | 79 | 7 | 19 | 21 | 2 |
| hsa-mir-26a-1 | 550 | 554 | 1055 | 738 | 1308 | 1231 |
| hsa-mir-26a-2 | 20 | 17 | 12 | 4 | 17 | 13 |
| hsa-mir-26b | 181 | 152 | 353 | 163 | 196 | 172 |
| hsa-mir-27a | 1148 | 966 | 4 | 1799 | 3665 | 1 |
| hsa-mir-27b | 133 | 144 | 306 | 226 | 687 | 1281 |
| hsa-mir-28 | 10 | 10 | 14 | 14 | 10 | 15 |
| hsa-mir-296 | 24 | 29 | 1 | 0 | 0 | 0 |
| hsa-mir-29a | 496 | 438 | 7 | 772 | 2790 | 9 |
| hsa-mir-29b-1 | 323 | 169 | 0 | 477 | 1619 | 0 |
| hsa-mir-29b-2 | 511 | 260 | 0 | 657 | 2066 | 0 |
| hsa-mir-29c | 247 | 154 | 0 | 147 | 491 | 0 |
| hsa-mir-301a | 192 | 111 | 6 | 38 | 23 | 0 |
| hsa-mir-3065 | 7 | 1 | 22 | 6 | 7 | 10 |
| hsa-mir-3074 | 2 | 0 | 314 | 0 | 0 | 461 |
| hsa-mir-30a | 7 | 5 | 0 | 255 | 481 | 6 |
| hsa-mir-30b | 393 | 369 | 0 | 323 | 525 | 1 |
| hsa-mir-30c-1 | 35 | 43 | 18 | 34 | 80 | 54 |
| hsa-mir-30c-2 | 71 | 78 | 119 | 180 | 327 | 371 |
| hsa-mir-30d | 325 | 442 | 5 | 212 | 394 | 2 |
| hsa-mir-30e | 33 | 30 | 105 | 42 | 97 | 65 |
| hsa-mir-3184 | 0 | 0 | 5 | 0 | 0 | 6 |
| hsa-mir-32 | 21 | 22 | 0 | 12 | 11 | 0 |
| hsa-mir-320a | 199 | 281 | 47 | 572 | 369 | 0 |
| hsa-mir-320b-1 | 1 | 9 | 3 | 5 | 2 | 45 |
| hsa-mir-320c-2 | 0 | 1 | 10 | 17 | 4 | 87 |
| hsa-mir-324 | 96 | 74 | 1 | 41 | 56 | 1 |
| hsa-mir-326 | 10 | 16 | 0 | 7 | 3 | 0 |
| hsa-mir-331 | 11 | 9 | 13 | 21 | 7 | 34 |
| hsa-mir-335 | 93 | 82 | 97 | 8 | 28 | 22 |
| hsa-mir-339 | 234 | 254 | 186 | 49 | 40 | 3 |
| hsa-mir-33a | 7 | 11 | 13 | 3 | 10 | 4 |
| hsa-mir-33b | 18 | 7 | 0 | 1 | 7 | 0 |
| hsa-mir-340 | 26 | 22 | 0 | 2 | 3 | 0 |
| hsa-mir-342 | 3072 | 2134 | 4956 | 149 | 67 | 246 |
| hsa-mir-345 | 22 | 46 | 66 | 13 | 17 | 29 |
| hsa-mir-34a | 240 | 195 | 1 | 117 | 324 | 2 |
| hsa-mir-3529 | 0 | 0 | 108 | 0 | 0 | 7 |
| hsa-mir-361 | 74 | 90 | 1 | 40 | 42 | 1 |
| hsa-mir-362 | 13 | 3 | 12 | 0 | 4 | 1 |
| hsa-mir-3620 | 6 | 5 | 7 | 2 | 1 | 5 |
| hsa-mir-3648 | 31 | 36 | 42 | 4 | 0 | 0 |
| hsa-mir-365a | 111 | 108 | 57 | 2 | 29 | 14 |
| hsa-mir-365b | 7 | 0 | 13 | 0 | 0 | 0 |
| hsa-mir-3676 | 305 | 410 | 541 | 96 | 154 | 281 |
| hsa-mir-3687 | 15 | 48 | 61 | 0 | 0 | 1 |
| hsa-mir-374b | 75 | 56 | 4 | 32 | 32 | 2 |
| hsa-mir-374c | 0 | 0 | 93 | 0 | 0 | 25 |
| hsa-mir-375 | 37 | 64 | 5 | 0 | 2 | 0 |
| hsa-mir-378a | 53 | 41 | 16 | 7 | 8 | 10 |
| hsa-mir-421 | 9 | 7 | 1 | 6 | 7 | 0 |
| hsa-mir-423 | 246 | 228 | 311 | 652 | 190 | 451 |
| hsa-mir-424 | 54 | 46 | 2 | 61 | 132 | 0 |
| hsa-mir-425 | 369 | 326 | 5 | 221 | 106 | 7 |
| hsa-mir-4286 | 1 | 3 | 8 | 9 | 0 | 32 |
| hsa-mir-429 | 119 | 64 | 247 | 6 | 6 | 11 |
| hsa-mir-4454 | 0 | 13 | 0 | 0 | 0 | 63 |
| hsa-mir-4466 | 12 | 12 | 1 | 3 | 0 | 0 |
| hsa-mir-4488 | 1 | 8 | 1 | 1 | 1 | 0 |
| hsa-mir-4492 | 4 | 7 | 4 | 3 | 3 | 2 |
| hsa-mir-4497 | 3 | 5 | 4 | 0 | 0 | 3 |
| hsa-mir-4516 | 12 | 30 | 15 | 1 | 1 | 2 |
| hsa-mir-4532 | 2 | 4 | 1 | 0 | 2 | 2 |
| hsa-mir-454 | 145 | 103 | 1 | 33 | 25 | 0 |
| hsa-mir-455 | 3 | 8 | 12 | 511 | 171 | 573 |
| hsa-mir-484 | 456 | 388 | 487 | 146 | 52 | 133 |
| hsa-mir-486 | 2 | 1 | 0 | 24 | 7 | 20 |
| hsa-mir-489 | 296 | 225 | 18 | 8 | 6 | 1 |
| hsa-mir-497 | 45 | 40 | 0 | 3 | 10 | 0 |
| hsa-mir-500a | 9 | 7 | 10 | 0 | 1 | 2 |
| hsa-mir-501 | 7 | 9 | 7 | 1 | 0 | 1 |
| hsa-mir-502 | 1 | 8 | 1 | 0 | 1 | 1 |
| hsa-mir-503 | 26 | 20 | 3 | 14 | 35 | 3 |
| hsa-mir-505 | 36 | 33 | 3 | 14 | 20 | 0 |
| hsa-mir-532 | 7 | 11 | 7 | 2 | 2 | 13 |
| hsa-mir-551b | 0 | 0 | 1 | 126 | 79 | 60 |
| hsa-mir-574 | 25 | 37 | 22 | 119 | 232 | 878 |
| hsa-mir-590 | 37 | 18 | 85 | 23 | 22 | 18 |
| hsa-mir-6087 | 39 | 43 | 68 | 18 | 17 | 46 |
| hsa-mir-625 | 58 | 41 | 142 | 46 | 33 | 85 |
| hsa-mir-629 | 9 | 15 | 1 | 6 | 4 | 0 |
| hsa-mir-642a | 5 | 1 | 1 | 5 | 3 | 19 |
| hsa-mir-652 | 73 | 75 | 201 | 33 | 19 | 47 |
| hsa-mir-653 | 17 | 19 | 0 | 0 | 1 | 0 |
| hsa-mir-660 | 60 | 57 | 145 | 1 | 14 | 16 |
| hsa-mir-663a | 13 | 13 | 0 | 1 | 0 | 0 |
| hsa-mir-663b | 1 | 1 | 1 | 0 | 0 | 0 |
| hsa-mir-664a | 6 | 7 | 0 | 6 | 11 | 0 |
| hsa-mir-671 | 9 | 12 | 6 | 14 | 9 | 16 |
| hsa-mir-708 | 6 | 6 | 0 | 7 | 2 | 0 |
| hsa-mir-7-1 | 123 | 83 | 94 | 19 | 19 | 6 |
| hsa-mir-7-2 | 5 | 0 | 94 | 0 | 0 | 6 |
| hsa-mir-7-3 | 5 | 0 | 94 | 0 | 0 | 6 |
| hsa-mir-744 | 7 | 10 | 15 | 27 | 24 | 49 |
| hsa-mir-769 | 7 | 9 | 33 | 15 | 14 | 41 |
| hsa-mir-877 | 1 | 5 | 8 | 3 | 3 | 4 |
| hsa-mir-9-2 | 12 | 8 | 9 | 1 | 3 | 0 |
| hsa-mir-92a-1 | 51 | 33 | 49 | 128 | 145 | 250 |
| hsa-mir-92a-2 | 30 | 18 | 11 | 2 | 13 | 2 |
| hsa-mir-92b | 45 | 35 | 71 | 108 | 109 | 304 |
| hsa-mir-93 | 306 | 349 | 9 | 170 | 256 | 1 |
| hsa-mir-935 | 2 | 5 | 15 | 1 | 0 | 0 |
| hsa-mir-941-1 | 2 | 3 | 5 | 3 | 3 | 13 |
| hsa-mir-941-3 | 2 | 3 | 5 | 3 | 3 | 13 |
| hsa-mir-95 | 9 | 8 | 1 | 2 | 1 | 0 |
| hsa-mir-96 | 16 | 22 | 1 | 18 | 29 | 0 |
| hsa-mir-98 | 76 | 66 | 3 | 25 | 25 | 0 |
| hsa-mir-99a | 51 | 36 | 75 | 14 | 15 | 45 |
| hsa-mir-99b | 256 | 330 | 766 | 319 | 186 | 1139 |

TABLE 4

Differential Protein Content of Isolated MIcrovesicles from Different Breast Cancer Cell Condition Media: Proteomic Analysis

| Proteins | % of the protein covered by peptides identified by MS | |
|---|---|---|
| | MCF10A MVs | MCF7 MVs |
| Actin, cytoplasmic 1 | 29% | 46% |
| Keratin, type I cytoskeletal 18 | 1.60% | 52% |
| Glyceraldehyde-3-phosphate dehydrogenase | 32% | 48% |
| Alpha-enolase OS = Homo sapiens | 37% | 38% |
| 60 kDa heat shock protein, mitochondrial | 38% | 23% |
| Fatty acid synthase | 0% | 17% |
| Histone H2A | 36% | 27% |
| Annexin A2 | 40% | 25% |
| Heat shock protein HSP 90-beta | 3.60% | 26% |
| L-lactate dehydrogenase A chain | 33% | 16% |
| Histone H4 | 50% | 49% |
| Pyruvate kinase isozymes M1/M2 | 14% | 37% |
| Renin receptor | 22% | 25% |
| Clathrin heavy chain 1 | 0% | 16% |
| Aminopeptidase N | 12% | 0% |
| Cathepsin D | 9.50% | 24% |
| Heat shock cognate 71 kDa protein | 6.30% | 24% |
| Transforming growth factor-beta-induced protein ig-h3 | 14% | 0 |
| Peroxiredoxin-6 | 49% | 22% |
| Tubutin alpha-1B chain | 7.50% | 21% |
| Phosphoglycerate kinase | 12% | 29% |
| Thrombospondin-1 | 1.00% | 15% |

REFERENCES

1. Soo C Y, Song Y, Zheng Y, Campbell E C, Riches A C, Gunn-Moore F, Powis S J. Nanoparticle tracking analysis monitors microvesicle and exosome secretion from immune cells. Immunology. 2012 June; 136(2):192-7.
2. Meckes D G Jr, Raab-Traub N. Microvesicles and viral infection. J Virol. 2011 December; 85(24):12844-54.
3. Camussi G, Deregibus M C, Bruno S, Grange C, Fonsato V, Tetta C. Exosome/microvesicle-mediated epigenetic reprogramming of cells. Am J Cancer Res. 2011; 1(1): 98-110.
4. Liu M L, Williams K J. Microvesicles: potential markers and mediators of endothelial dysfunction. Curr Opin Endocrinol Diabetes Obes. 2012 April; 19(2):121-7.
5. Taylor D D, Gercel-Taylor C. Exosomes/microvesicles: mediators of cancer-associated immunosuppressive microenvironments. Semin Immunopathol. 2011 September; 33(5):441-54.
6. Tetta C, Bruno S, Fonsato V, Deregibus M C, Camussi G. The role of microvesicles in tissue repair. Organogenesis. 2011 April-June; 7(2):105-15.
7. Pap E. The role of microvesicles in malignancies. Adv Exp Med Biol. 2011; 714:183-99.
8. Xiong J, Miller V M, Li Y, Jayachandran M. Microvesicles at the crossroads between infection and cardiovascular diseases. J Cardiovasc Pharmacol. 2012 February; 59(2):124-33.
9. Rautou P E, Mackman N., Del-etion of microvesicles from the circulation. Circulation. 2012; 125: 1601-1604.
10. Sadallah S, Eken C, Schifferli J A. Ectosomes as modulators of inflammation and immunity. Sadallah S, Eken C, Schifferli J A. Clin Exp Immunol. 2011 January; 163(1):26-32.
11. Camussi G, Deregibus M C, Bruno S, Cantaluppi V, Biancone L. Exosomes/microvesicles as a mechanism of cell-to-cell communication. Kidney Int. 2010 November; 78(9):838-48.
12. D'Souza-Schorey C, Clancy J W. Tumor-derived microvesicles: shedding light on novel microenvironment modulators and prospective cancer biomarkers. Genes Dev. 2012 June 15; 26(12):1287-99.
13. György B, Szabó T G, Pásztói M, Pál Z, Misják P, Aradi B, László V, Pállinger E, Pap E, Kittel A, Nagy G, Falus A, Buzás E I. Membrane vesicles, current state-of-the-art: emerging role of extracellular vesicles. Cell Mol Life Sci. 2011 August; 68(16):2667-88. doi: 10.1007/s00018-011-0689-3.
14. Biomarkers Definitions Working Group. Biomarkers and surrogate endpoints: preferred definitions and conceptual framework. Clin Pharmacol Ther. 2001; 69: 89-95.
15. Pouyani T, Prestwich G D, Biotinylated hyaluronic acid: a new tool for probing hyaluronate-receptor interactions. Bioconjug Chem. 1994 July-August; 5(4):370-2

The invention claimed is:
1. A method for the isolation of microvesicles from a biological sample containing microvesicles, comprising:
(i) obtaining the biological sample of bodily fluid, conditioned media, stool, or a biopsy from a tissue, organ, lymph or bone marrow;
(ii) clearing the biological sample by:
ii.a) centrifugation; and/or
ii.b) filtration to obtain a cleared biological sample that is substantially free of cells and cellular debris;
(ii) contacting the cleared biological sample with a solution comprising at least one polysaccharide to form a polysaccharide-microvesicle complex, wherein the polysaccharide has a molecular weight of at least 15 kDa, wherein the polysaccharide is mannan, chitin, a glycosaminoglycan, or any derivatives of any of the above, and wherein the polysaccharide-microvesicle complex is not formed as a result of specific target binding interactions;
(iv) separating the polysaccharide-microvesicle complex from the solution by:
iv.a) sedimenting the polysaccharide-microvesicle complex by centrifugation of the solution; and/or
iv.b) filtering the polysaccharide-microvesicle complex from the solution;
(v) retaining the polysaccharide-microvesicle complex by discarding the supernatant and/or filtrate, thereby isolating microvesicles from the biological sample.
2. The method according to claim 1, wherein the polysaccharide is a natural or synthetic polysaccharide.
3. The method according to claim 1, wherein the polysaccharide is a linear or branched polysaccharide.
4. The method according to claim 1, wherein the glycosaminoglycan is heparin, heparan sulfate or hyaluronan.
5. The method according to claim 1, wherein the polysaccharide is bonded to a solid-matrix.
6. The method according to claim 5, wherein the solid matrix comprises polystyrene or glass or a paramagnetic particle or a microfluidic apparatus.
7. The method according to claim 1, wherein the biological sample is derived from a subject with cancer or other pathological condition.
8. The method according to claim 1, wherein the sample is contacted with the polysaccharide at a temperature of 2° C. to 37° C. for about 10 minutes to 20 hours.
9. The method according to claim 1, wherein the solution is subjected to a centrifugal force of 3,000 g to 20,000 g.

10. The method according to claim 1, wherein the solution is filtered using a filter with a pore size of 0.45 μm to 2.0 μm.

11. A method for the diagnosis of a pathological condition comprising:
   (i) obtaining a biological sample from a subject;
   (ii) isolating microvesicles from the sample using a method defined in claim 1;
   (iii) detecting:
      (a) one or more pathological markers, and/or markers for a particular tissue or cell-type, wherein the presence of the pathological marker in the sample indicates the presence of the condition in the subject; and/or
      (b) one or more healthy normal markers for a particular tissue or cell-type, wherein the absence or decrease of the healthy normal marker in the sample indicates the presence of the pathological condition in the subject.

12. A method for the diagnosis of a pathological condition comprising:
   (i) obtaining a biological sample from a subject;
   (ii) isolating microvesicles from the sample using a method defined in claim 1;
   (iii) measuring the isolated microvesicles for one or more:
      (a) biomarkers for the pathological condition, (b) other pathological markers; and/or (c) markers for a particular tissue or cell-type,
   (iv) comparing the level of markers defined in step (iii) to a reference value, wherein if the level of markers is increased or decreased relative to the reference value, identifying the subject as having an increased probability of having the pathological condition.

13. The method according to claim 11, wherein the pathological condition is cancer, cardiovascular disease, genetic disease, liver disease, chronic kidney disease, respiratory disease, autoimmune diseases, heart disease, stroke, asthma, diabetes, osteoporosis, Alzheimer's disease, or an infectious disease, wherein the infectious disease is caused by a virus, bacteria, fungi, protozoa, multicellular organism or a prion.

14. An assay for detecting a pathological condition in a subject, comprising,
   (i) obtaining a biological sample from the subject;
   (ii) isolating microvesicles from the sample using a method as defined in claim 1;
   (iii) measuring the isolated microvesicles for one or more:
      (a) biomarkers for the pathological condition, (b) other pathological markers; and/or (c) markers for a particular tissue or cell-type,
   (iv) comparing the level of markers defined in step (iii) to a reference value, wherein if the level of markers is increased or decreased relative to the reference value, identifying the subject as having an increased probability of having the pathological condition.

15. The assay according to claim 14, wherein the pathological condition is cancer, cardiovascular disease, genetic disease, liver disease, chronic kidney disease, respiratory disease, autoimmune diseases, heart disease, stroke, asthma, diabetes, osteoporosis, Alzheimer's disease, or an infectious disease, wherein the infectious disease is caused by a virus, bacteria, fungi, protozoa, multicellular organism or a prion.

16. A method for determining if a subject, suffering from a pathological condition, is responsive to a therapy for the treatment of the condition, comprising,
   (i) performing an assay for detecting a pathological condition in a subject as defined in claim 14;
   (ii) subsequently administering the therapy to the subject;
   (iii) performing a second assay as described in claim 14 in a second biological sample obtained from the subject, wherein a decrease in the level of markers in the second biological sample indicates the subject is responsive to the therapy.

17. The method according to claim 16, wherein the pathological condition is cancer, cardiovascular disease, genetic disease, liver disease, chronic kidney disease, respiratory disease, autoimmune diseases, heart disease, stroke, asthma, diabetes, osteoporosis, Alzheimer's disease, or an infectious disease, wherein the infectious disease is caused by a virus, bacteria, fungi, protozoa, multicellular organism or a prion.

18. An assay for detecting a pathological condition in, or contamination of, a food product, comprising:
   (i) obtaining a sample from the food product or source organism;
   (ii) isolating microvesicles from the sample using a method as defined in claim 1;
   (iii) detecting one or more pathological markers, such as a pathogenic, infectious or other disease condition, wherein the presence of the pathological marker in the sample indicates the presence of the pathological condition in the sample.

19. An assay for detecting a pathological condition in a wild, domestic or farmed animal, bird or fish, comprising:
   (i) obtaining a sample from the organism;
   (ii) isolating microvesicles from the sample using a method as defined in claim 1;
   (iii) detecting one or more pathological markers, such as a pathogenic, infectious or other disease condition, wherein the presence of the pathological marker in the sample indicates the presence of the pathological condition in the sample.

20. An assay for detecting and characterizing microvesicles from a fluid, media or discharge from an organism, comprising:
   (i) obtaining a sample from the organism;
   (ii) isolating microvesicles from the sample using a method as defined in claim 1;
   (iii) detecting one or more markers, wherein the marker is a microvesicle-specific protein, RNA or other molecular characterization.

21. The method according to claim 1, wherein the polysaccharide has a molecular weight of at least 100 kDa.

22. The method according to claim 1, wherein the polysaccharide has a molecular weight of at least 500 kDa.

23. The method according to claim 1, wherein the polysaccharide has a molecular weight of at least 1 MDa.

24. The method according to claim 1, wherein the bodily fluid is whole blood, blood serum, plasma, sputum, seminal fluid, urine, milk, or saliva.

* * * * *